United States Patent
Sundstrom et al.

(10) Patent No.: US 12,154,450 B2
(45) Date of Patent: Nov. 26, 2024

(54) USER INTERFACES FOR TRACKING OF PHYSICAL ACTIVITY EVENTS

(71) Applicant: Apple Inc., Cupertino, CA (US)

(72) Inventors: Matthew J. Sundstrom, Campbell, CA (US); Nicholas Felton, Sunnyvale, CA (US); Gary Ian Butcher, Los Gatos, CA (US); Joseph Y. Chan, San Francisco, CA (US); Jules K. Fennis, Auburn, WA (US); Eamon Francis Gilravi, San Francisco, CA (US); Nicholas V. King, San Jose, CA (US); Cas Lemmens, San Francisco, CA (US); Joseph M. Luxton, San Francisco, CA (US); Camille Moussette, San Francisco, CA (US); Charmian Bondoc Naguit, San Francisco, CA (US); Hugo Verweij, San Francisco, CA (US); Molly Pray Wiebe, San Francisco, CA (US); Kevin Lynch, Woodside, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/337,147

(22) Filed: Jun. 2, 2021

(65) Prior Publication Data
US 2021/0375157 A1    Dec. 2, 2021

Related U.S. Application Data

(60) Provisional application No. 63/033,814, filed on Jun. 2, 2020.

(51) Int. Cl.
*G09B 19/00*    (2006.01)
*A61B 5/11*    (2006.01)
(Continued)

(52) U.S. Cl.
CPC ........ *G09B 19/0076* (2013.01); *A61B 5/1123* (2013.01); *G06F 3/0481* (2013.01); *G16H 20/30* (2018.01)

(58) Field of Classification Search
CPC .. G09B 19/0076; G16H 20/30; A61B 5/1123; G06F 3/0481
See application file for complete search history.

(56) References Cited

U.S. PATENT DOCUMENTS 5,515,344 A    5/1996   Ng
5,642,731 A    7/1997   Kehr
(Continued)

FOREIGN PATENT DOCUMENTS

CA    2815518 A1    5/2012
CN    102448555 A    5/2012
(Continued)

OTHER PUBLICATIONS

Decision to Grant received for Danish Patent Application No. PA202070619, mailed on Aug. 11, 2022, 2 pages.
(Continued)

*Primary Examiner* — William L Bashore
*Assistant Examiner* — Gregory A Distefano
(74) *Attorney, Agent, or Firm* — DLA Piper LLP (US)

(57) ABSTRACT

The present disclosure generally relates to methods for tracking the performance of a physical activity event. In some embodiments, the method is performed at a computer system that is in communication with one or more perceptual output generation components and one or more sensors and includes detecting a start of a physical activity, providing ongoing feedback relating to a target duration, and if the activity continues for at least the duration, indicating that the activity continued for at least the target duration.

39 Claims, 23 Drawing Sheets

(51) Int. Cl.
*G06F 3/0481* (2022.01)
*G16H 20/30* (2018.01)

(56) References Cited

U.S. PATENT DOCUMENTS

| | | | |
|---|---|---|---|
| 6,298,314 B1 * | 10/2001 | Blackadar | A61B 5/6831 |
| | | | 235/105 |
| 6,416,471 B1 | 7/2002 | Kumar et al. | |
| 6,475,115 B1 * | 11/2002 | Candito | A63B 24/0059 |
| | | | 482/901 |
| 6,600,696 B1 | 7/2003 | Lynn | |
| 6,705,972 B1 | 3/2004 | Takano et al. | |
| 6,873,709 B2 | 3/2005 | Hou | |
| 6,950,839 B1 | 9/2005 | Green et al. | |
| 7,111,157 B1 | 9/2006 | Hooper | |
| 7,128,693 B2 | 10/2006 | Brown et al. | |
| 7,166,078 B2 | 1/2007 | Saini et al. | |
| 7,313,435 B2 | 12/2007 | Nakada et al. | |
| 7,739,148 B2 | 6/2010 | Suzuki et al. | |
| 7,771,320 B2 | 8/2010 | Riley et al. | |
| 8,045,739 B2 | 10/2011 | Paludan-Mueller et al. | |
| 8,152,694 B2 | 4/2012 | Srinivasan et al. | |
| 8,200,323 B2 | 6/2012 | Dibenedetto et al. | |
| 8,321,006 B1 | 11/2012 | Snyder et al. | |
| 8,475,339 B2 | 7/2013 | Hwang et al. | |
| 8,676,170 B2 | 3/2014 | Porrati et al. | |
| 8,725,527 B1 | 5/2014 | Kahn et al. | |
| 8,758,262 B2 | 6/2014 | Rhee et al. | |
| 8,784,115 B1 | 7/2014 | Chuang | |
| 8,888,707 B2 | 11/2014 | Shirasaki et al. | |
| 9,011,292 B2 | 4/2015 | Weast et al. | |
| 9,026,927 B2 | 5/2015 | Brumback et al. | |
| 9,224,291 B2 | 12/2015 | Moll-carrillo et al. | |
| 9,490,763 B2 | 11/2016 | Taniguchi et al. | |
| 9,579,060 B1 | 2/2017 | Lisy et al. | |
| 9,589,445 B2 | 3/2017 | White et al. | |
| 9,606,695 B2 | 3/2017 | Matas | |
| 9,672,715 B2 | 6/2017 | Roberts et al. | |
| 9,712,629 B2 | 7/2017 | Molettiere et al. | |
| 9,721,066 B1 | 8/2017 | Funaro et al. | |
| 9,730,621 B2 | 8/2017 | Cohen et al. | |
| 9,801,562 B1 | 10/2017 | Host-madsen | |
| 9,808,206 B1 | 11/2017 | Zhao et al. | |
| 9,813,642 B1 | 11/2017 | Chen et al. | |
| 9,940,682 B2 | 4/2018 | Hoffman et al. | |
| 10,004,451 B1 | 6/2018 | Proud | |
| 10,010,750 B2 | 7/2018 | Tropper et al. | |
| 10,150,002 B2 | 12/2018 | Kass et al. | |
| 10,175,781 B2 | 1/2019 | Karagozler et al. | |
| 10,226,195 B2 | 3/2019 | Briante et al. | |
| 10,254,911 B2 | 4/2019 | Yang | |
| 10,275,262 B1 | 4/2019 | Bull et al. | |
| 10,339,830 B2 | 7/2019 | Han et al. | |
| 10,365,811 B2 | 7/2019 | Robinson et al. | |
| 10,437,962 B2 | 10/2019 | Soni et al. | |
| 10,445,702 B1 | 10/2019 | Hunt | |
| 10,565,894 B1 | 2/2020 | Jain et al. | |
| 10,568,533 B2 | 2/2020 | Soli et al. | |
| 10,576,327 B2 | 3/2020 | Kim et al. | |
| 10,592,088 B2 | 3/2020 | Robinson et al. | |
| 10,602,964 B2 | 3/2020 | Kerber | |
| 10,635,267 B2 | 4/2020 | Williams | |
| 10,674,942 B2 | 6/2020 | Williams et al. | |
| 10,685,090 B2 | 6/2020 | Petterson et al. | |
| 10,762,990 B1 | 9/2020 | Schilling et al. | |
| 10,764,700 B1 | 9/2020 | Felton | |
| 10,796,549 B2 | 10/2020 | Roberts et al. | |
| 11,073,942 B2 | 7/2021 | Lee et al. | |
| 11,103,161 B2 | 8/2021 | Williams et al. | |
| 11,107,580 B1 | 8/2021 | Felton et al. | |
| 11,209,957 B2 | 12/2021 | Dryer et al. | |
| 2002/0095292 A1 | 7/2002 | Mittal et al. | |
| 2003/0181291 A1 | 9/2003 | Ogawa | |
| 2003/0191609 A1 | 10/2003 | Bernardi et al. | |
| 2003/0200483 A1 | 10/2003 | Sutton | |
| 2003/0216971 A1 | 11/2003 | Sick et al. | |
| 2003/0226695 A1 | 12/2003 | Mault | |
| 2004/0017300 A1 | 1/2004 | Kotzin et al. | |
| 2004/0077958 A1 | 4/2004 | Kato et al. | |
| 2004/0081024 A1 | 4/2004 | Weng | |
| 2004/0190729 A1 | 9/2004 | Yonovitz et al. | |
| 2004/0193069 A1 | 9/2004 | Takehara | |
| 2004/0210117 A1 | 10/2004 | Ueno et al. | |
| 2004/0236189 A1 | 11/2004 | Hawthorne et al. | |
| 2005/0010117 A1 | 1/2005 | Agutter et al. | |
| 2005/0027208 A1 | 2/2005 | Shiraishi et al. | |
| 2005/0075214 A1 | 4/2005 | Brown et al. | |
| 2005/0079905 A1 | 4/2005 | Martens | |
| 2005/0149362 A1 | 7/2005 | Peterson et al. | |
| 2005/0228735 A1 | 10/2005 | Duquette | |
| 2005/0244013 A1 | 11/2005 | Battenberg et al. | |
| 2005/0272564 A1 | 12/2005 | Pyles et al. | |
| 2006/0094969 A1 | 5/2006 | Nissila | |
| 2006/0098109 A1 | 5/2006 | Ooki | |
| 2006/0106741 A1 | 5/2006 | Janarthanan | |
| 2006/0136173 A1 | 6/2006 | Case, Jr. et al. | |
| 2006/0149144 A1 | 7/2006 | Lynn et al. | |
| 2006/0152372 A1 | 7/2006 | Stout | |
| 2006/0182287 A1 | 8/2006 | Schulein et al. | |
| 2006/0205564 A1 | 9/2006 | Peterson | |
| 2006/0210096 A1 | 9/2006 | Stokes et al. | |
| 2006/0235319 A1 | 10/2006 | Belohlavek et al. | |
| 2006/0274908 A1 | 12/2006 | Choi | |
| 2007/0016440 A1 | 1/2007 | Stroup | |
| 2007/0056727 A1 | 3/2007 | Newman | |
| 2007/0179434 A1 | 8/2007 | Weinert et al. | |
| 2007/0250505 A1 | 10/2007 | Yang et al. | |
| 2007/0250613 A1 | 10/2007 | Gulledge | |
| 2007/0274531 A1 | 11/2007 | Camp | |
| 2008/0012701 A1 | 1/2008 | Kass et al. | |
| 2008/0058626 A1 | 3/2008 | Miyata et al. | |
| 2008/0133742 A1 | 6/2008 | Southiere et al. | |
| 2008/0146892 A1 | 6/2008 | Leboeuf et al. | |
| 2008/0159547 A1 | 7/2008 | Schuler et al. | |
| 2008/0200312 A1 | 8/2008 | Tagliabue | |
| 2008/0205660 A1 | 8/2008 | Goldstein | |
| 2008/0228045 A1 | 9/2008 | Gao et al. | |
| 2008/0240519 A1 | 10/2008 | Nagamitsu | |
| 2008/0300110 A1 | 12/2008 | Smith et al. | |
| 2009/0007596 A1 | 1/2009 | Goldstein et al. | |
| 2009/0052677 A1 | 2/2009 | Smith | |
| 2009/0065578 A1 | 3/2009 | Peterson et al. | |
| 2009/0118100 A1 | 5/2009 | Oliver et al. | |
| 2009/0180631 A1 | 7/2009 | Michael et al. | |
| 2009/0210078 A1 | 8/2009 | Crowley | |
| 2009/0216556 A1 | 8/2009 | Martin et al. | |
| 2009/0235253 A1 | 9/2009 | Hope | |
| 2009/0245537 A1 | 10/2009 | Morin | |
| 2009/0259134 A1 | 10/2009 | Levine | |
| 2009/0262088 A1 | 10/2009 | Moll-carrillo et al. | |
| 2009/0267776 A1 * | 10/2009 | Glenn | G16H 40/20 |
| | | | 340/573.1 |
| 2009/0287103 A1 | 11/2009 | Pillai | |
| 2009/0287327 A1 | 11/2009 | Hsu et al. | |
| 2009/0290721 A1 | 11/2009 | Goldstein et al. | |
| 2010/0003951 A1 | 1/2010 | Ray et al. | |
| 2010/0010832 A1 | 1/2010 | Boute et al. | |
| 2010/0017489 A1 | 1/2010 | Birnbaum et al. | |
| 2010/0027807 A1 | 2/2010 | Jeon | |
| 2010/0046767 A1 | 2/2010 | Bayley et al. | |
| 2010/0062905 A1 | 3/2010 | Rottler et al. | |
| 2010/0073162 A1 * | 3/2010 | Johnson | G08B 21/245 |
| | | | 340/540 |
| 2010/0076331 A1 | 3/2010 | Chan et al. | |
| 2010/0099539 A1 | 4/2010 | Haataja | |
| 2010/0119093 A1 | 5/2010 | Uzuanis et al. | |
| 2010/0121700 A1 | 5/2010 | Wigder et al. | |
| 2010/0145220 A1 | 6/2010 | Van | |
| 2010/0150378 A1 | 6/2010 | Lee et al. | |
| 2010/0222645 A1 | 9/2010 | Nadler et al. | |
| 2010/0292600 A1 | 11/2010 | Dibenedetto et al. | |
| 2010/0312138 A1 | 12/2010 | Regas | |
| 2011/0057799 A1 * | 3/2011 | Taneff | G08B 21/245 |
| | | | 340/573.1 |

(56) References Cited

U.S. PATENT DOCUMENTS

| | | |
|---|---|---|
| 2011/0066051 A1 | 3/2011 | Moon et al. |
| 2011/0071765 A1 | 3/2011 | Yodfat et al. |
| 2011/0093481 A1 | 4/2011 | Hussam |
| 2011/0098928 A1 | 4/2011 | Hoffman et al. |
| 2011/0152656 A1 | 6/2011 | Weinert et al. |
| 2011/0166631 A1 | 7/2011 | Breining |
| 2011/0195383 A1 | 8/2011 | Weiss |
| 2011/0214162 A1 | 9/2011 | Brakensiek et al. |
| 2011/0218407 A1 | 9/2011 | Haberman et al. |
| 2011/0245623 A1 | 10/2011 | Chutani et al. |
| 2011/0307821 A1 | 12/2011 | Martens |
| 2012/0002510 A1 | 1/2012 | Berman, Jr. |
| 2012/0029303 A1 | 2/2012 | Shaya |
| 2012/0038651 A1 | 2/2012 | Case et al. |
| 2012/0041767 A1 | 2/2012 | Hoffman et al. |
| 2012/0059664 A1 | 3/2012 | Georgiev et al. |
| 2012/0065480 A1 | 3/2012 | Badilini et al. |
| 2012/0071770 A1 | 3/2012 | Grey et al. |
| 2012/0112908 A1 | 5/2012 | Prykaeri et al. |
| 2012/0116550 A1 | 5/2012 | Hoffman et al. |
| 2012/0203124 A1 | 8/2012 | Lim |
| 2012/0215115 A1 | 8/2012 | Takahashi |
| 2012/0245447 A1 | 9/2012 | Karan et al. |
| 2012/0283524 A1 | 11/2012 | Kiani et al. |
| 2012/0283587 A1 | 11/2012 | Gosh et al. |
| 2012/0283855 A1 | 11/2012 | Hoffman et al. |
| 2012/0311585 A1 | 12/2012 | Gruber et al. |
| 2012/0316455 A1 | 12/2012 | Rahman et al. |
| 2012/0317167 A1 | 12/2012 | Rahman et al. |
| 2012/0321094 A1 | 12/2012 | Schiller et al. |
| 2013/0002425 A1 | 1/2013 | Hatch et al. |
| 2013/0007155 A1* | 1/2013 | Moore ............... G06Q 10/101 709/206 |
| 2013/0011819 A1 | 1/2013 | Horseman |
| 2013/0012788 A1 | 1/2013 | Horseman |
| 2013/0013331 A1 | 1/2013 | Horseman |
| 2013/0033376 A1 | 2/2013 | Seyed et al. |
| 2013/0065569 A1 | 3/2013 | Leipzig et al. |
| 2013/0072765 A1 | 3/2013 | Kahn et al. |
| 2013/0073933 A1 | 3/2013 | Eppolito |
| 2013/0073960 A1 | 3/2013 | Eppolito et al. |
| 2013/0095459 A1 | 4/2013 | Tran |
| 2013/0110264 A1 | 5/2013 | Weast et al. |
| 2013/0114100 A1 | 5/2013 | Torii et al. |
| 2013/0115583 A1 | 5/2013 | Gordon et al. |
| 2013/0144653 A1 | 6/2013 | Poe et al. |
| 2013/0151285 A1 | 6/2013 | Mclaren et al. |
| 2013/0158416 A1 | 6/2013 | Hatlestad et al. |
| 2013/0197679 A1 | 8/2013 | Balakrishnan et al. |
| 2013/0202121 A1 | 8/2013 | Georgiou et al. |
| 2013/0215042 A1 | 8/2013 | Messerschmidt et al. |
| 2013/0231575 A1 | 9/2013 | Erkkila et al. |
| 2013/0231947 A1 | 9/2013 | Shusterman |
| 2013/0268398 A1 | 10/2013 | Agami et al. |
| 2013/0274628 A1 | 10/2013 | Fausti et al. |
| 2013/0304616 A1 | 11/2013 | Raleigh et al. |
| 2013/0317380 A1 | 11/2013 | Liley et al. |
| 2013/0325396 A1 | 12/2013 | Yuen et al. |
| 2013/0332286 A1 | 12/2013 | Medelius et al. |
| 2014/0005947 A1 | 1/2014 | Jeon et al. |
| 2014/0037107 A1 | 2/2014 | Marino et al. |
| 2014/0038781 A1 | 2/2014 | Foley et al. |
| 2014/0073486 A1 | 3/2014 | Ahmed et al. |
| 2014/0081118 A1 | 3/2014 | Reinhold et al. |
| 2014/0088995 A1 | 3/2014 | Damani |
| 2014/0127996 A1 | 5/2014 | Park et al. |
| 2014/0129007 A1 | 5/2014 | Utter |
| 2014/0129243 A1 | 5/2014 | Utter |
| 2014/0135592 A1 | 5/2014 | Ohnemus et al. |
| 2014/0142403 A1 | 5/2014 | Brumback et al. |
| 2014/0143678 A1 | 5/2014 | Mistry et al. |
| 2014/0164611 A1 | 6/2014 | Molettiere et al. |
| 2014/0173521 A1 | 6/2014 | Mayor |
| 2014/0176335 A1 | 6/2014 | Brumback et al. |
| 2014/0176475 A1 | 6/2014 | Myers et al. |
| 2014/0180595 A1 | 6/2014 | Brumback et al. |
| 2014/0184422 A1 | 7/2014 | Mensinger et al. |
| 2014/0189510 A1 | 7/2014 | Ozcan |
| 2014/0197946 A1 | 7/2014 | Park et al. |
| 2014/0200426 A1 | 7/2014 | Taub et al. |
| 2014/0240122 A1 | 8/2014 | Roberts et al. |
| 2014/0240349 A1 | 8/2014 | Tuukkanen |
| 2014/0266776 A1 | 9/2014 | Miller et al. |
| 2014/0275852 A1 | 9/2014 | Hong et al. |
| 2014/0275856 A1 | 9/2014 | Kohlrausch et al. |
| 2014/0278220 A1 | 9/2014 | Yuen |
| 2014/0288390 A1 | 9/2014 | Hong et al. |
| 2014/0297217 A1 | 10/2014 | Yuen |
| 2014/0327527 A1 | 11/2014 | Goldstein et al. |
| 2014/0336796 A1 | 11/2014 | Agnew |
| 2014/0344687 A1 | 11/2014 | Durham et al. |
| 2014/0354494 A1 | 12/2014 | Katz |
| 2014/0358012 A1 | 12/2014 | Richards et al. |
| 2014/0371887 A1 | 12/2014 | Hoffman et al. |
| 2015/0057942 A1 | 2/2015 | Self et al. |
| 2015/0073285 A1 | 3/2015 | Albert et al. |
| 2015/0081210 A1 | 3/2015 | Yeh et al. |
| 2015/0089536 A1 | 3/2015 | Byerley |
| 2015/0099991 A1 | 4/2015 | Yamaguchi et al. |
| 2015/0100348 A1 | 4/2015 | Connery et al. |
| 2015/0106025 A1 | 4/2015 | Keller et al. |
| 2015/0110277 A1 | 4/2015 | Pidgeon et al. |
| 2015/0110279 A1 | 4/2015 | Tejerina |
| 2015/0120633 A1 | 4/2015 | Norlander et al. |
| 2015/0124067 A1 | 5/2015 | Bala et al. |
| 2015/0125832 A1 | 5/2015 | Tran |
| 2015/0127365 A1 | 5/2015 | Rizvi et al. |
| 2015/0142689 A1 | 5/2015 | Squires |
| 2015/0164349 A1 | 6/2015 | Gopalakrishnan et al. |
| 2015/0173686 A1 | 6/2015 | Furuta et al. |
| 2015/0179186 A1 | 6/2015 | Swierk et al. |
| 2015/0181314 A1 | 6/2015 | Swanson |
| 2015/0182843 A1 | 7/2015 | Esposito et al. |
| 2015/0185967 A1 | 7/2015 | Ly et al. |
| 2015/0193217 A1 | 7/2015 | Xiang et al. |
| 2015/0196804 A1 | 7/2015 | Koduri et al. |
| 2015/0205947 A1 | 7/2015 | Berman et al. |
| 2015/0216448 A1 | 8/2015 | Lotan et al. |
| 2015/0217163 A1 | 8/2015 | Amis et al. |
| 2015/0220883 A1 | 8/2015 | Bfar et al. |
| 2015/0230717 A1 | 8/2015 | Wan |
| 2015/0261918 A1 | 9/2015 | Thornbury, Jr. |
| 2015/0262499 A1 | 9/2015 | Wicka et al. |
| 2015/0286800 A1 | 10/2015 | Kanagala et al. |
| 2015/0287421 A1 | 10/2015 | Benway et al. |
| 2015/0288797 A1 | 10/2015 | Vincent |
| 2015/0288944 A1 | 10/2015 | Nistico et al. |
| 2015/0289823 A1 | 10/2015 | Rack-gomer et al. |
| 2015/0297134 A1 | 10/2015 | Albert et al. |
| 2015/0324751 A1 | 11/2015 | Orenstein et al. |
| 2015/0347690 A1 | 12/2015 | Keen et al. |
| 2015/0347711 A1 | 12/2015 | Soli et al. |
| 2015/0350799 A1 | 12/2015 | Schnaare et al. |
| 2015/0350861 A1 | 12/2015 | Soli et al. |
| 2016/0000379 A1 | 1/2016 | Pougatchev et al. |
| 2016/0019360 A1 | 1/2016 | Pahwa et al. |
| 2016/0055420 A1 | 2/2016 | Karanam et al. |
| 2016/0058313 A1 | 3/2016 | Sato |
| 2016/0058336 A1 | 3/2016 | Blahnik et al. |
| 2016/0058337 A1* | 3/2016 | Blahnik ............... A61B 5/7435 |
| 2016/0062540 A1 | 3/2016 | Yang et al. |
| 2016/0062572 A1 | 3/2016 | Yang et al. |
| 2016/0062582 A1 | 3/2016 | Wilson et al. |
| 2016/0063215 A1 | 3/2016 | Zamer |
| 2016/0066842 A1 | 3/2016 | Kokkoneva et al. |
| 2016/0085937 A1 | 3/2016 | Dettinger et al. |
| 2016/0086500 A1 | 3/2016 | Kaleal, III |
| 2016/0089569 A1 | 3/2016 | Blahnik |
| 2016/0098522 A1 | 4/2016 | Weinstein |
| 2016/0103985 A1 | 4/2016 | Shim et al. |
| 2016/0106398 A1 | 4/2016 | Kuppuswami |
| 2016/0109961 A1 | 4/2016 | Parshionikar |
| 2016/0132046 A1 | 5/2016 | Beoughter et al. |
| 2016/0135719 A1 | 5/2016 | Von Kraus et al. |

(56) References Cited

U.S. PATENT DOCUMENTS

| | | |
|---|---|---|
| 2016/0135731 A1 | 5/2016 | Drennan |
| 2016/0150978 A1 | 6/2016 | Yuen et al. |
| 2016/0166181 A1 | 6/2016 | Shennib |
| 2016/0166195 A1 | 6/2016 | Radecka et al. |
| 2016/0174857 A1 | 6/2016 | Eggers et al. |
| 2016/0180026 A1 | 6/2016 | Kim et al. |
| 2016/0189051 A1 | 6/2016 | Mahmood |
| 2016/0196635 A1 | 7/2016 | Cho et al. |
| 2016/0210099 A1 | 7/2016 | Hampapuram et al. |
| 2016/0235325 A1 | 8/2016 | Chou |
| 2016/0235374 A1 | 8/2016 | Miller et al. |
| 2016/0249857 A1 | 9/2016 | Choi et al. |
| 2016/0250517 A1 | 9/2016 | Tilvis et al. |
| 2016/0256082 A1 | 9/2016 | Ely et al. |
| 2016/0263435 A1 | 9/2016 | Venkatraman et al. |
| 2016/0270717 A1 | 9/2016 | Luna et al. |
| 2016/0270740 A1 | 9/2016 | Raisoni et al. |
| 2016/0275990 A1 | 9/2016 | Vassort |
| 2016/0285985 A1 | 9/2016 | Molettiere et al. |
| 2016/0287177 A1 | 10/2016 | Huppert et al. |
| 2016/0292373 A1 | 10/2016 | Spors et al. |
| 2016/0296210 A1 | 10/2016 | Matsushima |
| 2016/0299769 A1 | 10/2016 | Hunter et al. |
| 2016/0301761 A1 | 10/2016 | Sanchez-sandoval et al. |
| 2016/0301794 A1 | 10/2016 | Schlakman et al. |
| 2016/0302666 A1 | 10/2016 | Shaya |
| 2016/0313869 A1 | 10/2016 | Jang et al. |
| 2016/0314670 A1 | 10/2016 | Roberts et al. |
| 2016/0314683 A1 | 10/2016 | Felch et al. |
| 2016/0317341 A1 | 11/2016 | Galvan |
| 2016/0324457 A1 | 11/2016 | Dagum |
| 2016/0324488 A1 | 11/2016 | Olsen |
| 2016/0328991 A1 | 11/2016 | Simpson et al. |
| 2016/0332025 A1 | 11/2016 | Repka |
| 2016/0346607 A1 | 12/2016 | Rapfogel |
| 2016/0357616 A1 | 12/2016 | Yu et al. |
| 2016/0360100 A1 | 12/2016 | Kim et al. |
| 2016/0360972 A1 | 12/2016 | Kusakabe et al. |
| 2016/0367138 A1 | 12/2016 | Kim et al. |
| 2017/0000348 A1 | 1/2017 | Karsten et al. |
| 2017/0000359 A1 | 1/2017 | Kohli et al. |
| 2017/0007159 A1 | 1/2017 | Dieffenderfer et al. |
| 2017/0007167 A1 | 1/2017 | Kostic et al. |
| 2017/0032168 A1 | 2/2017 | Kim |
| 2017/0039327 A1 | 2/2017 | Bitran et al. |
| 2017/0042485 A1 | 2/2017 | Chung et al. |
| 2017/0043214 A1 | 2/2017 | Higashi |
| 2017/0046024 A1 | 2/2017 | Dascola et al. |
| 2017/0046052 A1 | 2/2017 | Lee et al. |
| 2017/0053542 A1 | 2/2017 | Wilson et al. |
| 2017/0070833 A1 | 3/2017 | Shennib |
| 2017/0071551 A1 | 3/2017 | Jain et al. |
| 2017/0075551 A1 | 3/2017 | Robinson et al. |
| 2017/0084196 A1 | 3/2017 | Nusbaum et al. |
| 2017/0086693 A1 | 3/2017 | Peterson et al. |
| 2017/0091567 A1 | 3/2017 | Wang et al. |
| 2017/0127997 A1 | 5/2017 | Hyde et al. |
| 2017/0132395 A1 | 5/2017 | Futch |
| 2017/0136297 A1 | 5/2017 | Penie |
| 2017/0147197 A1 | 5/2017 | Yang et al. |
| 2017/0150917 A1 | 6/2017 | Brief et al. |
| 2017/0156593 A1 | 6/2017 | Ferber et al. |
| 2017/0161014 A1 | 6/2017 | Kikugawa et al. |
| 2017/0172522 A1 | 6/2017 | Insler et al. |
| 2017/0177797 A1 | 6/2017 | Kurniawan et al. |
| 2017/0181645 A1 | 6/2017 | Mahalingam et al. |
| 2017/0181678 A1 | 6/2017 | Newberry |
| 2017/0188841 A1 | 7/2017 | Ma et al. |
| 2017/0188893 A1 | 7/2017 | Venkatraman et al. |
| 2017/0188979 A1 | 7/2017 | Volpe |
| 2017/0202496 A1 | 7/2017 | Ramanathan |
| 2017/0215811 A1 | 8/2017 | Newberry |
| 2017/0225034 A1 | 8/2017 | Kass et al. |
| 2017/0235443 A1 | 8/2017 | Suzuki |
| 2017/0237694 A1 | 8/2017 | Choudhary et al. |
| 2017/0243508 A1 | 8/2017 | Cheng et al. |
| 2017/0258455 A1 | 9/2017 | Qi |
| 2017/0274149 A1 | 9/2017 | Aeschlimann |
| 2017/0274267 A1 | 9/2017 | Blahnik |
| 2017/0287313 A1* | 10/2017 | Park .................. A61B 5/002 |
| 2017/0293727 A1 | 10/2017 | Klaassen et al. |
| 2017/0294174 A1 | 10/2017 | Albadawi et al. |
| 2017/0300186 A1 | 10/2017 | Kuhar et al. |
| 2017/0303844 A1 | 10/2017 | Baker et al. |
| 2017/0319184 A1 | 11/2017 | Sano |
| 2017/0329933 A1 | 11/2017 | Brust et al. |
| 2017/0330297 A1 | 11/2017 | Cronin et al. |
| 2017/0332980 A1 | 11/2017 | Fifield et al. |
| 2017/0348562 A1 | 12/2017 | Jung et al. |
| 2017/0354845 A1 | 12/2017 | Williams et al. |
| 2017/0357329 A1 | 12/2017 | Park et al. |
| 2017/0357520 A1 | 12/2017 | De Vries et al. |
| 2017/0364637 A1 | 12/2017 | Kshepakaran et al. |
| 2018/0000426 A1 | 1/2018 | Li |
| 2018/0001184 A1 | 1/2018 | Tran et al. |
| 2018/0011686 A1 | 1/2018 | Zhao et al. |
| 2018/0014121 A1 | 1/2018 | Lawrence et al. |
| 2018/0032234 A1 | 2/2018 | Michalske |
| 2018/0039410 A1 | 2/2018 | Kim et al. |
| 2018/0042540 A1 | 2/2018 | Kinnunen et al. |
| 2018/0042559 A1 | 2/2018 | Cabrera et al. |
| 2018/0047277 A1 | 2/2018 | Thyroff |
| 2018/0049659 A1 | 2/2018 | Briante et al. |
| 2018/0049696 A1 | 2/2018 | Eom et al. |
| 2018/0055490 A1 | 3/2018 | Lee et al. |
| 2018/0056130 A1 | 3/2018 | Bitran et al. |
| 2018/0060522 A1 | 3/2018 | Petterson et al. |
| 2018/0064356 A1 | 3/2018 | Mendenhall et al. |
| 2018/0064388 A1 | 3/2018 | Heneghan et al. |
| 2018/0065025 A1 | 3/2018 | Toda et al. |
| 2018/0070861 A1 | 3/2018 | Eastman et al. |
| 2018/0074462 A1 | 3/2018 | Helder et al. |
| 2018/0074464 A1 | 3/2018 | Essery et al. |
| 2018/0081918 A1 | 3/2018 | Gravenites et al. |
| 2018/0096739 A1 | 4/2018 | Sano |
| 2018/0107962 A1 | 4/2018 | Lundin et al. |
| 2018/0110465 A1 | 4/2018 | Naima |
| 2018/0117414 A1 | 5/2018 | Miyasaka et al. |
| 2018/0120985 A1 | 5/2018 | Wallace et al. |
| 2018/0122214 A1 | 5/2018 | Freedman et al. |
| 2018/0129994 A1 | 5/2018 | Fowler et al. |
| 2018/0132768 A1 | 5/2018 | Sasahara et al. |
| 2018/0137937 A1 | 5/2018 | Gass et al. |
| 2018/0140211 A1 | 5/2018 | Nakazawa et al. |
| 2018/0140927 A1 | 5/2018 | Kito et al. |
| 2018/0154212 A1 | 6/2018 | Park et al. |
| 2018/0189077 A1 | 7/2018 | Gupta et al. |
| 2018/0189343 A1 | 7/2018 | Embiricos et al. |
| 2018/0211020 A1 | 7/2018 | Fukuda |
| 2018/0226150 A1 | 8/2018 | Hayter et al. |
| 2018/0239869 A1 | 8/2018 | Laing et al. |
| 2018/0255159 A1 | 9/2018 | Cohen et al. |
| 2018/0256036 A1 | 9/2018 | Kogure et al. |
| 2018/0256078 A1 | 9/2018 | Vaterlaus |
| 2018/0256095 A1 | 9/2018 | Arnold et al. |
| 2018/0263510 A1 | 9/2018 | Cronin et al. |
| 2018/0263517 A1 | 9/2018 | Kubo |
| 2018/0279885 A1 | 10/2018 | Bulut |
| 2018/0329584 A1 | 11/2018 | Williams et al. |
| 2018/0336530 A1 | 11/2018 | Johnson et al. |
| 2018/0345078 A1 | 12/2018 | Blahnik et al. |
| 2018/0350451 A1 | 12/2018 | Ohnemus et al. |
| 2018/0368814 A1 | 12/2018 | R. Kudtarkar |
| 2018/0376107 A1 | 12/2018 | Shibaev et al. |
| 2019/0012898 A1* | 1/2019 | Wittrup .................. G08B 21/245 |
| 2019/0014205 A1 | 1/2019 | Miloseski et al. |
| 2019/0018588 A1 | 1/2019 | Debates et al. |
| 2019/0034050 A1 | 1/2019 | Williams et al. |
| 2019/0034494 A1 | 1/2019 | Bradley et al. |
| 2019/0043337 A1 | 2/2019 | Liu et al. |
| 2019/0073618 A1 | 3/2019 | Kanukurthy et al. |
| 2019/0090800 A1 | 3/2019 | Bosworth et al. |
| 2019/0090816 A1 | 3/2019 | Horseman |
| 2019/0104951 A1 | 4/2019 | Valys et al. |

(56) References Cited

U.S. PATENT DOCUMENTS

| | | |
|---|---|---|
| 2019/0108908 A1 | 4/2019 | Faulks et al. |
| 2019/0122523 A1 | 4/2019 | Roberts et al. |
| 2019/0138696 A1 | 5/2019 | Carpenter et al. |
| 2019/0150854 A1 | 5/2019 | Chung et al. |
| 2019/0192086 A1 | 6/2019 | Menon et al. |
| 2019/0206538 A1 | 7/2019 | Xing et al. |
| 2019/0223843 A1 | 7/2019 | Vitti |
| 2019/0228179 A1 | 7/2019 | Rakshit et al. |
| 2019/0228640 A1 | 7/2019 | Freedman et al. |
| 2019/0240534 A1 | 8/2019 | Black |
| 2019/0252054 A1 | 8/2019 | Dirani et al. |
| 2019/0274562 A1 | 9/2019 | Soli et al. |
| 2019/0274563 A1 | 9/2019 | Soli et al. |
| 2019/0274564 A1 | 9/2019 | Soli et al. |
| 2019/0274565 A1 | 9/2019 | Soli et al. |
| 2019/0278556 A1 | 9/2019 | Usher et al. |
| 2019/0298230 A1 | 10/2019 | Nicholson et al. |
| 2019/0302995 A1 | 10/2019 | Robinson et al. |
| 2019/0313180 A1 | 10/2019 | Kadiwala et al. |
| 2019/0333614 A1 | 10/2019 | Burger et al. |
| 2019/0336044 A1 | 11/2019 | Williams et al. |
| 2019/0336045 A1 | 11/2019 | Williams et al. |
| 2019/0339849 A1 | 11/2019 | Williams et al. |
| 2019/0341027 A1 | 11/2019 | Vescovi et al. |
| 2019/0365332 A1 | 12/2019 | Fedichev et al. |
| 2019/0380624 A1 | 12/2019 | Ota et al. |
| 2019/0385708 A1 | 12/2019 | Hong et al. |
| 2020/0000441 A1 | 1/2020 | Lafon et al. |
| 2020/0054931 A1 | 2/2020 | Martin et al. |
| 2020/0069258 A1 | 3/2020 | Grinberg |
| 2020/0100693 A1 | 4/2020 | Velo |
| 2020/0126673 A1 | 4/2020 | Tanabe et al. |
| 2020/0203012 A1 | 6/2020 | Kamath et al. |
| 2020/0214650 A1 | 7/2020 | Lee et al. |
| 2020/0245928 A1 | 8/2020 | Kang et al. |
| 2020/0261011 A1 | 8/2020 | Seppänen et al. |
| 2020/0273566 A1 | 8/2020 | Bhowmik et al. |
| 2020/0279472 A1* | 9/2020 | Chinikar ................ E03C 1/055 |
| 2020/0297249 A1 | 9/2020 | Williams et al. |
| 2020/0315544 A1 | 10/2020 | Levine |
| 2020/0323441 A1 | 10/2020 | Deno et al. |
| 2020/0350052 A1 | 11/2020 | Saint et al. |
| 2020/0356687 A1 | 11/2020 | Salzman et al. |
| 2020/0374682 A1 | 11/2020 | Newman et al. |
| 2020/0379611 A1 | 12/2020 | Dryer et al. |
| 2020/0381099 A1 | 12/2020 | Crowley et al. |
| 2020/0381123 A1 | 12/2020 | Dryer et al. |
| 2020/0382866 A1 | 12/2020 | Felton |
| 2020/0382867 A1 | 12/2020 | Felton |
| 2020/0384314 A1 | 12/2020 | Lee et al. |
| 2021/0019713 A1 | 1/2021 | Vangala et al. |
| 2021/0068714 A1 | 3/2021 | Crowley et al. |
| 2021/0113137 A1 | 4/2021 | Soli et al. |
| 2021/0204815 A1 | 7/2021 | Koskela et al. |
| 2021/0225482 A1 | 7/2021 | Crowley et al. |
| 2021/0257091 A1 | 8/2021 | Spang et al. |
| 2021/0287520 A1 | 9/2021 | Maeda et al. |
| 2021/0369130 A1 | 12/2021 | Felton et al. |
| 2021/0373746 A1 | 12/2021 | Felton et al. |
| 2021/0373747 A1 | 12/2021 | Felton et al. |
| 2021/0373748 A1 | 12/2021 | Felton et al. |
| 2021/0375450 A1 | 12/2021 | Felton et al. |
| 2021/0401378 A1 | 12/2021 | Pho et al. |
| 2022/0047250 A1 | 2/2022 | Clements et al. |
| 2022/0066902 A1 | 3/2022 | Narra et al. |
| 2022/0109932 A1 | 4/2022 | Felton et al. |
| 2022/0142515 A1 | 5/2022 | Crowley |
| 2022/0157143 A1 | 5/2022 | Panneer Selvam et al. |
| 2022/0160258 A1 | 5/2022 | Williams et al. |
| 2022/0273204 A1 | 9/2022 | Kamath et al. |
| 2023/0016144 A1 | 1/2023 | Dryer et al. |
| 2023/0020517 A1 | 1/2023 | Narra et al. |
| 2023/0101625 A1 | 3/2023 | Soli et al. |
| 2023/0114054 A1 | 4/2023 | Crowley et al. |
| 2024/0013889 A1 | 1/2024 | Crowley et al. |
| 2024/0050016 A1 | 2/2024 | Soli et al. |
| 2024/0053862 A1 | 2/2024 | Narra et al. |
| 2024/0079130 A1 | 3/2024 | Maratta et al. |

FOREIGN PATENT DOCUMENTS

| | | |
|---|---|---|
| CN | 103191557 A | 7/2013 |
| CN | 103250158 A | 8/2013 |
| CN | 103403627 A | 11/2013 |
| CN | 103474080 A | 12/2013 |
| CN | 103561640 A | 2/2014 |
| CN | 103927175 A | 7/2014 |
| CN | 103986813 A | 8/2014 |
| CN | 104584020 A | 4/2015 |
| CN | 104680459 A | 6/2015 |
| CN | 104720765 A | 6/2015 |
| CN | 105260078 A | 1/2016 |
| CN | 105283840 A | 1/2016 |
| CN | 105388998 A | 3/2016 |
| CN | 105632508 A | 6/2016 |
| CN | 105721667 A | 6/2016 |
| CN | 105980008 A | 9/2016 |
| CN | 106164808 A | 11/2016 |
| CN | 106371816 A | 2/2017 |
| CN | 106415559 A | 2/2017 |
| CN | 106537397 A | 3/2017 |
| CN | 106709235 A | 5/2017 |
| CN | 106725384 A | 5/2017 |
| CN | 106901720 A | 6/2017 |
| CN | 107278138 A | 10/2017 |
| CN | 107361755 A | 11/2017 |
| CN | 107454831 A | 12/2017 |
| CN | 107508995 A | 12/2017 |
| CN | 107591211 A | 1/2018 |
| CN | 107713981 A | 2/2018 |
| CN | 108604327 A | 9/2018 |
| CN | 109287140 A | 1/2019 |
| CN | 109670007 A | 4/2019 |
| CN | 111344796 A | 6/2020 |
| DE | 202017002874 U1 | 9/2017 |
| EP | 1077046 A1 | 2/2001 |
| EP | 2391004 A1 | 11/2011 |
| EP | 2568409 A1 | 3/2013 |
| EP | 2921899 A2 | 9/2015 |
| EP | 3042606 A1 | 7/2016 |
| EP | 3096235 A1 | 11/2016 |
| EP | 3101882 A2 | 12/2016 |
| EP | 3557590 A1 | 10/2019 |
| JP | 2004-80496 A | 3/2004 |
| JP | 2004-318503 A | 11/2004 |
| JP | 2005-79814 A | 3/2005 |
| JP | 2008-11865 A | 1/2008 |
| JP | 2009-232301 A | 10/2009 |
| JP | 2009-538571 A | 11/2009 |
| JP | 2010-517725 A | 5/2010 |
| JP | 2010-122901 A | 6/2010 |
| JP | 2010-162297 A | 7/2010 |
| JP | 2010-181280 A | 8/2010 |
| JP | 2011-197992 A | 10/2011 |
| JP | 2011-200575 A | 10/2011 |
| JP | 2012-502343 A | 1/2012 |
| JP | 2012-45373 A | 3/2012 |
| JP | 2012-174055 A | 9/2012 |
| JP | 2012-524640 A | 10/2012 |
| JP | 2012-239808 A | 12/2012 |
| JP | 2013-17631 A | 1/2013 |
| JP | 2013-192608 A | 9/2013 |
| JP | 2013-207323 A | 10/2013 |
| JP | 2013-544140 A | 12/2013 |
| JP | 2014-168685 A | 9/2014 |
| JP | 2015-28686 A | 2/2015 |
| JP | 2015-73590 A | 4/2015 |
| JP | 2015-213686 A | 12/2015 |
| JP | 2016-502875 A | 2/2016 |
| JP | 2016528016 A | 9/2016 |
| JP | 2016-177151 A | 10/2016 |
| JP | 2016-202751 A | 12/2016 |
| JP | 2016-538926 A | 12/2016 |
| JP | 2017-40981 A | 2/2017 |

(56) References Cited

FOREIGN PATENT DOCUMENTS

| | | |
|---|---|---|
| JP | 2017-117265 A | 6/2017 |
| JP | 2017-515520 A | 6/2017 |
| JP | 2017-134689 A | 8/2017 |
| JP | 2017-526073 A | 9/2017 |
| JP | 2017-182393 A | 10/2017 |
| JP | 2017-529880 A | 10/2017 |
| JP | 2017-211994 A | 11/2017 |
| JP | 2017-532069 A | 11/2017 |
| JP | 2018-504660 A | 2/2018 |
| JP | 6382433 B1 | 8/2018 |
| JP | 2018-191122 A | 11/2018 |
| JP | 2019-28806 A | 2/2019 |
| JP | 2019-32461 A | 2/2019 |
| JP | 2019-505035 A | 2/2019 |
| JP | 2019-36226 A | 3/2019 |
| JP | 2019-55076 A | 4/2019 |
| JP | 2019-207536 A | 12/2019 |
| JP | 2020-651 A | 1/2020 |
| JP | 2021-512429 A | 5/2021 |
| KR | 10-2002-0060421 A | 7/2002 |
| KR | 10-2008-0051460 A | 6/2008 |
| KR | 10-2012-0023657 A | 3/2012 |
| KR | 10-2013-0056646 A | 5/2013 |
| KR | 10-2013-0111569 A | 10/2013 |
| KR | 10-2013-0111570 A | 10/2013 |
| KR | 10-2015-0115385 A | 10/2015 |
| KR | 10-1594486 B1 | 2/2016 |
| KR | 10-2016-0028351 A | 3/2016 |
| KR | 10-2016-0076264 A | 6/2016 |
| KR | 10-2016-0077199 A | 7/2016 |
| KR | 10-2017-0003608 A | 1/2017 |
| KR | 10-2017-0019040 A | 2/2017 |
| KR | 10-2017-0019745 A | 2/2017 |
| KR | 10-2017-0029014 A | 3/2017 |
| KR | 10-2018-0129188 A | 12/2018 |
| KR | 10-2019-0094795 A | 8/2019 |
| WO | 2003/067202 A2 | 8/2003 |
| WO | 2006/046648 A1 | 5/2006 |
| WO | 2008/073359 A2 | 6/2008 |
| WO | 2009/095908 A2 | 8/2009 |
| WO | WO-2010028320 A1 * | 3/2010 ........... G08B 21/245 |
| WO | 2010/047035 A1 | 4/2010 |
| WO | 2010/126825 A1 | 11/2010 |
| WO | 2012/048832 A1 | 4/2012 |
| WO | 2012/060588 A2 | 5/2012 |
| WO | 2012/061438 A2 | 5/2012 |
| WO | 2012/061440 A2 | 5/2012 |
| WO | 2013/103570 A1 | 7/2013 |
| WO | 2013/109916 A1 | 7/2013 |
| WO | 2014/015378 A1 | 1/2014 |
| WO | 2014/033673 A1 | 3/2014 |
| WO | 2014/197339 A1 | 12/2014 |
| WO | 2014/207875 A1 | 12/2014 |
| WO | 2015/027133 A1 | 2/2015 |
| WO | 2015/084353 A1 | 6/2015 |
| WO | 2015/153803 A1 | 10/2015 |
| WO | 2015/164845 A1 | 10/2015 |
| WO | 2015/183828 A1 | 12/2015 |
| WO | 2015/187799 A1 | 12/2015 |
| WO | 2015/198488 A1 | 12/2015 |
| WO | 2016/036472 A1 | 3/2016 |
| WO | 2016/036582 A2 | 3/2016 |
| WO | 2016/151479 A1 | 9/2016 |
| WO | 2016/161152 A1 | 10/2016 |
| WO | 2016/164475 A1 | 10/2016 |
| WO | 2016/179559 A2 | 11/2016 |
| WO | 2016/207745 A1 | 12/2016 |
| WO | 2017/003045 A1 | 1/2017 |
| WO | 2017/037242 A1 | 3/2017 |
| WO | 2017/054277 A1 | 4/2017 |
| WO | 2017/062621 A1 | 4/2017 |
| WO | 2017/087642 A1 | 5/2017 |
| WO | 2017/090810 A1 | 6/2017 |
| WO | 2017/172046 A1 | 10/2017 |
| WO | 2017/213962 A1 | 12/2017 |
| WO | 2017/215203 A1 | 12/2017 |
| WO | 2018/132507 A1 | 7/2018 |
| WO | 2018/148356 A1 | 8/2018 |
| WO | 2018/213401 A1 | 11/2018 |
| WO | 2019/020977 A1 | 1/2019 |
| WO | 2019/099553 A1 | 5/2019 |
| WO | 2019/168956 A1 | 9/2019 |
| WO | 2019/177769 A1 | 9/2019 |
| WO | 2019/217005 A1 | 11/2019 |
| WO | 2019/236217 A1 | 12/2019 |
| WO | 2019/240513 A1 | 12/2019 |
| WO | 2021/011837 A1 | 1/2021 |
| WO | 2021/212112 A1 | 10/2021 |
| WO | WO-2021216291 A1 * | 10/2021 ........... A61B 5/0015 |
| WO | 2022/010573 A1 | 1/2022 |

OTHER PUBLICATIONS

Office Action received for Japanese Patent Application No. 2021-167557, mailed on Aug. 15, 2022, 5 pages (3 pages of English Translation and 2 pages of Official Copy).
Intention to Grant received for European Patent Application No. 20182116.2, mailed on Jun. 2, 2022, 8 pages.
Minutes of the Oral Proceedings received for European Patent Application No. 20182116.2, mailed on May 24, 2022, 7 pages.
Notice of Allowance received for Korean Patent Application No. 10-2022-7008569, mailed on May 19, 2022, 5 pages (2 pages of English Translation and 3 pages of Official Copy).
Office Action received for Chinese Patent Application No. 202011220489.5, mailed on Apr. 25, 2022, 15 pages (9 pages of English Translation and 6 pages of Official Copy).
Applicant-Initiated Interview Summary received for U.S. Appl. No. 17/031,723, mailed on Jan. 23, 2023, 4 pages.
Non-Final Office Action received for U.S. Appl. No. 17/952,053, mailed on Jan. 12, 2023, 12 pages.
Notice of Allowance received for U.S. Appl. No. 17/317,084, mailed on Jan. 6, 2023, 6 pages.
Office Action received for Australian Patent Application No. 2021261861, mailed on Jan. 12, 2023, 4 pages.
Office Action received for Australian Patent Application No. 2022202459, mailed on Jan. 6, 2023, 3 pages.
Supplemental Notice of Allowance received for U.S. Appl. No. 17/317,084, mailed on Jan. 19, 2023, 2 pages.
Advisory Action received for U.S. Appl. No. 17/031,779, mailed on Oct. 20, 2022, 5 pages.
Final Office Action received for U.S. Appl. No. 16/851,451, mailed on Oct. 20, 2022, 31 pages.
Office Action received for Australian Patent Application No. 2021261861, mailed on Oct. 14, 2022, 5 pages.
Office Action received for Chinese Patent Application No. 202010618240.3, mailed on Sep. 21, 2022, 16 pages (9 pages of English Translation and 7 pages of Official Copy).
Office Action received for Chinese Patent Application No. 202210004176.9, mailed on Sep. 28, 2022, 12 pages (6 pages of English Translation and 6 pages of Official Copy).
Office Action received for Danish Patent Application No. PA202070395, mailed on Oct. 7, 2022, 4 pages.
Supplemental Notice of Allowance received for U.S. Appl. No. 17/041,415, mailed on Oct. 13, 2022, 2 pages.
Applicant-Initiated Interview Summary received for U.S. Appl. No. 16/586,154, mailed on Sep. 3, 2021, 4 pages.
Applicant-Initiated Interview Summary received for U.S. Appl. No. 16/907,261, mailed on Jul. 16, 2021, 10 pages.
Applicant-Initiated Interview Summary received for U.S. Appl. No. 17/031,704, mailed on Feb. 9, 2021, 3 pages.
Applicant-Initiated Interview Summary received for U.S. Appl. No. 17/031,704, mailed on Jun. 25, 2021, 3 pages.
Applicant-Initiated Interview Summary received for U.S. Appl. No. 17/031,717, mailed on Jan. 29, 2021, 5 pages.
Applicant-Initiated Interview Summary received for U.S. Appl. No. 17/031,717, mailed on May 17, 2021, 5 pages.
Corrected Notice of Allowance received for U.S. Appl. No. 16/880,552, mailed on Jul. 7, 2021, 2 pages.

(56) References Cited

OTHER PUBLICATIONS

Corrected Notice of Allowance received for U.S. Appl. No. 16/921,312, mailed on Sep. 24, 2021, 2 pages.
Final Office Action received for U.S. Appl. No. 17/031,704, mailed on Apr. 1, 2021, 31 pages.
Final Office Action received for U.S. Appl. No. 17/031,717, mailed on Feb. 24, 2021, 23 pages.
Non-Final Office Action received for U.S. Appl. No. 17/031,704, mailed on Dec. 10, 2020, 30 pages.
Non-Final Office Action received for U.S. Appl. No. 17/031,717, mailed on Nov. 19, 2020, 22 pages.
Non-Final Office Action received for U.S. Appl. No. 17/031,717, mailed on Sep. 14, 2021, 35 pages.
Notice of Acceptance received for Australian Patent Application No. 2020256383, mailed on Aug. 3, 2021, 3 pages.
Notice of Allowance received for Japanese Patent Application No. 2020-153166, mailed on Sep. 13, 2021, 4 pages (1 page of English Translation and 3 pages of Official Copy).
Notice of Allowance received for Japanese Patent Application No. 2020-547369, mailed on Jul. 16, 2021, 4 pages (1 page of English Translation and 3 pages of Official Copy).
Notice of Allowance received for Korean Patent Application No. 10-2020-7026035, mailed on Aug. 23, 2021, 4 pages (2 pages of English Translation and 2 pages of Official Copy).
Notice of Allowance received for U.S. Appl. No. 16/138,809, mailed on Jul. 20, 2021, 6 pages.
Notice of Allowance received for U.S. Appl. No. 16/880,552, mailed on Jul. 23, 2021, 5 pages.
Notice of Allowance received for U.S. Appl. No. 16/907,261, mailed on Aug. 13, 2021, 8 pages.
Notice of Allowance received for U.S. Appl. No. 16/907,261, mailed on Sep. 28, 2021, 6 pages.
Notice of Allowance received for U.S. Appl. No. 16/921,312, mailed on Sep. 14, 2021, 9 pages.
Notice of Allowance received for U.S. Appl. No. 16/990,846, mailed on Sep. 22, 2021, 9 pages.
Notice of Allowance received for U.S. Appl. No. 17/031,704, mailed on Jul. 21, 2021, 10 pages.
Notice of Allowance received for U.S. Appl. No. 17/031,727, mailed on Dec. 24, 2020, 12 pages.
Notice of Allowance received for U.S. Appl. No. 17/031,727, mailed on Jun. 25, 2021, 6 pages.
Notice of Allowance received for U.S. Appl. No. 17/031,727, mailed on Mar. 12, 2021, 7 pages.
Office Action received for Australian Patent Application No. 2019234289, mailed on Jul. 20, 2021, 4 pages.
Office Action received for Australian Patent Application No. 2020239692, mailed on Jul. 20, 2021, 5 pages.
Office Action received for Australian Patent Application No. 2020239740, mailed on Jul. 9, 2021, 4 pages.
Office Action received for Chinese Patent Application No. 201910858933.7, mailed on Jun. 29, 2021, 8 pages (3 pages of English Translation and 5 pages of Official Copy).
Office Action received for Chinese Patent Application No. 202010618569.X, mailed on Sep. 7, 2021, 7 pages (4 pages of English Translation and 3 pages of Official Copy).
Office Action received for Danish Patent Application No. PA202070619, mailed on Aug. 27, 2021, 12 pages.
Office Action received for Japanese Patent Application No. 2020-153166, mailed on May 31, 2021, 6 pages (3 pages of English Translation and 3 pages of Official Copy).
Search Report and Opinion received for Danish Patent Application No. PA202070619, mailed on Dec. 2, 2020, 11 pages.
Summons to Attend Oral Proceedings received for European Patent Application No. 20180581.9, mailed on Aug. 18, 2021, 15 pages.
Summons to Attend Oral Proceedings received for European Patent Application No. 20180592.6, mailed on Aug. 11, 2021, 16 pages.
Supplemental Notice of Allowance received for U.S. Appl. No. 16/880,714, mailed on Sep. 16, 2021, 2 pages.
Supplemental Notice of Allowance received for U.S. Appl. No. 17/031,727, mailed on Jan. 15, 2021, 2 pages.
Advisory Action received for U.S. Appl. No. 16/144,864, mailed on Jul. 29, 2019, 6 pages.
Advisory Action received for U.S. Appl. No. 16/143,909, mailed on Nov. 7, 2019, 5 pages.
Advisory Action received for U.S. Appl. No. 16/143,997, mailed on Dec. 26, 2019, 7 pages.
Advisory Action received for U.S. Appl. No. 16/144,849, mailed on Aug. 12, 2019, 5 pages.
Advisory Action received for U.S. Appl. No. 16/144,864, mailed on Jul. 6, 2020, 6 pages.
Applicant Initiated Interview Summary received for U.S. Appl. No. 16/143,997, mailed on Aug. 13, 2020, 3 pages.
Applicant Initiated Interview Summary received for U.S. Appl. No. 16/144,849, mailed on Jan. 21, 2020, 6 pages.
Applicant Initiated Interview Summary received for U.S. Appl. No. 16/144,864, mailed on Apr. 29, 2020, 4 pages.
Applicant Initiated Interview Summary received for U.S. Appl. No. 16/586,154, mailed on Mar. 11, 2020, 4 pages.
Applicant Initiated Interview Summary received for U.S. Appl. No. 16/894,309, mailed on Jan. 26, 2021, 3 pages.
Applicant-Initiated Interview Summary received for U.S. Appl. No. 16/138,809, mailed on Dec. 16, 2020, 7 pages.
Applicant-Initiated Interview Summary received for U.S. Appl. No. 16/138,809, mailed on Jun. 9, 2020, 4 pages.
Applicant-Initiated Interview Summary received for U.S. Appl. No. 16/143,997, mailed on May 3, 2021, 4 pages.
Applicant-Initiated Interview Summary received for U.S. Appl. No. 16/144,864, mailed on Jun. 22, 2020, 3 pages.
Applicant-Initiated Interview Summary received for U.S. Appl. No. 16/584,186, mailed on Feb. 3, 2020, 4 pages.
Applicant-Initiated Interview Summary received for U.S. Appl. No. 16/586,154, mailed on Apr. 14, 2021, 4 pages.
Applicant-Initiated Interview Summary received for U.S. Appl. No. 16/586,154, mailed on Dec. 11, 2020, 5 pages.
Applicant-Initiated Interview Summary received for U.S. Appl. No. 16/880,552, mailed on Apr. 21, 2021, 3 pages.
Applicant-Initiated Interview Summary received for U.S. Appl. No. 16/880,552, mailed on Dec. 16, 2020, 6 pages.
Applicant-Initiated Interview Summary received for U.S. Appl. No. 16/880,552, mailed on Oct. 20, 2020, 6 pages.
Applicant-Initiated Interview Summary received for U.S. Appl. No. 16/880,714, mailed on Feb. 26, 2021, 5 pages.
Applicant-Initiated Interview Summary received for U.S. Appl. No. 16/894,309, mailed on Jun. 25, 2021, 4 pages.
Applicant-Initiated Interview Summary received for U.S. Appl. No. 16/907,261, mailed on Dec. 16, 2020, 6 pages.
Applicant-Initiated Interview Summary received for U.S. Appl. No. 16/907,261, mailed on Mar. 25, 2021, 2 pages.
Casella Cel Casella, "The Casella dBadge2—World's First Truly Wireless Noise Dosimeter and Airwave App!", Available online at: https://www.youtube.com/watch?v=Xvy2fl3cgYo, May 27, 2015, 3 pages.
Certificate of Examination received for Australian Patent Application No. 2019100222, mailed on Aug. 29, 2019, 2 pages.
Chatrzarrin Hanieh, "Feature Extraction for the Differentiation of Dry and Wet Cough Sounds", Carleton University, Sep. 2011, 144 pages.
CNET, "Google Fit's automatic activity tracking is getting smarter on Android Wear", Available online at: https://www.youtube.com/watch?v=IttzlCid_d8, May 18, 2016, 1 page.
Cook James, "German Period Tracking App Clue Has Over 2.5 Million Active Users—But It's Still Not Sure How It's Going to Make Money", Available online at: https://www.businessinsider.in/tech/german-period-tracking-app-clue-has-over-2-5-million-active-users-but-its-still-not-sure-how-its-going-to-make-money/articleshow/50511307.cms, Jan. 9, 2016, 9 pages.
Corrected Notice of Allowance received for U.S. Appl. No. 16/143,909, mailed on Feb. 20, 2020, 3 pages.
Corrected Notice of Allowance received for U.S. Appl. No. 16/143,909, mailed on Mar. 18, 2020, 3 pages.

(56) References Cited

OTHER PUBLICATIONS

Corrected Notice of Allowance received for U.S. Appl. No. 16/143,959, mailed on Dec. 13, 2019, 2 pages.
Corrected Notice of Allowance received for U.S. Appl. No. 16/143,997, mailed on Jul. 2, 2021, 2 pages.
Corrected Notice of Allowance received for U.S. Appl. No. 16/143,997, mailed on Jun. 4, 2021, 2 pages.
Corrected Notice of Allowance received for U.S. Appl. No. 16/584,186, mailed on Jul. 31, 2020, 2 pages.
Corrected Notice of Allowance received for U.S. Appl. No. 16/880,552, mailed on Dec. 23, 2020, 2 pages.
DC Rainmaker, "Garmin Fenix3 New Auto Climb Functionality", Available online at: https://www.youtube.com/watch?v=iuavOSNpVRc, Feb. 19, 2015, 1 page.
Decision on Appeal received for Korean Patent Application No. 10-2019-7025538, mailed on Feb. 24, 2021, 20 pages (4 pages of English Translation and 16 pages of Official Copy).
Decision to Grant received for Danish Patent Application No. PA201870379, mailed on Jul. 5, 2019, 2 pages.
Decision to Grant received for Danish Patent Application No. PA201870600, mailed on Oct. 17, 2019, 2 pages.
Decision to Grant received for Danish Patent Application No. PA201870601, mailed on Aug. 17, 2020, 2 pages.
Decision to Grant received for Danish Patent Application No. PA201870602, mailed on Aug. 18, 2020, 2 pages.
Epstein et al., "Examining Menstrual Tracking to Inform the Design of Personal Informatics Tools", Proceedings of the 2017 CHI Conference on Human Factors in Computing Systems, CHI '17, ACM Press, Denver, Co, USA, May 6-11, 2017, pp. 6876-6888.
European Search Report received for European Patent Application No. 20182116.2, mailed on Oct. 21, 2020, 4 pages.
Evergreen et al., "Bar Chart", Better Evaluation, Available online at: https://www.betterevaluation.org/en/evaluation-options/BarChart, Oct. 31, 2014, 8 pages.
Extended European Search Report received for European Patent Application No. 20180581.9, mailed on Aug. 12, 2020, 9 pages.
Extended European Search Report received for European Patent Application No. 20180592.6, mailed on Aug. 11, 2020, 10 pages.
Extended European Search Report received for European Patent Application No. 20203526.7, mailed on Jan. 29, 2021, 13 pages.
Final Office Action received for U.S. Appl. No. 16/138,809, mailed on Aug. 27, 2020, 24 pages.
Final Office Action received for U.S. Appl. No. 16/143,909, mailed on Aug. 28, 2019, 20 pages.
Final Office Action received for U.S. Appl. No. 16/143,997, mailed on Feb. 9, 2021, 16 pages.
Final Office Action received for U.S. Appl. No. 16/143,997, mailed on Sep. 30, 2019, 16 pages.
Final Office Action received for U.S. Appl. No. 16/144,030, mailed on Feb. 13, 2020, 11 pages.
Final Office Action received for U.S. Appl. No. 16/144,030, mailed on Oct. 1, 2019, 13 pages.
Final Office Action received for U.S. Appl. No. 16/144,849, mailed on Jun. 7, 2019, 29 pages.
Final Office Action received for U.S. Appl. No. 16/144,864, mailed on May 17, 2019, 24 pages.
Final Office Action received for U.S. Appl. No. 16/144,864, mailed on May 28, 2020, 29 pages.
Final Office Action received for U.S. Appl. No. 16/586,154, mailed on Jul. 6, 2020, 27 pages.
Final Office Action received for U.S. Appl. No. 16/586,154, mailed on May 24, 2021, 29 pages.
Final Office Action received for U.S. Appl. No. 16/894,309, mailed on Feb. 24, 2021, 30 pages.
Final Office Action received for U.S. Appl. No. 16/907,261, mailed on Mar. 18, 2021, 20 pages.
Fitbit App, Available online at: http://web.archive.org/web/20180114083150/https://www.fitbit.com/au/app, Jan. 14, 2018, 8 pages.

Garmin, "Fenix 5x Owner's Manual", Available online at: https://web.archive.org/web/20180127170640/https://static.garmin.com/pumac/fenix5x_OM_EN.pdf, Jan. 27, 2018, 42 pages.
Graphs and Charts, Available online at: https://www.teachervision.com/lesson-planning/graph-chart-teacher-resources, retrieved on Dec. 12, 2018, 4 pages.
Gupta Rajat, "Disable High vol. Warning (no root) in Samsung S7, S8 / Android 7.0", Available online at: https://www.youtube.com/watch?v=9fKwRBtk-x8, Retrieved on Nov. 26, 2020; esp. 2:04, Aug. 6, 2017, 1 page.
Haslam Oliver, "Stop Coronavirus in its Tracks by Using This Apple Watch App to Time Hand Washes", Available online at: https://www.imore.com/stop-coronavirus-its-tracks-using-apple-watch-app-time-hand-washes, Mar. 12, 2020, 12 pages.
Intention to Grant received for Danish Patent Application No. PA201870379, mailed on May 2, 2019, 2 pages.
Intention to Grant received for Danish Patent Application No. PA201870600, mailed on Jul. 10, 2019, 2 pages.
Intention to Grant received for Danish Patent Application No. PA201870601, mailed on Apr. 24, 2020, 2 pages.
Intention to Grant received for Danish Patent Application No. PA201870602, mailed on Apr. 24, 2020, 2 pages.
International Preliminary Report on Patentability received for PCT Patent Application No. PCT/US2019/019694, mailed on Sep. 24, 2020, 12 pages.
International Preliminary Report on Patentability received for PCT Patent Application No. PCT/US2019/024570, mailed on Nov. 19, 2020, 10 pages.
International Search Report and Written Opinion received for PCT Patent Application No. PCT/US2019/019694, mailed on Sep. 2, 2019, 17 pages.
International Search Report and Written Opinion received for PCT Patent Application No. PCT/US2019/024570, mailed on Aug. 8, 2019, 18 pages.
International Search Report and written Opinion received for PCT Patent Application No. PCT/US2020/025768, mailed on Aug. 10, 2020, 11 pages.
International Search Report and Written Opinion received for PCT Patent Application No. PCT/US2020/035164, mailed on Feb. 8, 2021, 26 pages.
International Search Report and Written Opinion received for PCT Patent Application No. PCT/US2020/035462, mailed on Sep. 11, 2020, 17 pages.
International Search Report and Written Opinion received for PCT Patent Application No. PCT/US2020/035474, mailed on Nov. 26, 2020, 16 pages.
International Search Report and Written Opinion received for PCT Patent Application No. PCT/US2020/042439, mailed on Oct. 9, 2020, 14 pages.
International Search Report and Written Opinion received for PCT Patent Application No. PCT/US2020/070280, mailed on Nov. 30, 2020, 20 pages.
Invitation to Pay Addition Fees received for PCT Patent Application No. PCT/US2020/035474, mailed on Oct. 2, 2020, 11 pages.
Invitation to Pay Additional Fees and Partial International Search Report received for PCT Patent Application No. PCT/US2020/035164, mailed on Oct. 16, 2020, 14 pages.
Invitation to Pay Additional Fees received for PCT Patent Application No. PCT/US2019/019694, mailed on Jul. 10, 2019, 12 pages.
Invitation to Pay Additional Fees received for PCT Patent Application No. PCT/US2020/070280, mailed on Oct. 7, 2020, 12 pages.
Invitation to Pay Search Fees received for European Patent Application No. 19726205.8, mailed on Feb. 14, 2020, 5 pages.
Liaqat et al., "Challenges with Real-World Smartwatch based Audio Monitoring", WearSys'18, Munich, Germany, Available online at: https://doi.org/10.1145/3211960.3211977, Jun. 10, 2018, 6 pages.
Lovejoy Ben, "Apple Watch blood sugar measurement coming in Series 7, claims report", Available online at: https://9to5mac.com/2021/01/25/apple-watch-blood-sugar-measurement/, Jan. 25, 2021, 6 pages.
Lyles Taylor, "Wear OS Smartwatches are Now Sending Reminders to Wash Your Hands", Available online at: https://www.theverge.

(56) References Cited

OTHER PUBLICATIONS com/2020/4/14/21221294/google-wear-os-smartwatches-reminders-wash-your-hands, Apr. 14, 2020, 2 pages.
Megadepot, "Casella dBadge2 Noise Dosimeter", Available online at: https://www.youtube.com/watch?v=pHiHLiYCD08, Jun. 12, 2018, 3 pages.
Moglia et al., "Evaluation of Smartphone Menstrual Cycle Tracking Applications Using an Adapted Applications Scoring System", Obstetrics and Gynecology, vol. 127. No. 6, Jun. 2016, pp. 1153-1160.
Multi-Set Bar Chart, The Data Visualization Catalogue, Available online at: https://datavizcatalogue.com/methods/multiset_barchart.html, Feb. 8, 2014, 3 pages.
Myflo App, "Functional Medicine Period Tracker and Hormone Balancing App", Available online at: https://web.archive.org/web/20170127104125/https://myflotracker.com/, Jan. 2017, 14 pages.
Myflo Tutorial, "How to change the start date of your current period", Available online at: https://www.youtube.com/watch?v=uQQ-odIBJB4, Jan. 23, 2017, 3 pages.
Myflo Tutorial, "Setting and changing the end date of your period", Available online at: https://www.youtube.com/watch?v=UvAA4OgqL3E, Jan. 23, 2017, 3 pages.
Non-Final Office Action Received for U.S. Appl. No. 16/144,864, mailed on Dec. 18, 2018, 19 pages.
Non-Final Office Action received for U.S. Appl. No. 16/138,809, mailed on Feb. 28, 2020, 22 pages.
Non-Final Office Action received for U.S. Appl. No. 16/143,909, mailed on Apr. 19, 2019, 16 pages.
Non-Final Office Action received for U.S. Appl. No. 16/143,959, mailed on Apr. 17, 2019, 15 pages.
Non-Final Office Action received for U.S. Appl. No. 16/143,997, mailed on Jul. 27, 2020, 15 pages.
Non-Final Office Action received for U.S. Appl. No. 16/143,997, mailed on May 21, 2019, 15 pages.
Non-Final Office Action received for U.S. Appl. No. 16/144,030, mailed on Apr. 12, 2019, 8 pages.
Non-Final Office Action received for U.S. Appl. No. 16/144,030, mailed on Nov. 5, 2020, 5 pages.
Non-Final Office Action received for U.S. Appl. No. 16/144,849, mailed on Dec. 31, 2018, 28 pages.
Non-Final Office Action received for U.S. Appl. No. 16/144,849, mailed on Sep. 17, 2019, 9 pages.
Non-Final Office Action received for U.S. Appl. No. 16/144,864, mailed on Jan. 31, 2020, 29 pages.
Non-Final Office Action received for U.S. Appl. No. 16/584,186, mailed on Dec. 6, 2019, 13 pages.
Non-Final Office Action received for U.S. Appl. No. 16/586,154, mailed on Dec. 9, 2019, 23 pages.
Non-Final Office Action received for U.S. Appl. No. 16/586,154, mailed on Dec. 28, 2020, 26 pages.
Non-Final Office Action received for U.S. Appl. No. 16/880,552, mailed on Feb. 19, 2021, 11 pages.
Non-Final Office Action received for U.S. Appl. No. 16/880,552, mailed on Jul. 23, 2020, 19 pages.
Non-Final Office Action received for U.S. Appl. No. 16/880,714, mailed on Oct. 28, 2020, 11 pages.
Non-Final Office Action received for U.S. Appl. No. 16/894,309, mailed on Oct. 15, 2020, 24 pages.
Non-Final Office Action received for U.S. Appl. No. 16/907,261, mailed on Sep. 30, 2020, 22 pages.
Non-Final Office Action received for U.S. Appl. No. 16/990,846, mailed on May 10, 2021, 16 pages.
Notice of Acceptance received for Australian Patent Application No. 2019222943, mailed on May 5, 2020, 3 pages.
Notice of Acceptance received for Australian Patent Application No. 2020204153, mailed on Jul. 6, 2020, 3 pages.
Notice of Allowance received for Chinese Patent Application No. 201910972529.2, mailed on Sep. 14, 2020, 6 pages (3 pages of English Translation and 3 pages of Official Copy).
Notice of Allowance received for Japanese Patent Application No. 2019-162293, mailed on Apr. 9, 2021, 4 pages (1 page of English Translation and 3 pages of Official Copy).
Notice of Allowance received for Japanese Patent Application No. 2020-104679, mailed on Jan. 4, 2021, 4 pages (1 page of English Translation and 3 pages of Official Copy).
Notice of Allowance received for Korean Patent Application No. 10-2019-7025538, mailed on Mar. 10, 2021, 5 pages (2 pages of English Translation and 3 pages of Official Copy).
Notice of Allowance received for Korean Patent Application No. 10-2020-7026391, mailed on May 11, 2021, 3 pages (1 page of English Translation and 2 pages of Official Copy).
Notice of Allowance received for Korean Patent Application No. 10-2020-7026453, mailed on May 11, 2021, 3 pages (1 page of English Translation and 2 pages of Official Copy).
Notice of Allowance received for U.S. Appl. No. 16/138,809, mailed on Apr. 16, 2021, 11 pages.
Notice of Allowance received for U.S. Appl. No. 16/143,909, mailed on Jan. 21, 2020, 9 pages.
Notice of Allowance received for U.S. Appl. No. 16/143,959, mailed on Oct. 31, 2019, 10 pages.
Notice of Allowance received for U.S. Appl. No. 16/143,997, mailed on May 13, 2021, 10 pages.
Notice of Allowance received for U.S. Appl. No. 16/144,030, mailed on Apr. 5, 2021, 8 pages.
Notice of Allowance received for U.S. Appl. No. 16/144,849, mailed on Apr. 17, 2020, 2 pages.
Notice of Allowance received for U.S. Appl. No. 16/144,849, mailed on Mar. 6, 2020, 9 pages.
Notice of Allowance received for U.S. Appl. No. 16/144,864, mailed on Feb. 9, 2021, 13 pages.
Notice of Allowance received for U.S. Appl. No. 16/144,864, mailed on Jul. 28, 2020, 27 pages.
Notice of Allowance received for U.S. Appl. No. 16/144,864, mailed on Mar. 12, 2021, 2 pages.
Notice of Allowance received for U.S. Appl. No. 16/144,864, mailed on Mar. 30, 2021, 2 pages.
Notice of Allowance received for U.S. Appl. No. 16/144,864, mailed on Sep. 10, 2020, 3 pages.
Notice of Allowance received for U.S. Appl. No. 16/144,864, mailed on Sep. 16, 2020, 2 pages.
Notice of Allowance received for U.S. Appl. No. 16/144,864, mailed on Sep. 29, 2020, 2 pages.
Notice of Allowance received for U.S. Appl. No. 16/584,186, mailed on Mar. 24, 2020, 10 pages.
Notice of Allowance received for U.S. Appl. No. 16/880,552, mailed on Dec. 1, 2020, 7 pages.
Notice of Allowance received for U.S. Appl. No. 16/880,552, mailed on May 12, 2021, 7 pages.
Notice of Allowance received for U.S. Appl. No. 16/880,714, mailed on Jun. 9, 2021, 6 pages.
Notice of Allowance received for U.S. Appl. No. 16/880,714, mailed on Mar. 19, 2021, 7 pages.
Office Action received for Australian Patent Application No. 2019100222, mailed on May 24, 2019, 6 pages.
Office Action received for Australian Patent Application No. 2019100495, mailed on Mar. 6, 2020, 3 pages.
Office Action received for Australian Patent Application No. 2019100495, mailed on Mar. 16, 2020, 3 pages.
Office Action received for Australian Patent Application No. 2019100495, mailed on Sep. 17, 2019, 7 pages.
Office Action received for Australian Patent Application No. 2019222943, mailed on Oct. 3, 2019, 3 pages.
Office Action received for Australian Patent Application No. 2019234289, mailed on Mar. 16, 2021, 8 pages.
Office Action received for Australian Patent Application No. 2019234289, mailed on Nov. 2, 2020, 6 pages.
Office Action received for Australian Patent Application No. 2020230340, mailed on Mar. 2, 2021, 6 pages.
Office Action received for Australian Patent Application No. 2020230340, mailed on May 27, 2021, 5 pages.
Office Action received for Australian Patent Application No. 2020230340, mailed on Nov. 2, 2020, 5 pages.

(56) References Cited

OTHER PUBLICATIONS

Office Action received for Australian Patent Application No. 2020256383, mailed on Jun. 4, 2021, 3 pages.
Office Action received for Chinese Patent Application No. 201910858933.7, mailed on Aug. 18, 2020, 14 pages (7 pages of English Translation and 7 pages of Official Copy).
Office Action received for Chinese Patent Application No. 201910972529.2, mailed on Jun. 28, 2020, 8 pages (1 page of English Translation and 7 pages of Official Copy).
Office Action received for Chinese Patent Application No. 202010606407.4, mailed on Jan. 27, 2021, 16 pages (7 pages of English Translation and 9 pages of Official Copy).
Office Action received for Chinese Patent Application No. 202010606407.4, mailed on Jun. 2, 2021, 12 pages (5 pages of English Translation and 7 pages of Official Copy).
Office Action received for Chinese Patent Application No. 202010618240.3, mailed on Mar. 29, 2021, 21 pages (11 pages of English Translation and 10 pages of Official Copy).
Office Action received for Chinese Patent Application No. 202010618569.X, mailed on Mar. 12, 2021, 14 pages (7 pages of English Translation and 7 pages of Official Copy).
Office Action received for Chinese Patent Application No. 202011220489.5, mailed on Jun. 1, 2021, 12 pages (6 pages of English Translation and 6 pages of Official Copy).
Office Action received for Danish Patent Application No. PA201870378, mailed on Feb. 25, 2019, 3 pages.
Office Action received for Danish Patent Application No. PA201870378, mailed on Jan. 6, 2020, 3 pages.
Office Action received for Danish Patent Application No. PA201870379, mailed on Feb. 28, 2019, 3 pages.
Office Action received for Danish Patent Application No. PA201870380, mailed on Mar. 27, 2019, 4 pages.
Office Action received for Danish Patent Application No. PA201870380, mailed on Mar. 5, 2020, 2 pages.
Office Action received for Danish Patent Application No. PA201870380, mailed on Sep. 11, 2018, 9 pages.
Office Action received for Danish Patent Application No. PA201870599, mailed on Dec. 20, 2019, 5 pages.
Office Action received for Danish Patent Application No. PA201870600, mailed on May 8, 2019, 3 pages.
Office Action received for Danish Patent Application No. PA201870601, mailed on Dec. 13, 2018, 8 pages.
Office Action received for Danish Patent Application No. PA201870601, mailed on Jan. 14, 2020, 3 pages.
Office Action received for Danish Patent Application No. PA201870601, mailed on Jun. 25, 2019, 3 pages.
Office Action received for Danish Patent Application No. PA201870602, mailed on Feb. 05, 2020, 3 pages.
Office Action received for Danish Patent Application No. PA201870602, mailed on Jun. 26, 2019, 3 pages.
Office Action received for Danish Patent Application No. PA201970534, mailed on Feb. 16, 2021, 2 pages.
Office Action received for Danish Patent Application No. PA201970534, mailed on Jun. 29, 2020, 2 pages.
Office Action received for Danish Patent Application No. PA202070335, mailed on Jun. 11, 2021, 4 pages.
Office Action received for Danish Patent Application No. PA202070620, mailed on May 10, 2021, 5 pages.
Office Action received for European Patent Application No. 19721883.7, mailed on Jan. 10, 2020, 4 pages.
Office Action received for European Patent Application No. 19721883.7, mailed on Jun. 15, 2021, 9 pages.
Office Action received for European Patent Application No. 19721883.7, mailed on May 28, 2020, 11 pages.
Office Action received for European Patent Application No. 19726205.8, mailed on Jun. 26, 2020, 9 pages.
Office Action received for European Patent Application No. 20180581.9, mailed on Apr. 1, 2021, 11 pages.
Office Action received for European Patent Application No. 20180592.6, mailed on Apr. 1, 2021, 11 pages.
Office Action received for European Patent Application No. 20182116.2, mailed on May 25, 2021, 9 pages.
Office Action received for European Patent Application No. 20182116.2, mailed on Nov. 6, 2020, 9 pages.
Office Action received for Japanese Patent Application No. 2018-184532, mailed on Mar. 1, 2021, 11 pages (6 pages of English Translation and 5 pages of Official Copy).
Office Action received for Japanese Patent Application No. 2019-162293, mailed on Jan. 31, 2020, 8 pages (4 pages of English Translation and 4 pages of Official Copy).
Office Action received for Japanese Patent Application No. 2019-162293, mailed on Jul. 27, 2020, 9 pages (5 pages of English Translation and 4 pages of Official Copy).
Office Action received for Japanese Patent Application No. 2020-104679, mailed on Sep. 18, 2020, 13 pages (7 pages of English Translation and 6 pages of Official Copy).
Office Action received for Japanese Patent Application No. 2020-547369, mailed on Apr. 9, 2021, 4 pages (2 pages of English Translation and 2 pages of Official Copy).
Office Action received for Korean Patent Application No. 10-2019-7025538, mailed on Aug. 15, 2020, 8 pages (4 pages of English Translation and 4 pages of Official Copy).
Office Action received for Korean Patent Application No. 10-2019-7025538, mailed on Feb. 17, 2020, 12 pages (6 pages of English Translation and 6 pages of Official Copy).
Office Action received for Korean Patent Application No. 10-2020-7026035, mailed on Feb. 19, 2021, 13 pages (6 pages of English Translation and 7 pages of Official Copy).
Office Action received for Korean Patent Application No. 10-2020-7026391, mailed on Jan. 27, 2021, 5 pages (2 pages of English Translation and 3 pages of Official Copy).
Office Action received for Korean Patent Application No. 10-2020-7026453, mailed on Jan. 27, 2021, 5 pages (2 pages of English Translation and 3 pages of Official Copy).
Peters Jay, "Samsung's Smartwatches Get a Hand-Washing Reminder and Timer App", Available online at: https://www.theverge.com/2020/4/17/21225205/samsung-smartwatch-galaxy-active-hand-washing-timer-reminder-app, Apr. 17, 2020, 2 pages.
Result of Consultation received for European Patent Application No. 19721883.7, mailed on Oct. 7, 2020, 3 pages.
Result of Consultation received for European Patent Application No. 19726205.8, mailed on Mar. 15, 2021, 19 pages.
Rizknows, "TomTom Multisport Cardio Review", Available online at: https://www.youtube.com/watch?v=WoVCzLrSN9A, Sep. 4, 2015, 1 page.
Schoon Ben, "Wear OS Now Sends a Reminder to Wash Your Hands Every Few Hours", Available online at: https://9to5google.com/2020/04/14/wear-os-wash-hands-reminder-coronavirus/, Apr. 14, 2020, 7 pages.
Search Report and Opinion received for Danish Patent Application No. PA201870378, mailed on Sep. 10, 2018, 9 pages.
Search Report and Opinion received for Danish Patent Application No. PA201870379, mailed on Sep. 14, 2018, 9 pages.
Search Report and Opinion received for Danish Patent Application No. PA201870599, mailed on Dec. 21, 2018, 9 pages.
Search Report and Opinion received for Danish Patent Application No. PA201870600, mailed on Jan. 31, 2019, 8 pages.
Search Report and Opinion received for Danish Patent Application No. PA201870602, mailed on Dec. 19, 2018, 8 pages.
Search Report and Opinion received for Danish Patent Application No. PA201970534, mailed on Sep. 23, 2019, 6 pages.
Search Report and Opinion received for Danish Patent Application No. PA202070335, mailed on Nov. 27, 2020, 10 pages.
Search Report and Opinion received for Danish Patent Application No. PA202070395, mailed on Nov. 24, 2020, 10 pages.
Search Report and Opinion received for Danish Patent Application No. PA202070620, mailed on Dec. 11, 2020, 9 pages.
Smith, "Garmin Fenix 5 Activity/Smart Watch Review", Available online at: https://www.youtube.com/watch?v=6PkQxXQxpoU, Sep. 2, 2017, 1 page.
Sportstechguides, "Garmin Fenix 5: How to Add Power Data Fields", Available online at: https://www.youtube.com/watch?v=ZkPptnnXEiQ, Apr. 29, 2017, 2 pages.

(56) References Cited

OTHER PUBLICATIONS

Sportstechguides, "Garmin Fenix 5: How To Set Up Run Alerts", Available online at: https://www.youtube.com/watch?v=gSMwv8vlhB4, May 13, 2017, 2 pages.
Studiosixdigital, "Dosimeter", Available online at: https://studiosixdigital.com/audiotools-modules-2/spl-modules/dosimeter.html, Mar. 3, 2017, 6 pages.
Summons to Attend Oral Proceedings received for European Patent Application No. 19726205.8, mailed on Oct. 29, 2020, 13 pages.
Supplemental Notice of Allowance received for U.S. Appl. No. 16/144,849, mailed on Mar. 31, 2020, 2 pages.
Suunto Spartan Trainer Wrist HR 1.12, Available online at: https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan-Heart Rate Zones", Available online at: https://www.youtube.com/watch?v=aixfoCnSOOU, Mar. 19, 2018, 2 pages.
Tech, Kalyani, "I See Some problems in Honor Band 5", Available online at: https://www.youtube.com/watch?v=5XPnYJFqajl, May 19, 2020, 1 page.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
Ticks, Smartwatch, "Senbono S10 IP67 Waterproof Multi-Function Blood Pressure Sports Smartwatch: One Minute Overview", Available online at: https://www.youtube.com/watch?v=rMxLJvKIVBs, Oct. 30, 2019, 1 page.
Tomtom, "TomTom Runner & Multi-Sport Reference Guide", Available online at: https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
Visual Pace Alarm app, Available online at: https://apps.garmin.com/en-US/apps/3940f3a2-4847-4078-a911-d77422966c82, Oct. 19, 2016, 1 page.
Wesley, "Apple Watch Series 1", Available online at: http://toolbox.info/blog/archives/1737-unknown.html, May 28, 2015, 5 pages (Official copy only). {See communication under Rule 37 CFR § 1.98(a) (3)}.
Youtube, "Apple Watch Series 3", Available online at: https://www.youtube.com/watch?v=iBPr9gEfkK8, Nov. 21, 2017, 15 pages (Official copy only). {See communication under Rule 37 CFR § 1.98(a) (3)}.
Zlelik, "Garmin Fenix 5 Open Water Swimming Activity Demo", Available online at: https://www.youtube.com/watch?v=iSVhdvw2dcs, Jun. 9, 2017, 1 page.
Applicant-Initiated Interview Summary received for U.S. Appl. No. 17/031,723, mailed on Mar. 21, 2021, 5 pages.
International Preliminary Report on Patentability received for PCT Patent Application No. PCT/US2020/070280, mailed on Mar. 17, 2022, 15 pages.
Non-Final Office Action received for U.S. Appl. No. 17/041,415, mailed on Mar. 29, 2022, 11 pages.
Notice of Allowance received for U.S. Appl. No. 17/031,717, mailed on Mar. 16, 2022, 12 pages.
Brief Communication Regarding Oral Proceedings received for European Patent Application No. 20182116.2, mailed on Apr. 13, 2022, 3 pages.
Corrected Notice of Allowance received for U.S. Appl. No. 17/031,717, mailed on Apr. 15, 2022, 3 pages.
Decision to Refuse received for European Patent Application No. 20180581.9, mailed on Apr. 13, 2022, 16 pages.
Intention to Grant received for European Patent Application No. 20180592.6, mailed on Apr. 20, 2022, 21 pages.
Minutes of the Oral Proceedings received for European Patent Application No. 20180581.9, mailed on Apr. 13, 2022, 10 pages.
Minutes of the Oral Proceedings received for European Patent Application No. 20180592.6, mailed on Apr. 7, 2022, 10 pages.
Non-Final Office Action received for U.S. Appl. No. 16/888,780, mailed on Apr. 20, 2022, 22 pages.
Notice of Acceptance received for Australian Patent Application No. 2020239692, mailed on Apr. 6, 2022, 3 pages.
Notice of Allowance received for Japanese Patent Application No. 2020-160023, mailed on Apr. 11, 2022, 4 pages (1 page of English Translation and 3 pages of Official Copy).
Notice of Allowance received for Japanese Patent Application No. 2021-571467, mailed on Apr. 11, 2022, 4 pages (1 page of English Translation and 3 pages of Official Copy).
Supplemental Notice of Allowance received for U.S. Appl. No. 16/894,309, mailed on Apr. 8, 2022, 3 pages.
Notice of Allowance received for Chinese Patent Application No. 202111611270.2, mailed on Sep. 21, 2022, 4 pages (1 page of English Translation and 3 pages of Official Copy).
Supplemental Notice of Allowance received for U.S. Appl. No. 17/041,415, mailed on Sep. 20, 2022, 2 pages.
Supplemental Notice of Allowance received for U.S. Appl. No. 17/317,084, mailed on Sep. 20, 2022, 2 pages.
Corrected Notice of Allowance received for U.S. Appl. No. 16/990,846, mailed on Feb. 9, 2022, 3 pages.
Non-Final Office Action received for U.S. Appl. No. 17/031,779, mailed on Feb. 16, 2022, 17 pages.
Office Action received for Australian Patent Application No. 2020239692, mailed on Jan. 27, 2022, 3 pages.
Office Action received for Chinese Patent Application No. 201910858933.7, mailed on Dec. 30, 2021, 9 pages (4 pages of English Translation and 5 pages of Official Copy).
Applicant-Initiated Interview Summary received for U.S. Appl. No. 16/851,451, mailed on Nov. 29, 2022, 4 pages.
Extended European Search Report received for European Patent Application No. 22190169.7, mailed on Nov. 23, 2022, 11 pages.
Final Office Action received for U.S. Appl. No. 16/888,780, mailed on Nov. 25, 2022, 10 pages.
Intention to Grant received for European Patent Application No. 20182116.2, mailed on Nov. 11, 2022, 9 pages.
Invitation to Pay Search Fees received for European Patent Application No. 20746438.9, mailed on Dec. 2, 2022, 4 pages.
Invitation to Pay Search Fees received for European Patent Application No. 20760607.0, mailed on Nov. 21, 2022, 3 pages.
Non-Final Office Action received for U.S. Appl. No. 17/031,723, mailed on Dec. 5, 2022, 27 pages.
Office Action received for Australian Patent Application No. 2021266294, mailed on Nov. 11, 2022, 3 pages.
Applicant-Initiated Interview Summary received for U.S. Appl. No. 16/851,451, mailed on Aug. 5, 2022, 3 pages.
Applicant-Initiated Interview Summary received for U.S. Appl. No. 16/888,780, mailed on Aug. 2, 2022, 4 pages.
Non-Final Office Action received for U.S. Appl. No. 16/953,781, mailed on Jul. 26, 2022, 9 pages.
Notice of Allowance received for Japanese Patent Application No. 2020-551585, mailed on Jul. 22, 2022, 4 pages (1 page of English Translation and 3 pages of Official Copy).
Office Action received for Korean Patent Application No. 10-2020-0124134, mailed on Jul. 28, 2022, 22 pages (11 pages of English Translation and 11 pages of Official Copy).
Notice of Allowance received for U.S. Appl. No. 16/880,552, mailed on Nov. 24, 2021, 5 pages.
Notice of Allowance received for U.S. Appl. No. 16/921,312, mailed on Nov. 29, 2021, 5 pages.
Office Action received for Danish Patent Application No. PA202070335, mailed on Nov. 17, 2021, 6 pages.
Office Action received for Danish Patent Application No. PA202070620, mailed on Nov. 19, 2021, 2 pages.
Office Action received for European Patent Application No. 20203526.7, mailed on Nov. 23, 2021, 9 pages.
Applicant-Initiated Interview Summary received for U.S. Appl. No. 17/031,723, mailed on Aug. 30, 2022, 4 pages.
Applicant-Initiated Interview Summary received for U.S. Appl. No. 17/031,779, mailed on Aug. 29, 2022, 2 pages.
Decision to Grant received for European Patent Application No. 20180592.6, mailed on Sep. 1, 2022, 3 pages.

(56) References Cited

OTHER PUBLICATIONS

Notice of Allowance received for U.S. Appl. No. 17/041,415, mailed on Aug. 31, 2022, 7 pages.
Notice of Allowance received for U.S. Appl. No. 17/317,084, mailed on Aug. 29, 2022, 10 pages.
Office Action received for Korean Patent Application No. 10-2020-7033395, mailed on Aug. 29, 2022, 11 pages (4 pages of English Translation and 7 pages of Official Copy).
Corrected Notice of Allowance received for U.S. Appl. No. 17/031,717, mailed on May 19, 2022, 3 pages.
Non-Final Office Action received for U.S. Appl. No. 16/851,451, mailed on May 9, 2022, 26 pages.
Notice of Acceptance received for Australian Patent Application No. 2020288147, mailed on Dec. 22, 2021, 3 pages.
Notice of Allowance received for Chinese Patent Application No. 202010618569.X, mailed on Jan. 7, 2022, 2 pages (1 page of English Translation and 1 page of Official Copy).
Notice of Allowance received for U.S. Appl. No. 16/990,846, mailed on Jan. 20, 2022, 6 pages.
Office Action received for Chinese Patent Application No. 202011220489.5, mailed on Dec. 1, 2021, 19 pages (11 pages of English Translation and 8 pages of Official Copy).
Office Action received for Japanese Patent Application No. 2020-551585, mailed on Jan. 6, 2022, 11 pages (5 pages of English Translation and 6 pages of Official Copy).
Brief Communication regarding Oral Proceedings received for European Patent Application No. 20180592.6, mailed on Dec. 21, 2021, 1 page.
Notice of Allowance received for Korean Patent Application No. 10-2021-7038005, mailed on Dec. 14, 2021, 4 pages (2 pages of English Translation and 2 pages of Official Copy).
Office Action received for Chinese Patent Application No. 202010606407.4, mailed on Nov. 18, 2021, 6 pages (3 pages of English Translation and 3 pages of Official Copy).
Office Action received for Chinese Patent Application No. 202010618240.3, mailed on Dec. 3, 2021, 23 pages (14 pages of English Translation and 9 pages of Official Copy).
Summons to Attend Oral Proceedings received for European Patent Application No. 20182116.2, mailed on Dec. 21, 2021, 7 pages.
Supplemental Notice of Allowance received for U.S. Appl. No. 16/894,309, mailed on Dec. 24, 2021, 2 pages.
Applicant-Initiated Interview Summary received for U.S. Appl. No. 17/031,717, mailed on Nov. 4, 2021, 5 pages.
Corrected Notice of Allowance received for U.S. Appl. No. 16/143,997, mailed on Nov. 16, 2021, 2 pages.
Notice of Allowance received for U.S. Appl. No. 16/894,309, mailed on Nov. 5, 2021, 12 pages.
Office Action received for Australian Patent Application No. 2019234289, mailed on Nov. 1, 2021, 4 pages.
Office Action received for Chinese Patent Application No. 202010618240.3, mailed on May 25, 2022, 20 pages (11 pages of English Translation and 9 pages of Official Copy).
Office Action received for Chinese Patent Application No. 202111611270.2, mailed on May 10, 2022, 16 pages (8 pages of English Translation and 8 pages of Official Copy).
International Search Report and Written Opinion received for PCT Patent Application No. PCT/US2021/035504, mailed on Sep. 16, 2021, 12 pages.
Notice of Allowance received for U.S. Appl. No. 16/143,997, mailed on Sep. 30, 2021, 8 pages.
Office Action received for Australian Patent Application No. 2020239740, mailed on Sep. 28, 2021, 5 pages.
Notice of Allowance received for U.S. Appl. No. 16/586,154, mailed on Oct. 15, 2021, 8 pages.
Office Action received for Australian Patent Application No. 2020230340, mailed on Oct. 11, 2021, 4 pages.
Brief Communication Regarding Oral Proceedings received for European Patent Application No. 20180581.9, mailed on Jan. 26, 2022, 1 page.
Brief Communication regarding Oral Proceedings received for European Patent Application No. 20180592.6, mailed on Jan. 26, 2022, 2 pages.
Intention to Grant received for Danish Patent Application No. PA202070619, mailed on Jan. 17, 2022, 2 pages.
International Preliminary Report on Patentability received for PCT Patent Application No. PCT/US2020/042439, mailed on Jan. 27, 2022, 10 pages.
Non-Final Office Action received for U.S. Appl. No. 17/031,723, mailed on Jan. 24, 2022, 17 pages.
Notice of Allowance received for Chinese Patent Application No. 202010606407.4, mailed on Jan. 24, 2022, 2 pages (1 page of English Translation and 1 page of Official Copy).
Notice of Allowance received for Japanese Patent Application No. 2018-184532, mailed on Jan. 17, 2022, 4 pages (1 page of English Translation and 3 pages of Official Copy).
Notice of Allowance received for Korean Patent Application No. 10-2021-7042504, mailed on Jan. 17, 2022, 6 pages (1 page of English Translation and 5 pages of Official Copy).
Office Action received for Japanese Patent Application No. 2020-160023, mailed on Jan. 17, 2022, 11 pages (06 pages of English Translation and 05 pages of Official Copy).
Result of Consultation received for European Patent Application No. 20180581.9, mailed on Jan. 21, 2022, 14 pages.
Result of Consultation received for European Patent Application No. 20180592.6, mailed on Jan. 26, 2022, 18 pages.
Supplemental Notice of Allowance received for U.S. Appl. No. 16/894,309, mailed on Jan. 25, 2022, 2 pages.
International Preliminary Report on Patentability received for PCT Patent Application No. PCT/US2021/035227, mailed on Dec. 15, 2022, 10 pages.
International Preliminary Report on Patentability received for PCT Patent Application No. PCT/US2021/035504, mailed on Dec. 15, 2022, 8 pages.
Office Action received for Australian Patent Application No. 2020313970, mailed on Dec. 22, 2022, 3 pages.
Brief Communication Regarding Oral Proceedings received for European Patent Application No. 20180581.9, mailed on Nov. 30, 2021, 1 page.
Corrected Notice of Allowance received for U.S. Appl. No. 16/880,552, mailed on Dec. 22, 2021, 2 pages.
Corrected Notice of Allowance received for U.S. Appl. No. 16/921,312, mailed on Dec. 7, 2021, 2 pages.
International Preliminary Report on Patentability received for PCT Patent Application No. PCT/US2020/035164, mailed on Dec. 16, 2021, 19 pages.
International Preliminary Report on Patentability received for PCT Patent Application No. PCT/US2020/035462, mailed on Dec. 16, 2021, 16 pages.
International Preliminary Report on Patentability received for PCT Patent Application No. PCT/US2020/025768, mailed on Dec. 16, 2021, 8 pages.
International Preliminary Report on Patentability received for PCT Patent Application No. PCT/US2020/035474, mailed on Dec. 16, 2021, 11 pages.
Office Action received for Danish Patent Application No. PA202070395, mailed on Dec. 15, 2021, 5 pages.
Office Action received for Indian Patent Application No. 202014041484, mailed on Dec. 8, 2021, 8 pages.
Corrected Notice of Allowance received for U.S. Appl. No. 16/143,997, mailed on Oct. 21, 2021, 2 pages.
Corrected Notice of Allowance received for U.S. Appl. No. 16/586,154, mailed on Oct. 27, 2021, 2 pages.
Corrected Notice of Allowance received for U.S. Appl. No. 17/031,704, mailed on Nov. 2, 2021, 7 pages.
International Search Report and Written Opinion received for PCT Patent Application No. PCT/US2021/035227, mailed on Oct. 6, 2021, 17 pages.
Office Action received for Danish Patent Application No. PA202070619, mailed on Oct. 14, 2021, 3 pages.
Applicant-Initiated Interview Summary received for U.S. Appl. No. 17/031,779, mailed on Mar. 10, 2022, 2 pages.

(56) References Cited

OTHER PUBLICATIONS

International Search Report and Written Opinion received for PCT Patent Application No. PCT/US2021/048568, mailed on Jan. 7, 2022, 14 pages.
Notice of Acceptance received for Australian Patent Application No. 2020239740, mailed on Feb. 22, 2022., 3 pages.
Notice of Allowance received for U.S. Appl. No. 16/894,309, mailed on Feb. 25, 2022, 9 pages.
Applicant-Initiated Interview Summary received for U.S. Appl. No. 16/953,781, mailed on Oct. 31, 2022, 12 pages.
Brief Communication Regarding Oral Proceedings received for European Patent Application No. 20746438.9, mailed on Nov. 7, 2022, 1 page.
Notice of Allowance received for U.S. Appl. No. 16/953,781, mailed on Nov. 9, 2022, 7 pages.
Office Action received for European Patent Application No. 20746438.9, mailed on Oct. 31, 2022, 7 pages.
Applicant-Initiated Interview Summary received for U.S. Appl. No. 17/041,415, mailed on Jun. 29, 2022, 2 pages.
Final Office Action received for U.S. Appl. No. 17/031,723, mailed on Jul. 12, 2022, 25 pages.
Final Office Action received for U.S. Appl. No. 17/031,779, mailed on Jul. 14, 2022, 19 pages.
Notice of Allowance received for U.S. Appl. No. 17/031,717, mailed on Jul. 7, 2022, 12 pages.
Summons to Attend Oral Proceedings received for European Patent Application No. 20203526.7, mailed on Jun. 23, 2022, 9 pages.
International Preliminary Report on Patentability received for PCT Patent Application No. PCT/US2021/048568, mailed on Mar. 9, 2023, 11 pages.
Non-Final Office Action received for U.S. Appl. No. 16/851,451, mailed on Feb. 24, 2023, 28 pages.
Notice of Allowance received for U.S. Appl. No. 16/953,781, mailed on Feb. 27, 2023, 5 pages.
Office Action received for Australian Patent Application No. 2022204568, mailed on Mar. 11, 2023, 4 pages.
Applicant-Initiated Interview Summary received for U.S. Appl. No. 17/952,053, mailed on Apr. 5, 2023, 6 pages.
Corrected Notice of Allowance received for U.S. Appl. No. 16/953,781, mailed on Mar. 30, 2023, 2 pages.
Non-Final Office Action received for U.S. Appl. No. 17/952,182, mailed on Mar. 28, 2023, 9 pages.
Office Action received for Australian Patent Application No. 2020313970, mailed on Mar. 22, 2023, 4 pages.
Office Action received for Australian Patent Application No. 2022202459, mailed on Mar. 27, 2023, 5 pages.
Office Action received for Danish Patent Application No. PA202070395, mailed on Mar. 31, 2023, 3 pages.
Office Action received for Japanese Patent Application No. 2022-502594, mailed on Mar. 20, 2023, 10 pages (5 pages of English Translation and 5 pages of Official Copy).
Office Action received for Korean Patent Application No. 10-2020-0124134, mailed on Mar. 28, 2023, 9 pages (4 pages of English Translation and 5 pages of Official Copy).
Notice of Allowance received for Japanese Patent Application No. 2021-167557, mailed on Jan. 27, 2023, 4 pages (1 page of English Translation and 3 pages of Official Copy).
Notice of Allowance received for U.S. Appl. No. 17/031,779, mailed on Feb. 1, 2023, 11 pages.
Office Action received for European Patent Application No. 20746438.9, mailed on Feb. 1, 2023, 9 pages.
Office Action received for European Patent Application No. 20760607.0, mailed on Feb. 1, 2023, 13 pages.
Corrected Notice of Allowance received for U.S. Appl. No. 17/135,710, mailed on Aug. 18, 2023, 4 pages.
Non-Final Office Action received for U.S. Appl. No. 16/888,780, mailed on Aug. 17, 2023, 12 pages.
Office Action received for European Patent Application No. 20760607.0, mailed on Aug. 17, 2023, 7 pages.
Final Office Action received for U.S. Appl. No. 16/851,451, mailed on Jun. 1, 2023, 35 pages.
Non-Final Office Action received for U.S. Appl. No. 17/031,723, mailed on Jun. 2, 2023, 23 pages.
Notice of Allowance received for U.S. Appl. No. 17/031,779, mailed on May 26, 2023, 9 pages.
Office Action received for Australian Patent Application No. 2022203508, mailed on May 19, 2023, 2 pages.
Office Action received for Australian Patent Application No. 2022204568, mailed on May 22, 2023, 4 pages.
Notice of Acceptance received for Australian Patent Application No. 2022204568, mailed on Jul. 27, 2023, 3 pages.
Notice of Allowance received for U.S. Appl. No. 17/135,710, mailed on Jul. 27, 2023, 9 pages.
Office Action received for Japanese Patent Application No. 2022-078280, mailed on Jul. 24, 2023, 8 pages (4 pages of English Translation and 4 pages of Official Copy).
Applicant-Initiated Interview Summary received for U.S. Appl. No. 16/851,451, mailed on Apr. 20, 2023, 4 pages.
Notice of Allowance received for U.S. Appl. No. 17/952,053, mailed on Apr. 17, 2023, 6 pages.
Office Action received for Chinese Patent Application No. 202210004176.9, mailed on Feb. 19, 2023, 23 pages (14 pages of English Translation and 9 pages of Official Copy).
Notice of Allowance received for Japanese Patent Application No. 2022-502594, mailed on Jul. 7, 2023, 4 pages (1 page of English Translation and 3 pages of Official Copy).
Office Action received for Danish Patent Application No. PA202070395, mailed on Jul. 5, 2023, 6 pages.
Office Action received for European Patent Application No. 20746438.9, mailed on Jul. 4, 2023, 7 pages.
Applicant-Initiated Interview Summary received for U.S. Appl. No. 17/031,723, mailed on Jun. 22, 2023, 2 pages.
Notice of Acceptance received for Australian Patent Application No. 2020313970, mailed on Jun. 22, 2023, 3 pages.
Notice of Acceptance received for Australian Patent Application No. 2022203508, mailed on Jun. 27, 2023, 3 pages.
Office Action received for Korean Patent Application No. 10-2020-0124134, mailed on Jun. 23, 2023, 8 pages (4 pages of English Translation and 4 pages of Official Copy).
Notice of Acceptance received for Australian Patent Application No. 2022202459, mailed on May 11, 2023, 3 pages.
Notice of Allowance received for U.S. Appl. No. 18/078,444, mailed on May 12, 2023, 9 pages.
Office Action received for Australian Patent Application No. 2021261861, mailed on May 3, 2023, 4 pages.
Office Action received for German Patent Application No. 112020002566.7, mailed on Mar. 24, 2023, 32 pages (14 pages of English Translation and 18 pages of official copy).
Levy et al., "A good little tool to get to know yourself a bit better", a qualitative study on users' experiences of app-supported menstrual tracking in Europe., In: BMC Public Health, vol. 19, 2019, pp. 1-11.
Corrected Notice of Allowance received for U.S. Appl. No. 17/031,779, mailed on Jun. 14, 2023, 2 pages.
Office Action received for Chinese Patent Application No. 202210004176.9, mailed on Apr. 28, 2023, 12 pages (6 pages of English Translation and 6 pages of Official Copy).
Office Action received for Indian Patent Application No. 202215032692, mailed on Jun. 15, 2023, 3 pages.
Office Action received for Japanese Patent Application No. 2022-078277, mailed on Jun. 9, 2023, 11 pages (6 pages of English Translation and 5 pages of Official Copy).
Supplemental Notice of Allowance received for U.S. Appl. No. 18/078,444, mailed on Jun. 15, 2023, 2 pages.
Notice of Allowance received for Japanese Patent Application No. 2022-078280, mailed on Sep. 4, 2023, 4 pages (1 page of English Translation and 3 pages of Official Copy).
Notice of Allowance received for U.S. Appl. No. 18/078,444, mailed on Aug. 31, 2023, 6 pages.
Office Action received for Australian Patent Application No. 2023212604, mailed on Sep. 4, 2023, 3 pages.

(56) References Cited

OTHER PUBLICATIONS

Corrected Notice of Allowance received for U.S. Appl. No. 16/851,451, mailed on Feb. 20, 2024, 3 pages.
Notice of Allowance received for U.S. Appl. No. 17/135,710, mailed on Feb. 14, 2024, 4 pages.
Office Action received for Indian Patent Application No. 202315061713, mailed on Feb. 14, 2024, 8 pages.
Office Action received for Indian Patent Application No. 202315061718, mailed on Feb. 14, 2024, 8 pages.
Final Office Action received for U.S. Appl. No. 16/888,780, mailed on Feb. 29, 2024, 12 pages.
Notice of Allowance received for Japanese Patent Application No. 2022-573764, mailed on Feb. 26, 2024, 4 pages (1 page of English Translation and 3 pages of Official Copy).
Office Action received for Chinese Patent Application No. 202180053264.1, mailed on Jan. 18, 2024, 14 pages (8 pages of English Translation and 6 pages of Official Copy).
Final Office Action received for U.S. Appl. No. 17/952,182, mailed on Jan. 4, 2024, 9 pages.
Office Action received for European Patent Application No. 20760607.0. mailed on Jan. 3, 20,24, 7 pages.
Office Action received for Japanese Patent Apptication No. 2022-573764, mailed on Dec. 25, 2023, 8 pages (4 pages of Engiish Translation and 4 pages of Official Copy).
Corrected Notice of Allowance received for U.S. Appl. No. 17/952,053, mailed on Jan. 25, 2024, 6 pages.
Non-Final Office Action received for U.S. Appl. No. 17/554,678, mailed on Feb. 1, 2024, 10 pages.
Notice of Allowance received for U.S. Appl. No. 16/851,451, mailed on Jan. 31, 2024, 13 pages.
Office Action received for Korean Patent Application No. 10-2023-7018399, mailed on Jan. 24, 2024, 11 pages (4 pages of English Translation and 7 pages of Official Copy).
Final Office Action received for U.S. Appl. No. 17/584,190, mailed on Mar. 13, 2024, 20 pages.
Intention to Grant received for European Patent Application No. 20746438.9, mailed on Mar. 21, 2024, 15 pages.
International Search Report and Written Opinion received for PCT Patent Application No. PCT/US2023/031421, mailed on Feb. 9, 2024, 22 pages.
Invitation to Pay Additional Fees and Partial International Search Report received for PCT Patent Application No. PCT/US2023/031421, mailed on Dec. 1, 2023, 10 pages.
Office Action received for Australian Patent Application No. 2021283914, mailed on Mar. 14, 2024, 5 pages.
Applicant Initiated Interview Summary received for U.S. Appl. No. 16/888,780, mailed on Dec. 14, 2023, 3 pages.
Applicant Initiated Interview Summary received for U.S. Appl. No. 17/031,723, mailed on Oct. 31, 2023, 4 pages.
Applicant Initiated Interview Summary received for U.S. Appl. No. 17/584,190, mailed on Dec. 4, 2023, 5 pages.
Decision on Appeal received for Korean Patent Application No. 10-2020-0124134, mailed on Oct. 20, 2023, 24 pages (4 pages of English Translation and 20 pages of Official Copy).
Final Office Action received for U.S. Appl. No. 17/031,723, rnailed on Oct. 4, 2023, 13 pages.
Hardwick Tim, "AliveCor 'Kardia Band' Medical Grade EKG Analyzer for Apple Watch Receives FDA Approvai", MacRumors, Available online at: https://www.macromors.com/2017/11/30/Alivecor-kardia-ekg-band-medical-fda-apple-watch/, Nov/ 30, 2017, 3 pages.
Karbia by Alivecor, "How to Record a Clean EKG With Kardiaband", Available Online at: https://www.youtube.com/watch?v=_Vlc9VE6VO4&t=2s. Nov. 30, 2017, 2 pages.
Luo et al., "Detection and Prediction of Ovulation from Body Temperature Measured by an In-Ear Wearable Thermometer", IEEE Transactions on Biomedicai Engineering, Available online at:10.1109/TBME.2019.2916823, vol. 67, No. 2, May 15, 2019, pp. 512-522.
Non-Final Office Action received for U.S. Appl. No. 17/584,190, mailed on Oct. 5, 2023, 17 pages.
Notice of Acceptance received for Australian Patent Application No. 2023212504, mailed on Oct. 12, 2023, 3 pages.
Notice of Allowance received for Japanese Patent Application No. 2022-078277, mailed on Oct. 27, 2023, 4 pages (1 page of Engiish Translation and 3 pages of Official Copy).
Notice of Allowance received for Japanese Patent Application No. 2022-131993, mailed on Dec. 18, 2023, 4 pages (1 page of English Translation and 3 pages of Official Copy).
Notice of Allowance received for Korean Patent Appiication No. 10-2020-0124134, mailed on Nov. 21, 2023, 8 pages (2 pages of English Transiation and 6 pages of Official Copy).
Official Notice of Allowance received for U.S. Appl. No. 17/135,710, mailed on Nov. 6, 2023, 7 pages.
Office Action received for Australian Patent Application No. 2021261861, mailed on Sep. 22, 2023, 5 pages.
Office Action received for Australian Patent Application 2021283914, mailed on Sep. 25, 2023, 5 pages.
Office Action received for Chinese Patent Application No. 202180053264.1, mailed on Sep. 23, 2023. 17 pages (9 pages of English Translation and 8 pages of Official Copy).
Office Action received for Danish Patent Application No. PA202070395, mailed on Nov. 3, 2023, 3 pages.
Office Action received for European Patent Application No. 20746438.9, mailed on Oct. 31, 2023, 9 pages.
Office Action received for European Patent Application No. 20751022.3, mailed on Oct. 19, 2023, 8 pages.
Office Action received for European Patent Application No. 20753659.0, mailed on Oct. 26, 2023, 9 pages.
Office Action received for Japanese Patent Application No. 2022-131993, mailed on Sep. 15, 2023, 6 pages (3 pages of English Translation and 3 pages of Official Copy).
Office Action received for Korean Patent Application No. 10-2022-7012608, mailed on Dec. 5, 2023, 12 pages (5 pages of English Translation and 7 pages of Official Copy).
Prasad et al., "Understanding Sharing Preferences and Behavior for Mhealth Devices", Proceedings of the 2012 ACM workshop on Privacy in the electronic society, Available online at: https://dl.acm.org/doi/10.1145/2381966.2381983, Oct. 15, 2012, pp. 117-128.
Supplemental Notice of Allowance received for U.S. Appl. No. 18/078,444, mailed on Oct. 16, 2023, 4 pages.
Notice of Allowance received for U.S. Appl. No. 17/135,710, mailed on Jan. 23, 2024, 7 pages.
Office Action received for Australian Patent Application No. 2021283914, mailed on Dec. 13, 2023, 5 pages.
Extended European Search Report received for European Patent Application No. 23200361.6, mailed on Mar. 28, 2024, 10 pages.
Office Action received for Japanese Patent Application No. 2023-028769, mailed on Apr. 1, 2024, 8 pages (4 pages of English Translation and 4 pages of Official Copy).
Applicant-Initiated Interview Summary received for U.S. Appl. No. 17/554,678, mailed on Apr. 23, 2024, 4 pages.
Office Action received for Chinese Patent Application No. 202210346306.7, mailed on Apr. 10, 2024, 18 pages (10 pages of English Translation and 8 pages of Official Copy).
Office Action received for European Patent Application No. 21787524.4, mailed on Apr. 12, 2024, 10 pages.
Applicant-Initiated Interview Summary received for U.S. Appl. No. 17/584,190, mailed on May 29, 2024, 5 pages.
Office Action received for Korean Patent Application No. 10-2021-7020689, mailed on May 14, 2024, 13 pages (6 pages of English Translation and 7 pages of Official Copy).
Final Office Action received for U.S. Appl. No. 17/952,182, mailed on Jun. 6, 2024, 12 pages.
Notice of Allowance received for U.S. Appl. No. 17/584,190, mailed on Jun. 20, 2024, 9 pages.
Notice of Allowance received for U.S. Appl. No. 18/222,386, mailed on Jun. 24, 2024, 13 pages.
Summons to Oral Proceedings received for European Patent Application No. 20180581.9, mailed on Jun. 25, 2024, 4 pages.
Office Action received for Australian Patent Application No. 2021283914, mailed on Aug. 9, 2024, 6 pages.

* cited by examiner

716
In response to detecting that the set of one or more termination criteria has been met:

718
In accordance with a determination that the set of one or more termination criteria was met based on the physical activity of the first type having continued for at least the respective duration, output, via the one or more perceptual output generation components, a second perceptual feedback indicating that the physical activity of the first type was detected for the respective duration

720
In accordance with a determination that the termination criteria has been met because the physical activity of the first type stopped before the timer reached the respective duration, providing a third perceptual feedback indicating that the physical activity of the first type is no longer being detected

722
In accordance with a determination that the physical activity of the first type is not detected via the one or more sensors within a second respective duration after providing the third perceptual feedback, provide a fourth perceptual feedback indicating that the physical of the first type was not performed for the duration of the timer

724
The third perceptual feedback is a prompt to continue the physical activity of the first type

*FIG. 7B*

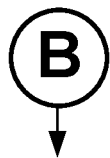

726
Detect that a set of prompting criteria has been met, wherein the set of prompting criteria includes a criterion that is met when the location of the computer system corresponds to a predefined location.

728
In response to detecting that the set of prompting criteria has been met, output a first prompt for the user of the computer system to perform the physical activity of the first type.

*FIG. 7C*

USER INTERFACES FOR TRACKING OF PHYSICAL ACTIVITY EVENTS

CROSS-REFERENCE TO RELATED APPLICATIONS

This application claims priority to U.S. Provisional Patent Application No. 63/033,814, entitled "USER INTERFACES FOR TRACKING OF PHYSICAL ACTIVITY EVENTS", filed Jun. 2, 2020, the entire contents of which is hereby incorporated by reference.

This application is related to U.S. Provisional Patent Application No. 62/891,944, entitled "METHODS AND APPARATUS FOR DETECTING INDIVIDUAL HEALTH RELATED EVENTS", filed Aug. 26, 2019, and U.S. patent application Ser. No. 16/994,524, entitled "METHODS AND APPARATUS FOR DETECTING INDIVIDUAL HEALTH RELATED EVENTS", filed Aug. 14, 2020 and published as U.S. Publication No. 2021-0063434 (A1) on Mar. 4, 2021, all of which are hereby incorporated by reference in their entirety for any and all purposes, including, but not limited to FIGS. 1-6, and the accompanying disclosure.

FIELD

The present disclosure relates generally to computer user interfaces, and more specifically to techniques for tracking the performance of a physical activity event.

BACKGROUND

Computer systems can include applications for tracking physical activities. Such systems can include and employ sensors for such tracking.

BRIEF SUMMARY

Some techniques for tracking the performance of a physical activity event using electronic devices, are generally cumbersome and inefficient. For example, some techniques use a complex and time-consuming user interface, which may include multiple key presses or keystrokes. Such techniques require more time than necessary, wasting user time and device energy. This latter consideration is particularly important in battery-operated devices.

Accordingly, the present technique provides electronic devices with faster, more efficient methods and interfaces for tracking the performance of a physical activity event. Such methods and interfaces optionally complement or replace other methods for tracking the performance of a physical activity event. Such methods and interfaces reduce the cognitive burden on a user and produce a more efficient human-machine interface. For battery-operated computing devices, such methods and interfaces conserve power and increase the time between battery charges.

In accordance with some embodiments, a method, performed at a computer system that is in communication with one or more perceptual output generation components and one or more sensors is described. The method includes: detecting, via the one or more sensors, a first set of sensor data that corresponds to a user of the computer system starting a physical activity of a first type; in response to detecting the first set of sensor data that corresponds to the user of the computer system starting the physical activity of the first type: starting a timer of a respective duration, and outputting, via the one or more perceptual output generation components, a first perceptual feedback indicating that the timer of the respective duration is operating; after starting the first timer: in accordance with a determination that the physical activity of the first type is ongoing, continuing to output the first perceptual feedback indicating that the timer of the respective duration is operating; and detecting that a set of one or more termination criteria has been met; and in response to detecting that the set of one or more termination criteria has been met: in accordance with a determination that the set of one or more termination criteria was met based on the physical activity of the first type having continued for at least the respective duration, outputting, via the one or more perceptual output generation components, a second perceptual feedback indicating that the physical activity of the first type was detected for the respective duration.

In accordance with some embodiments, a non-transitory computer-readable storage medium storing one or more programs configured to be executed by one or more processors of computer system that is in communication with one or more perceptual output generation components and one or more sensors is described. The one or more programs include instructions for: detecting, via the one or more sensors, a first set of sensor data that corresponds to a user of the computer system starting a physical activity of a first type; in response to detecting the first set of sensor data that corresponds to the user of the computer system starting the physical activity of the first type: starting a timer of a respective duration; and outputting, via the one or more perceptual output generation components, a first perceptual feedback indicating that the timer of the respective duration is operating; after starting the first timer: in accordance with a determination that the physical activity of the first type is ongoing, continuing to output the first perceptual feedback indicating that the timer of the respective duration is operating; and detecting that a set of one or more termination criteria has been met; and in response to detecting that the set of one or more termination criteria has been met: in accordance with a determination that the set of one or more termination criteria was met based on the physical activity of the first type having continued for at least the respective duration, outputting, via the one or more perceptual output generation components, a second perceptual feedback indicating that the physical activity of the first type was detected for the respective duration.

In accordance with some embodiments, a transitory computer-readable storage medium storing one or more programs configured to be executed by one or more processors of computer system that is in communication with one or more perceptual output generation components and one or more sensors is described. The one or more programs include instructions for: detecting, via the one or more sensors, a first set of sensor data that corresponds to a user of the computer system starting a physical activity of a first type; in response to detecting the first set of sensor data that corresponds to the user of the computer system starting the physical activity of the first type: starting a timer of a respective duration; and outputting, via the one or more perceptual output generation components, a first perceptual feedback indicating that the timer of the respective duration is operating; after starting the first timer: in accordance with a determination that the physical activity of the first type is ongoing, continuing to output the first perceptual feedback indicating that the timer of the respective duration is operating; and detecting that a set of one or more termination criteria has been met; and in response to detecting that the set of one or more termination criteria has been met: in accordance with a determination that the set of one or more termination criteria was met based on the physical activity of the first type having continued for at least the respective duration, outputting, via the one or more perceptual output generation components, a second perceptual feedback indicating that the physical activity of the first type was detected for the respective duration.

In accordance with some embodiments, a computer system is described. The computer system includes: one or more perceptual output generation components; one or more sensors; one or more processors; and memory storing one or more programs configured to be executed by the one or more processors. The one or more programs include instructions for: detecting, via the one or more sensors, a first set of sensor data that corresponds to a user of the computer system starting a physical activity of a first type; in response to detecting the first set of sensor data that corresponds to the user of the computer system starting the physical activity of the first type: starting a timer of a respective duration; and outputting, via the one or more perceptual output generation components, a first perceptual feedback indicating that the timer of the respective duration is operating; after starting the first timer: in accordance with a determination that the physical activity of the first type is ongoing, continuing to output the first perceptual feedback indicating that the timer of the respective duration is operating; and detecting that a set of one or more termination criteria has been met; and in response to detecting that the set of one or more termination criteria has been met: in accordance with a determination that the set of one or more termination criteria was met based on the physical activity of the first type having continued for at least the respective duration, outputting, via the one or more perceptual output generation components, a second perceptual feedback indicating that the physical activity of the first type was detected for the respective duration.

In accordance with some embodiments, a computer system including one or more perceptual output generation components and one or more sensors is described. The computer system also includes: means for detecting, via the one or more sensors, a first set of sensor data that corresponds to a user of the computer system starting a physical activity of a first type; means, in response to detecting the first set of sensor data that corresponds to the user of the computer system starting the physical activity of the first type, for: starting a timer of a respective duration; and outputting, via the one or more perceptual output generation components, a first perceptual feedback indicating that the timer of the respective duration is operating; means, after starting the first timer, for: in accordance with a determination that the physical activity of the first type is ongoing, continuing to output the first perceptual feedback indicating that the timer of the respective duration is operating; and detecting that a set of one or more termination criteria has been met; and in response to detecting that the set of one or more termination criteria has been met: in accordance with a determination that the set of one or more termination criteria was met based on the physical activity of the first type having continued for at least the respective duration, outputting, via the one or more perceptual output generation components, a second perceptual feedback indicating that the physical activity of the first type was detected for the respective duration.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for tracking the performance of a physical activity event, thereby increasing the effectiveness, efficiency, and user satisfaction with such devices. Such methods and interfaces may complement or replace other methods for tracking the performance of a physical activity event.

This relates to detecting individual health related events (e.g., handwashing events) based on multiple sensors including motion and audio sensors. Detecting a qualifying handwashing event can include detecting a qualifying scrubbing event based on motion data (e.g., accelerometer data) and a qualifying rinsing event based on audio data. In some examples, power consumption can be reduced by implementing one or more power saving mitigations. In some examples, acquiring and processing motion data can be used to trigger the acquisition and/or processing of audio data. In some examples, processing of motion data by a low-power processor can be used to trigger the acquisition and/or processing of audio data by another processor (e.g., a host processor). In some examples, the quality of the acquired data and/or the quality of the processing of the acquired data streams can be changed based on one or more triggers. In some examples, the trigger(s) described herein can be dynamically adjusted (e.g., heightened to reduce processing/power consumption) based on one or more power-related states of the device.

As discussed herein, detecting individual health related events can include a detecting a handwashing event (e.g., detecting inputs the system considers to be washing hands). The handwashing event can include a scrubbing event (e.g., detecting inputs the system considers to be scrubbing hands together) and a rinsing event (e.g., detecting inputs the system considers to be rinsing of the hands with water). As used herein, qualifying events refer to events that meet one or more criteria set for the system. For example, detecting a qualifying scrubbing event based on (e.g., using) motion data can include detecting motion data meeting one or more criteria including a duration criterion, an amplitude criterion, a speed criterion, etc. The one or more criteria can be set to differentiate between motion associated with scrubbing hands together from other motion (e.g., lifting a wrist, swinging arms, various exercises, sitting, typing, etc.). Likewise, detecting a qualifying rinsing event based on (e.g., using) audio data can include detecting audio data meeting one or more criteria including a duration criterion, an amplitude criterion, a frequency content criterion, etc. The one or more criteria can be set to differentiate between audio associated with rinsing hands from other audio (e.g., environmental sounds, traffic, wind, etc.). In some examples, detecting a qualifying handwashing event can include meeting one or more criteria. The one or more criteria can including detecting a qualifying rinsing event within a threshold period of time (e.g., within 30 second, within I minute, etc.) of detecting a qualifying scrubbing event.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIGS. 7A-7C are a flow diagram illustrating a method for tracking the performance of a physical activity event using a computer system, in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for tracking the performance of a physical activity event, such as a handwashing event, and for reminding users to perform the physical activity event in specific circumstances. Such techniques can reduce the cognitive burden on a user who need to perform or track the performance of a physical activity event, thereby enhancing productivity. Further, such techniques can reduce processor and battery power otherwise wasted on redundant user inputs.

Figure 6A:
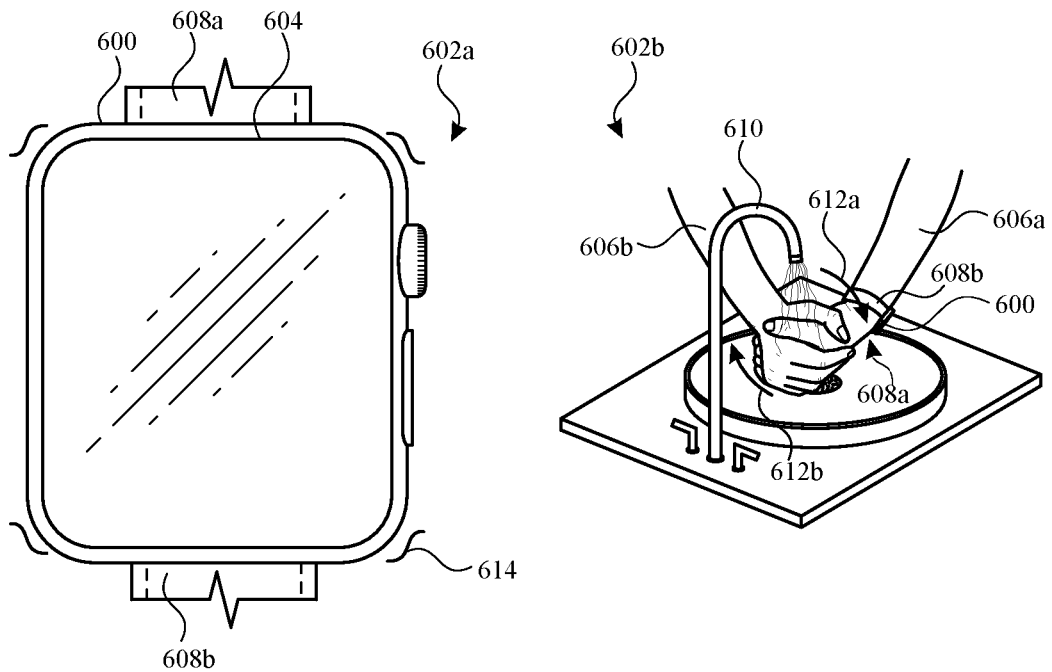
FIGS. 6A-6W illustrate exemplary user interfaces for tracking the performance of a physical activity event, in accordance with some embodiments.
Figure 6W:
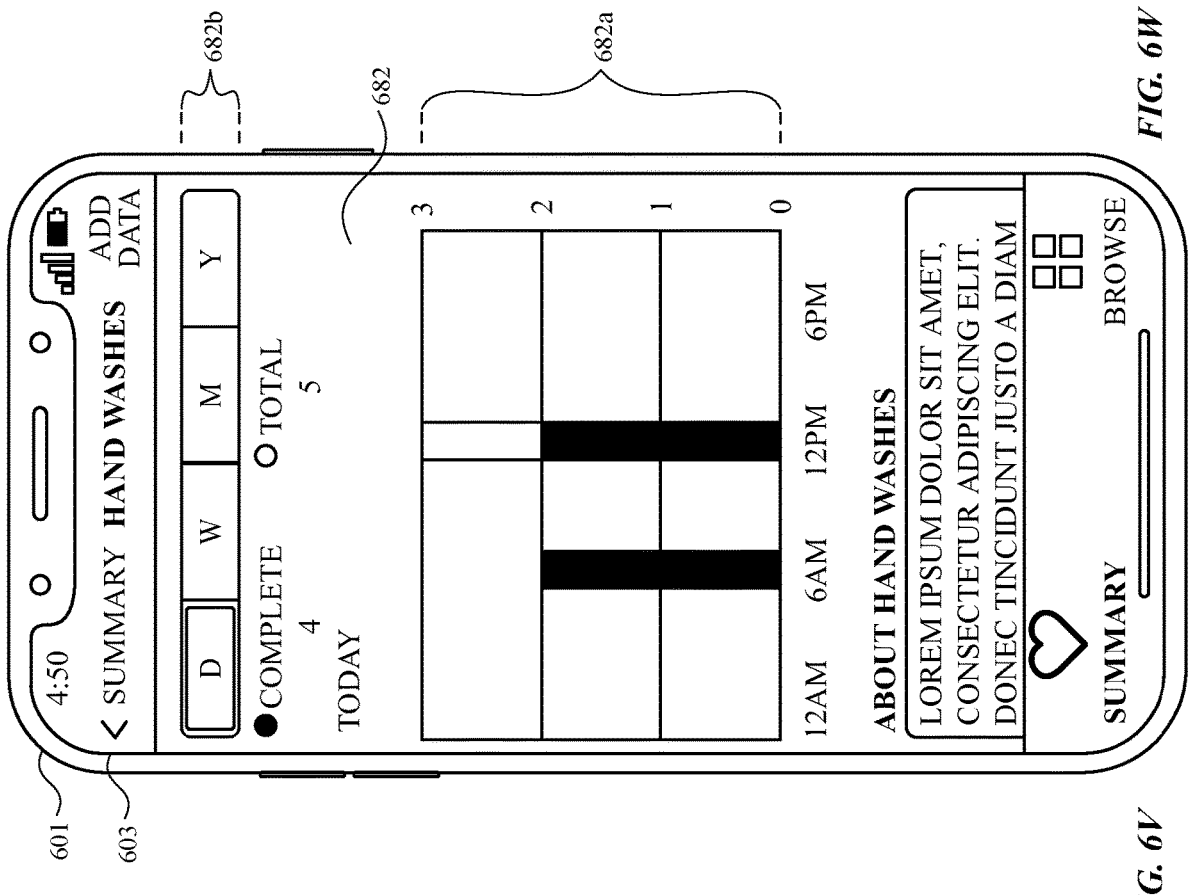
Figure 7A:
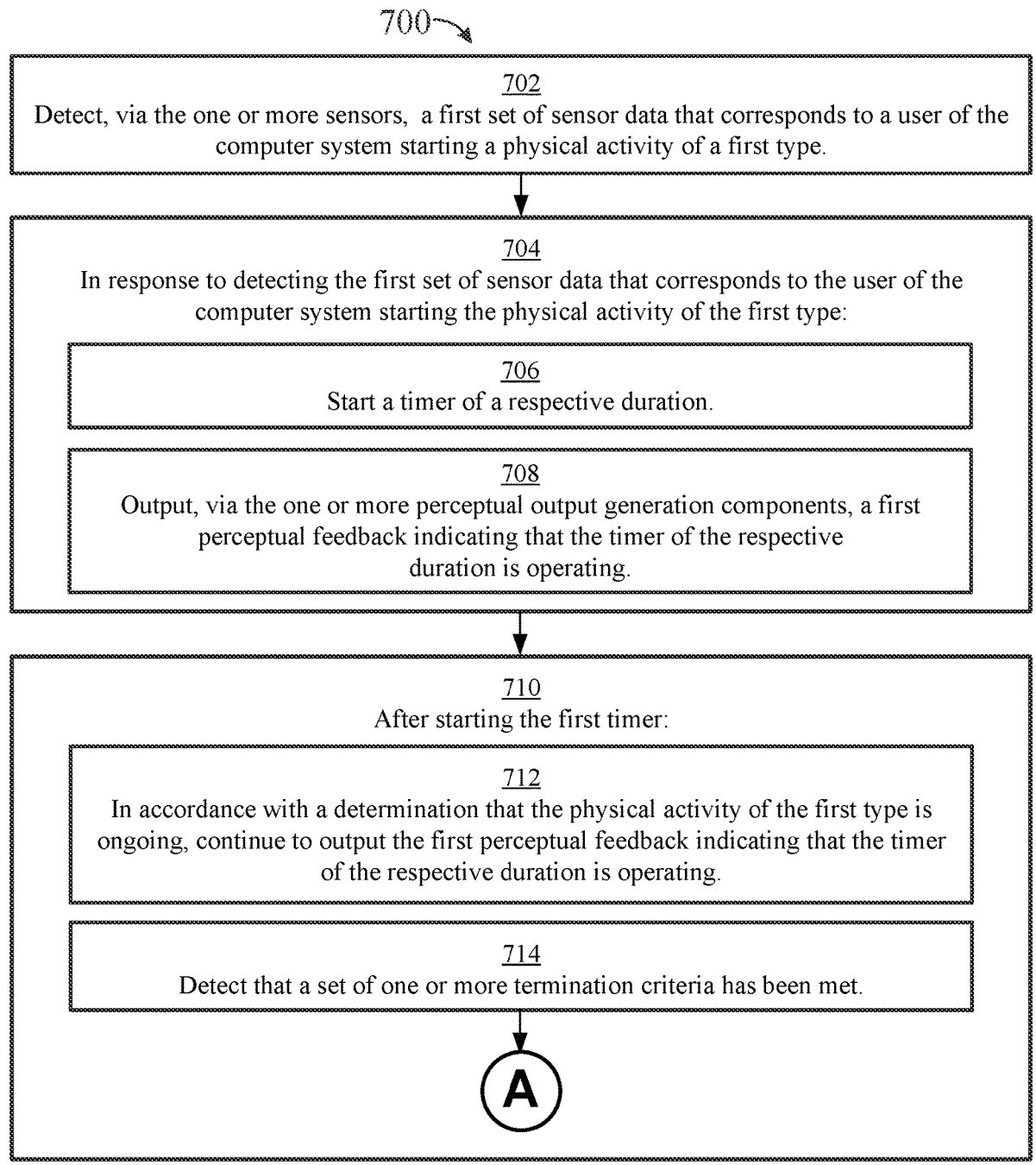

Below, FIGS. 1A-1B, 2, 3, 4A-4B, and 5A-5B provide a description of exemplary devices for performing the techniques for tracking the performance of a physical activity event. FIGS. 6A-6W illustrate exemplary user interfaces for tracking the performance of a physical activity event. FIGS. 7A-7C is a flow diagram illustrating methods of tracking the performance of a physical activity event with some embodiments. The user interfaces in FIGS. 6A-6W are used to illustrate the processes described below, including the processes in FIGS. 7A-7C.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
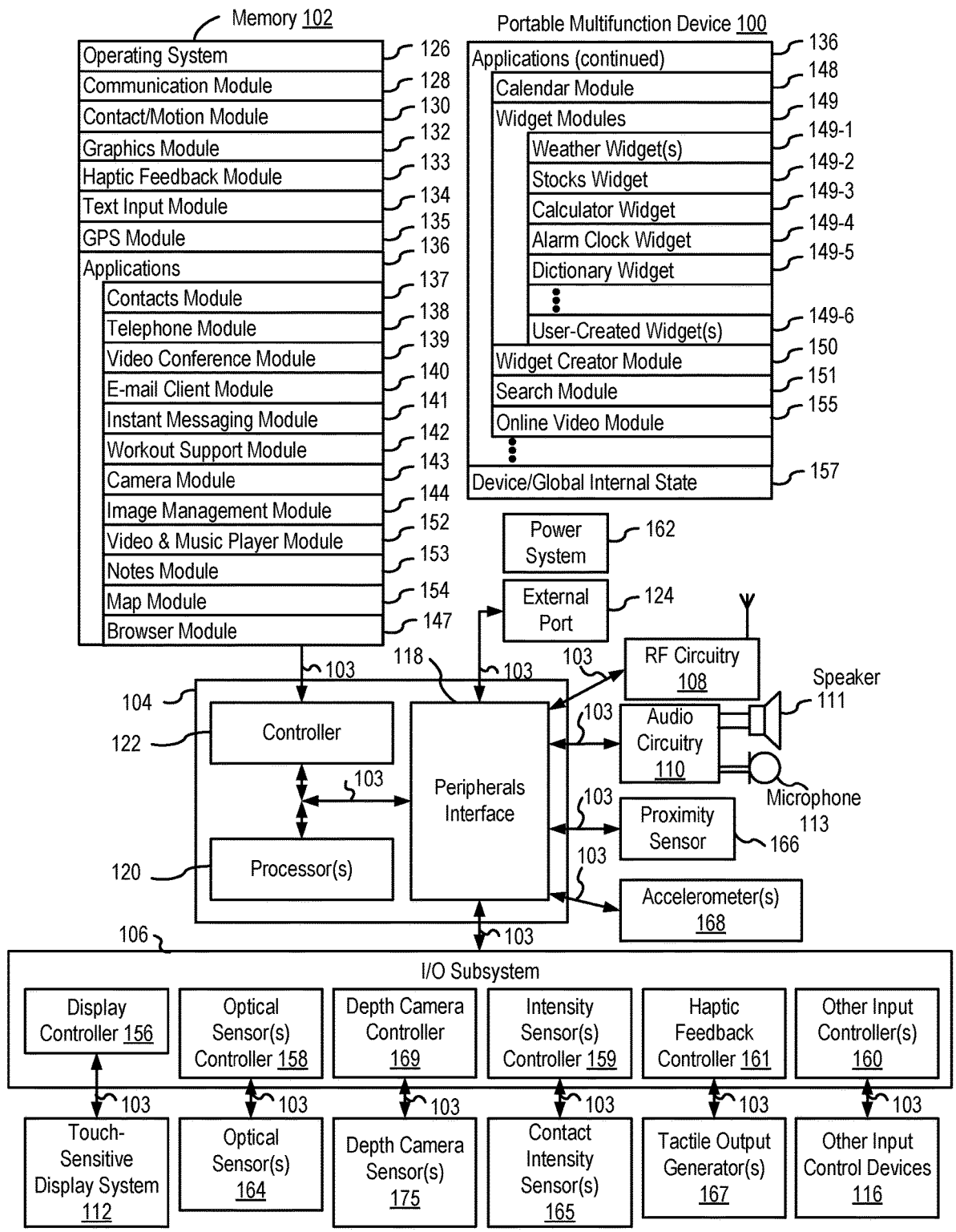
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs (such as computer programs (e.g., including instructions)) and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures) as input. In some embodiments, the one or more input devices are integrated with the computer system. In some embodiments, the one or more input devices are separate from the computer system.

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
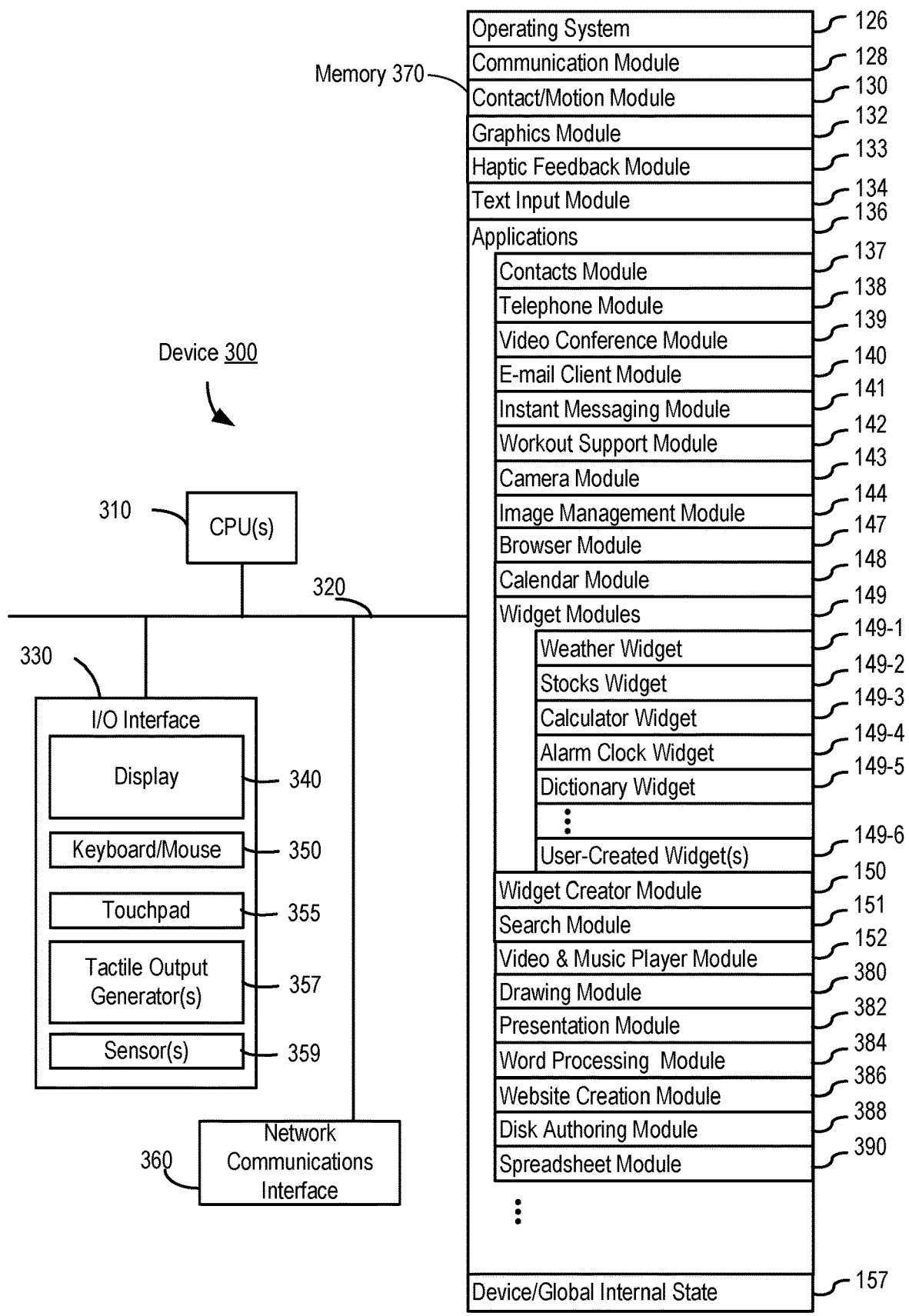
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conference module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs (such as computer programs (e.g., including instructions)), procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
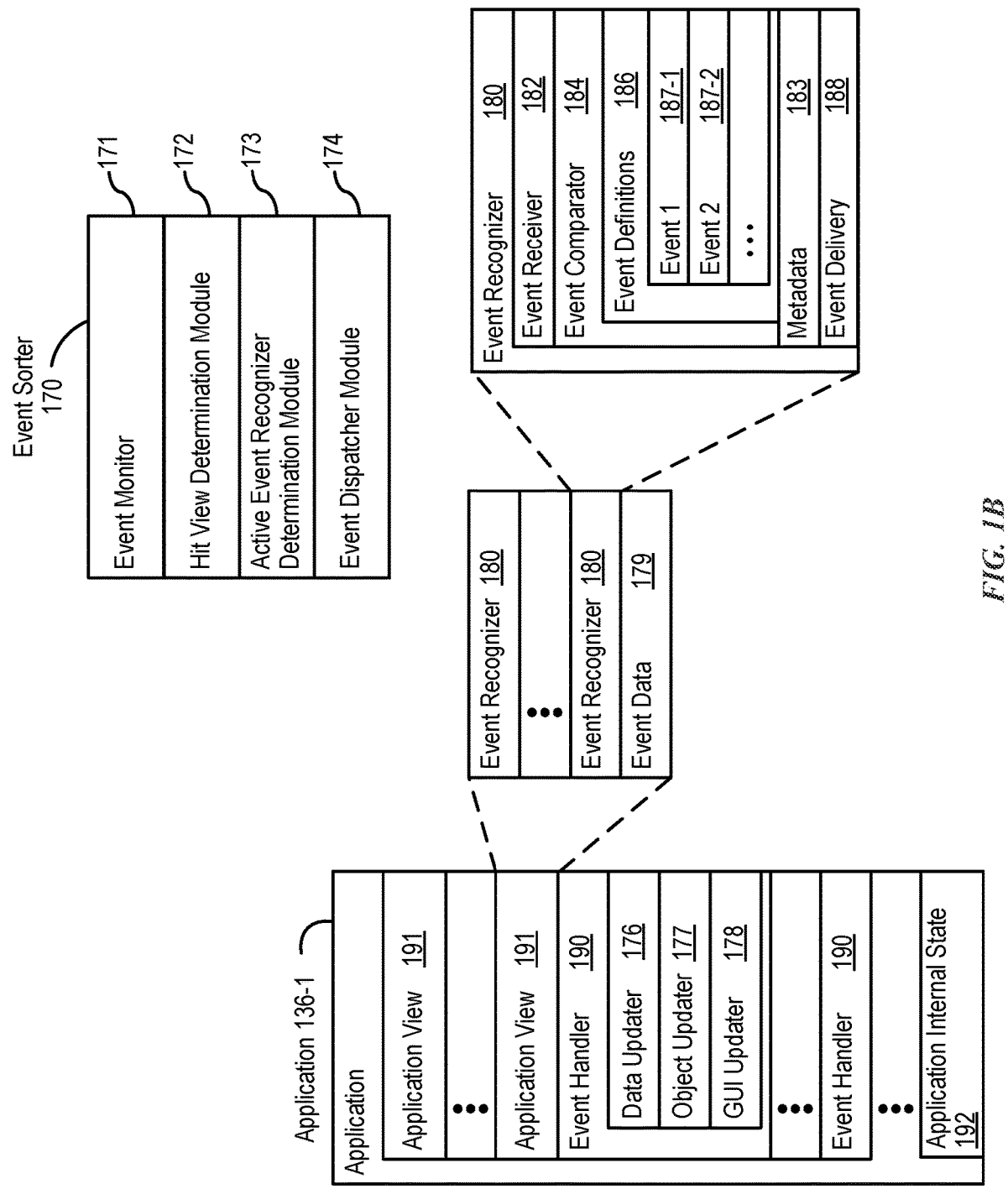
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
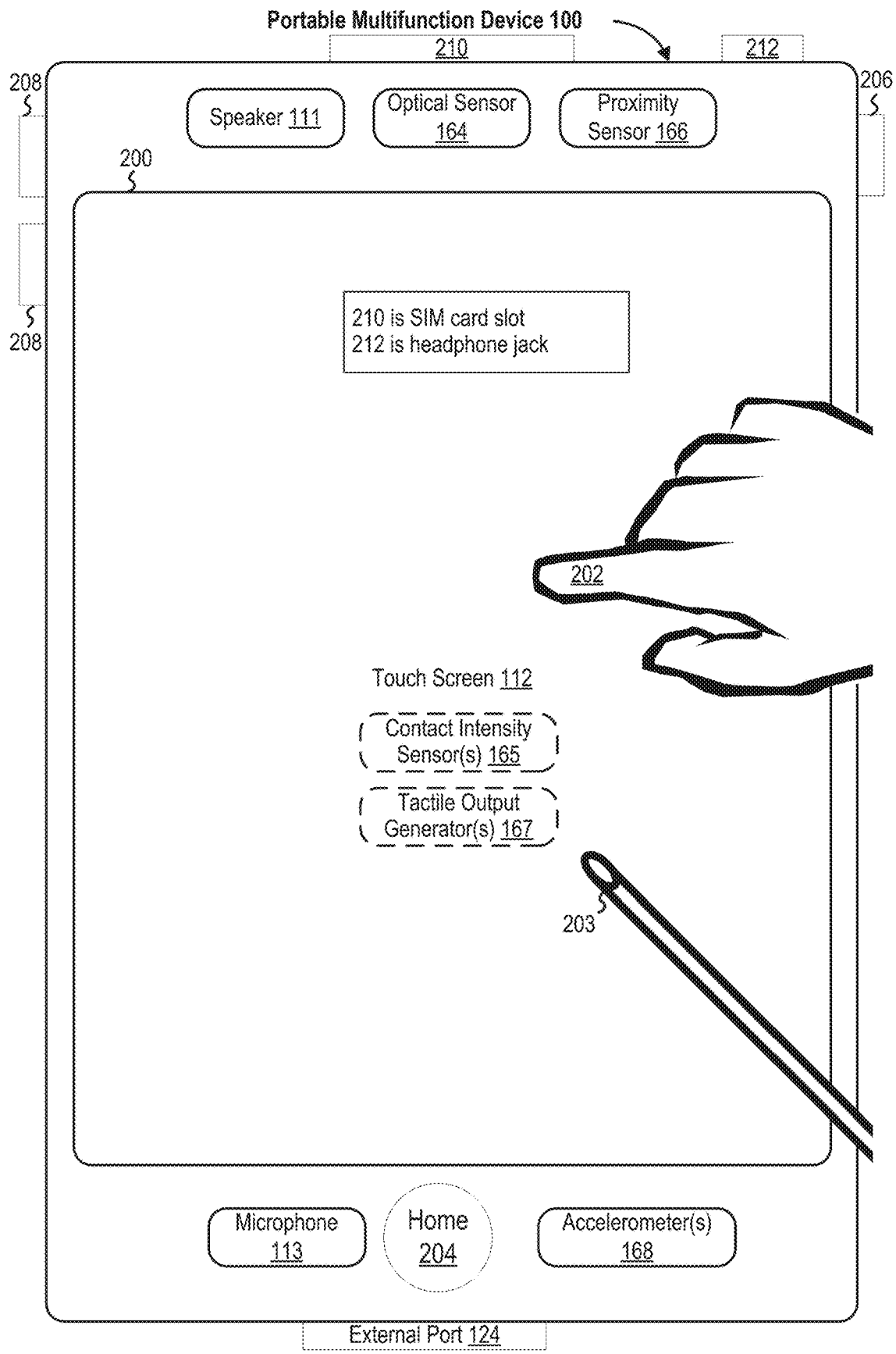
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or computer programs (e.g., sets of instructions or including instructions) need not be implemented as separate software programs (such as computer programs (e.g., including instructions)), procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
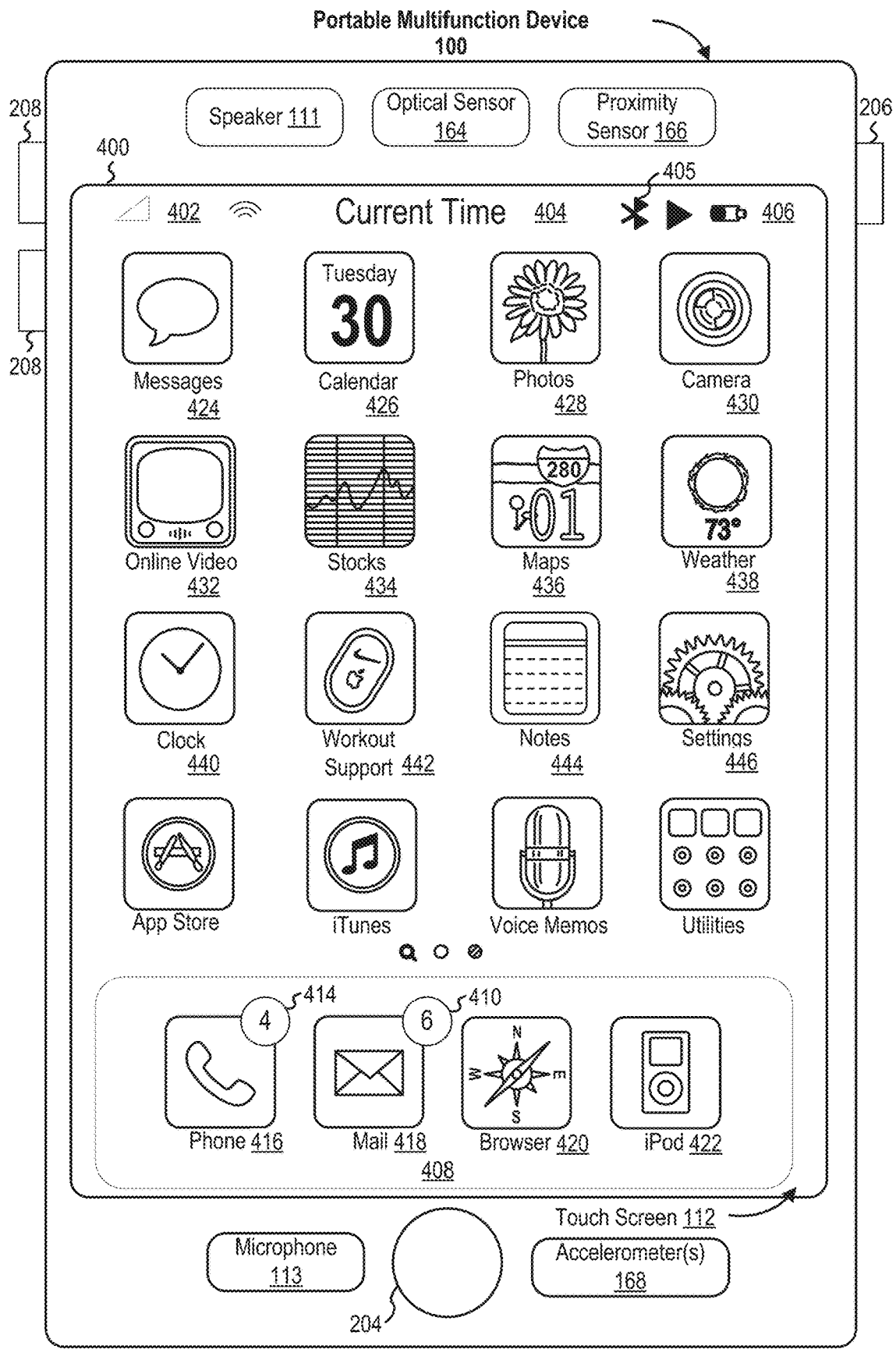
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"
  Icon 444 for notes module 153, labeled "Notes;" and
  Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
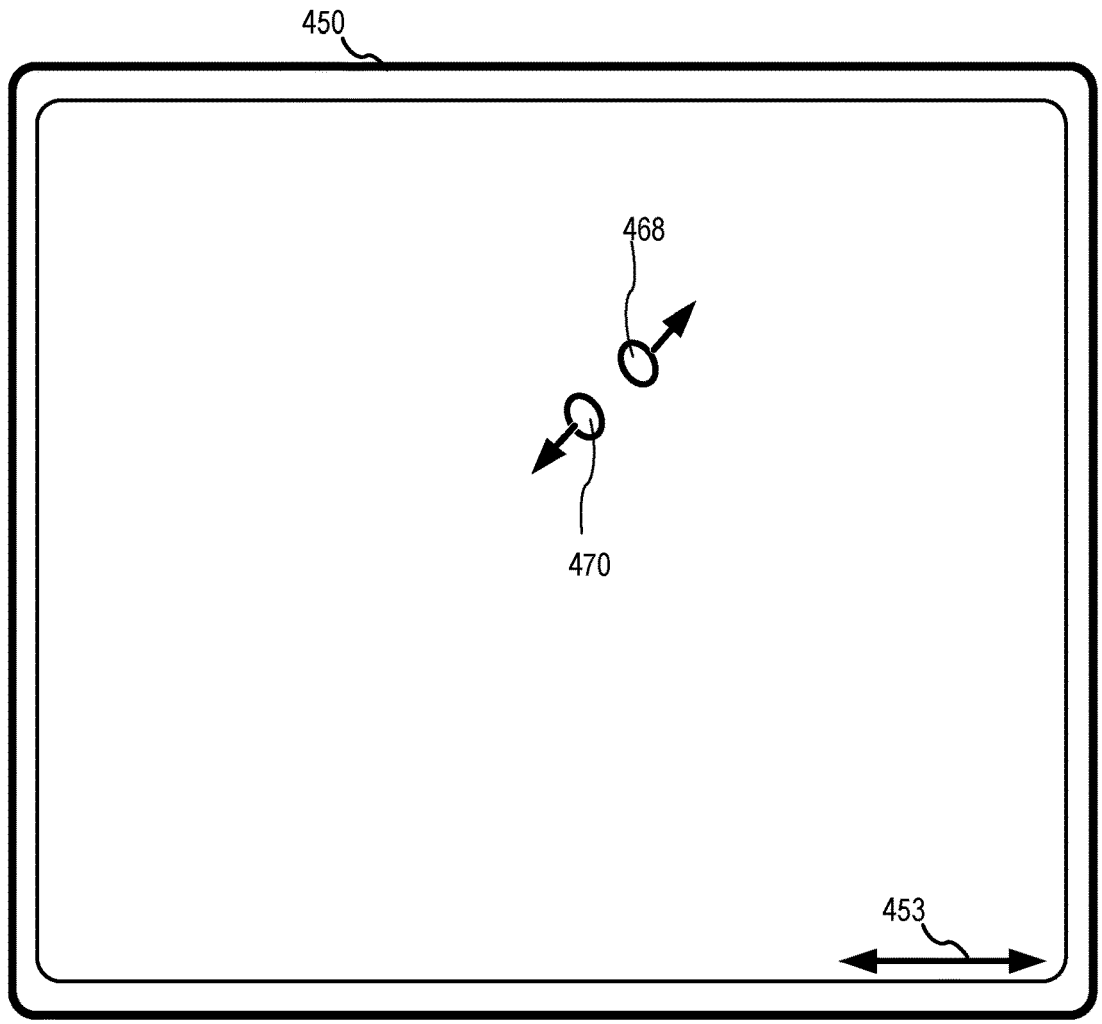
FIG. 4B illustrates an exemplary user interface for a multifunction device with a touch-sensitive surface that is separate from the display in accordance with some embodiments.
Figure 4B:
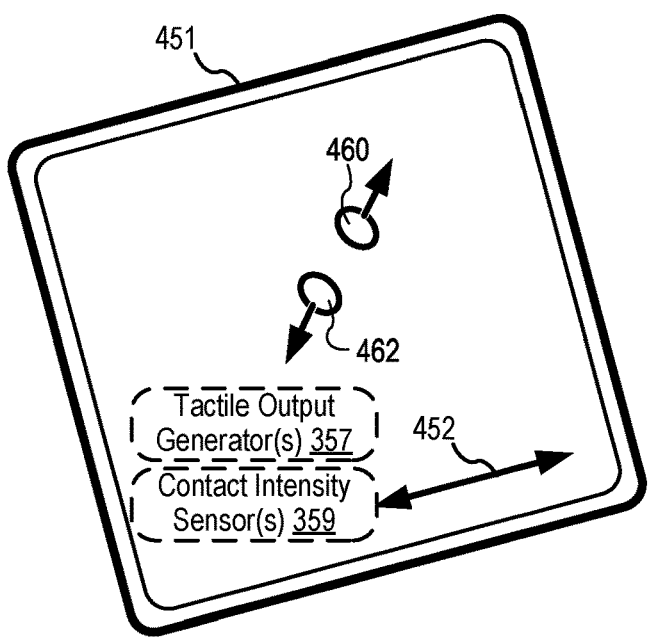

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
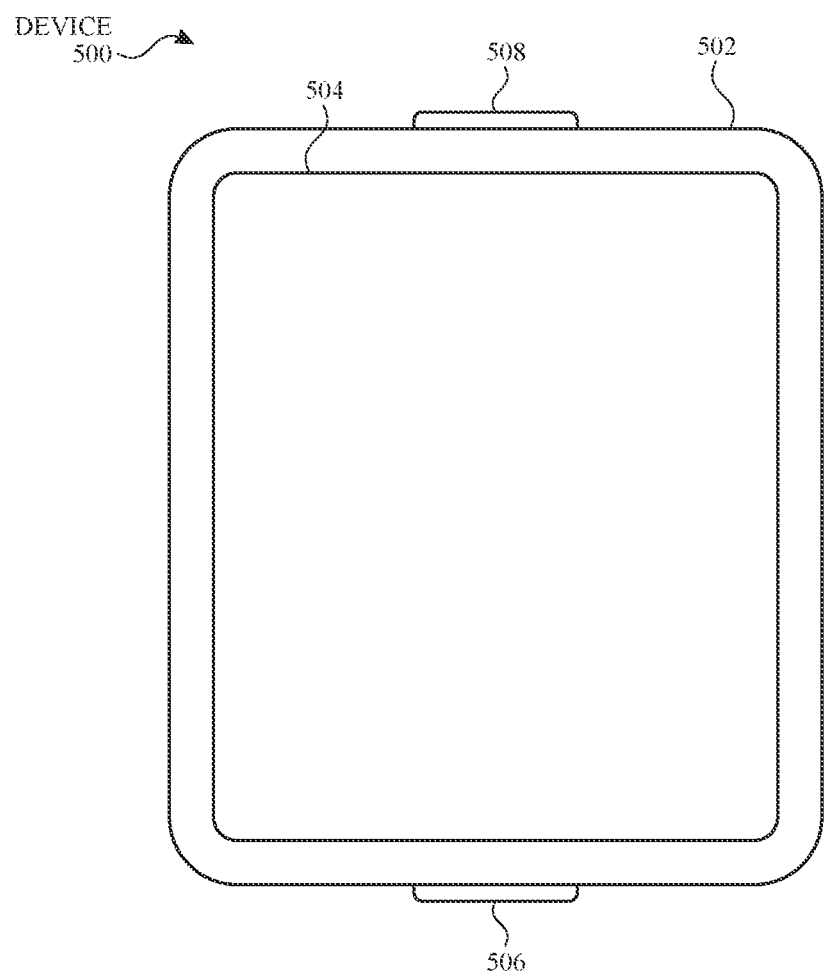
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
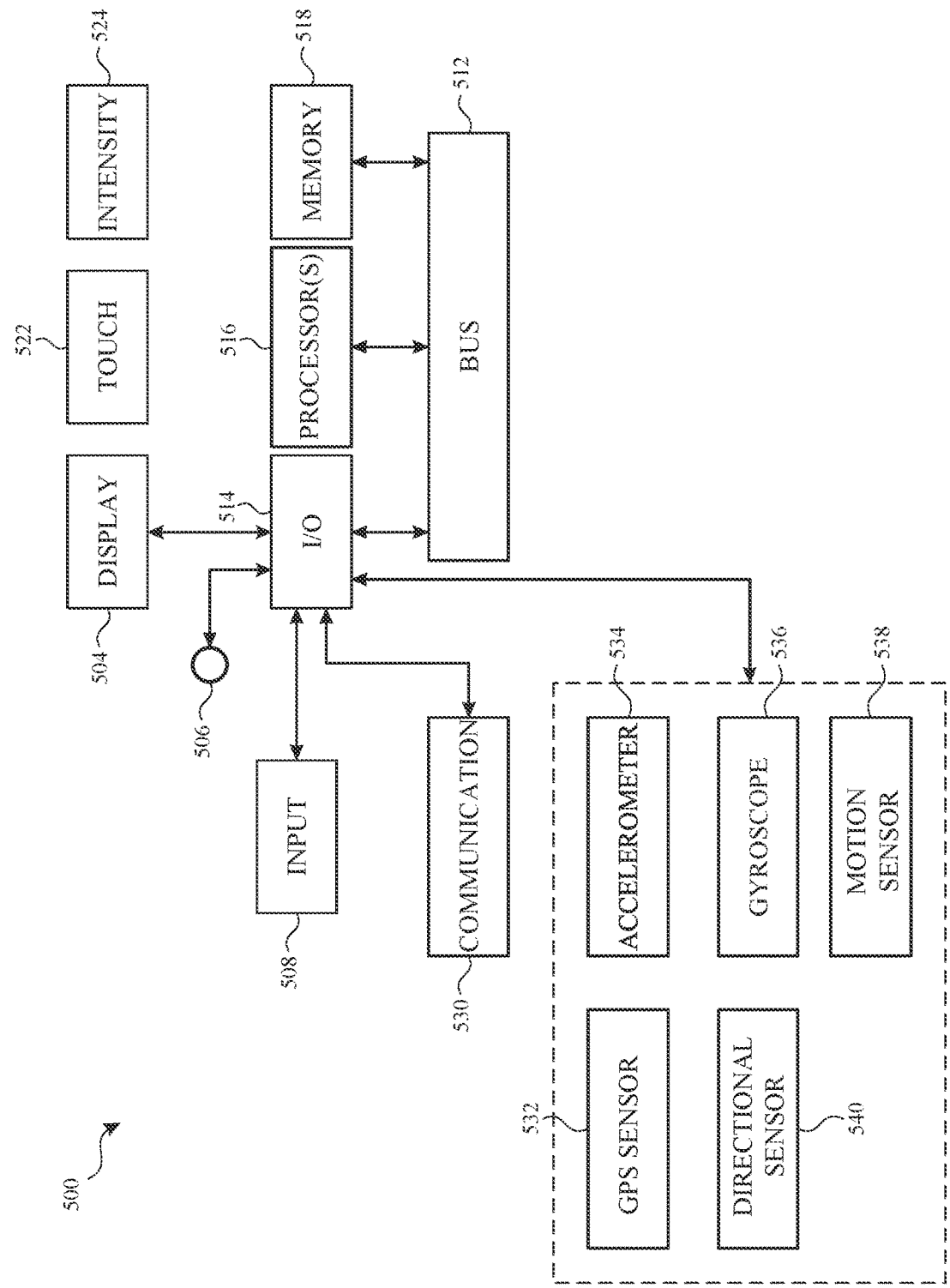
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including process 700 (FIGS. 7A-7C). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:

an active application, which is currently displayed on a display screen of the device that the application is being used on;

a background application (or background processes), which is not currently displayed, but one or more processes for the application are being processed by one or more processors; and a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on an electronic device, such as portable multifunction device 100, device 300, or device 500.

FIGS. 6A-6W illustrate exemplary user interfaces for tracking and suggesting the performance of a physical activity event, in accordance with some embodiments. The user interfaces in these figures are used to illustrate the processes described below, including the processes in FIGS. 7A-7C.

FIG. 6A illustrates two views of a device 600 at a given point in time; device 600 is a smart watch being worn on the left wrist of user. The left side of FIG. 6A depicts device 600 in an enlarged view 602a that includes a view of touchscreen display 604 of device 600. The right side of FIG. 6A depicts device 600 in an as-worn view 602b that also includes a depiction of arms 606a (left) and 606b (right) of the user. Device 600 is secured to the wrist of the user's arm 606a via straps 608a and 608b. In some embodiments, device 600 includes one or more features or elements of devices 100, 300, and 500, including microphone 113 and accelerometers 168, as shown in FIG. 1A.

As shown in enlarged view 602a of FIG. 6A, touchscreen display 604 of device 600 is currently not displaying content. In some embodiments, touchscreen display 604 is displaying content, but in an interface locked state and/or in a low power state.

As shown in as-worn view 602b of FIG. 6A, the user is just completing the physical activity of washing their hands at sink 610, as illustrated by movement arrows 612a and 612b. At FIG. 6A, device 600 has previously detected sensor data (e.g., via microphone 113 and accelerometers 168) that device 600 identifies as corresponding to the start and ongoing performance of the physical activity of handwashing (e.g., a handwashing event). In some embodiments, device 600 identifies that sensor data corresponds to handwashing based on one or more techniques described in Appendix A. Further at FIG. 6A, device 600 detects sensor data that indicates that the user has completed the physical activity of handwashing (e.g., device 600 detects a cessation of sensor data that indicates handwashing after detecting such data for a period of time). In response to detecting that the user has completed the physical activity of handwashing, device 600 outputs tactile output 614.

Figure 6B:
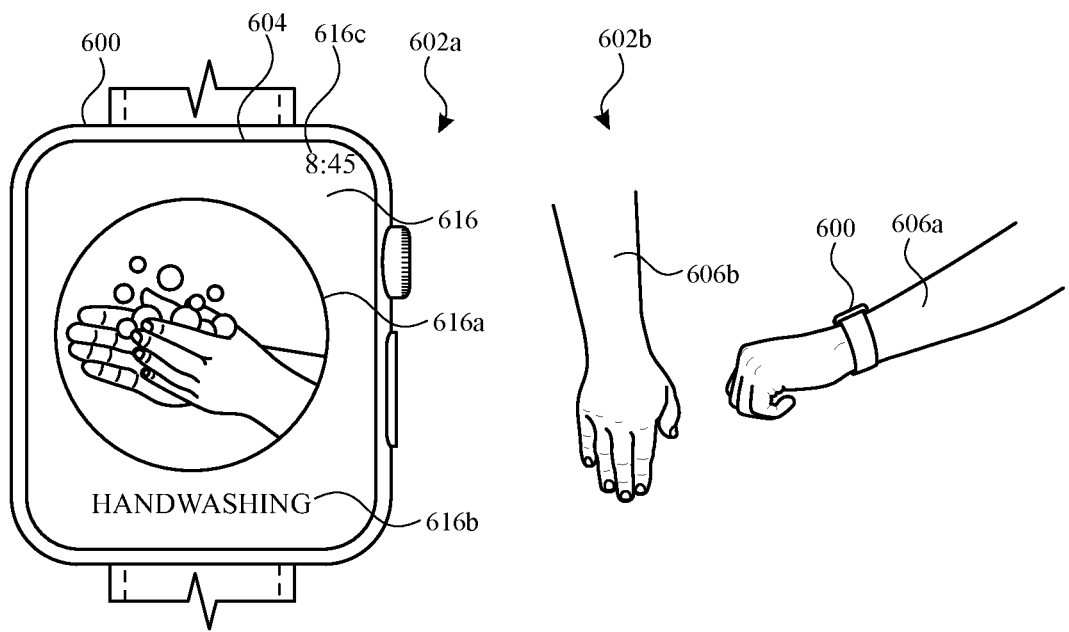

At FIG. 6B, after outputting tactile output 614, device 600 detects that the device has been placed into a viewing position orientation (e.g., the user has raised their left arm 606a so that touchscreen display 604 is visible to the user (e.g., device 600 has detected a wrist-raise gesture)). In response to detecting that the device has been placed into a viewing position orientation (e.g., a predetermined orientation), device 600 displays introductory notification user interface 616, which includes graphic 616a and text 616b ("HANDWASHING"), as well as time indication 616c (showing the current time of 8:45 (e.g., AM)). Device 600 displays introductory notification user interface 616 for a predetermined period of time (e.g., 5 seconds), before transitioning to display of setup user interface 618 of FIG. 6C. In some embodiments, introductory notification user interface 616 provides the user with an introduction to a yet-to-be enabled feature relevant to monitoring handwashing events. In some embodiments, device 600 displays introductory notification user interface 616 upon initial device setup. In some embodiments, device 600 displays introductory notification user interface 616 after a software upgrade.

Figure 6C:
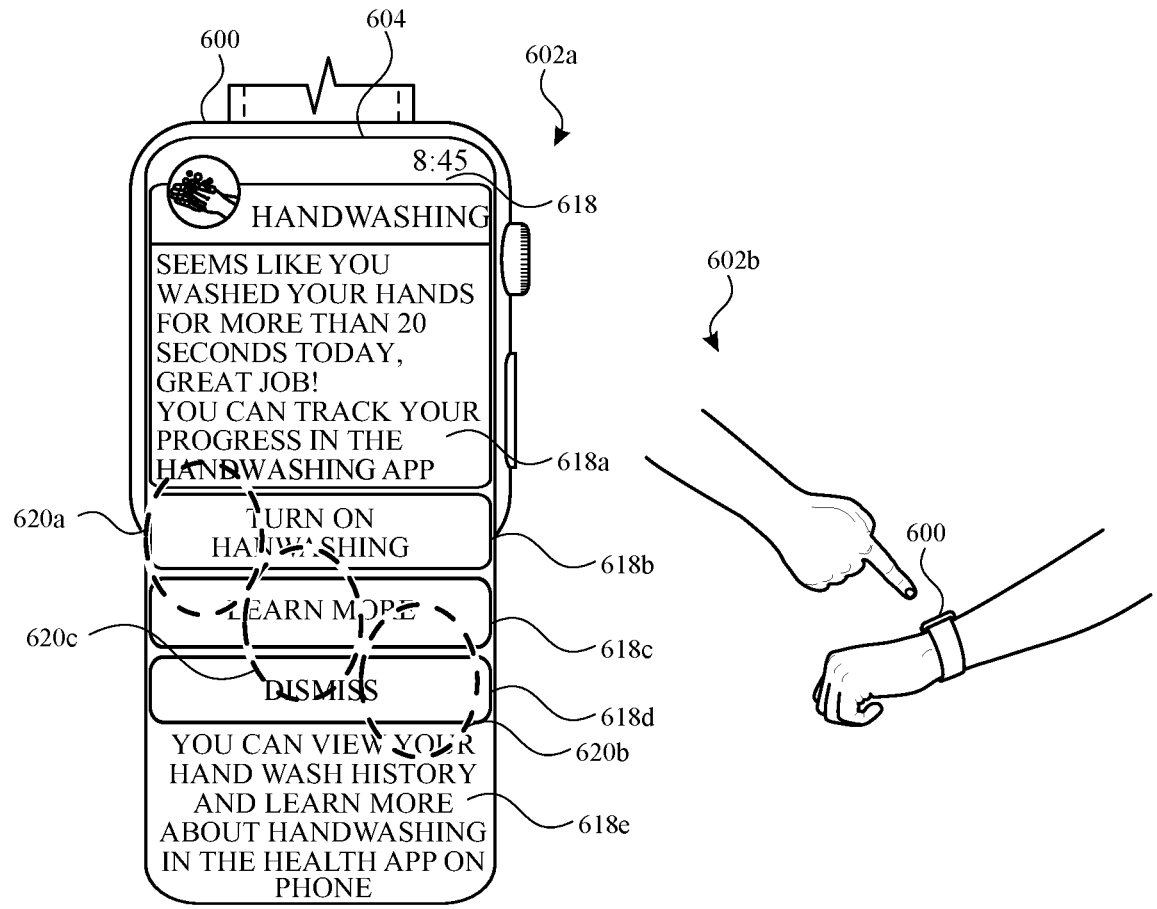

At FIG. 6C, device 600 displays setup user interface 618 on touchscreen display 604, as shown in enlarged view 602a. Setup user interface 618 includes introductory text 618a, feature enabling affordance 618b ("TURN ON HANDWASHING"), learning affordance 618c ("LEARN MORE"), dismiss affordance 618d ("DISMISS"), and informational text 618e. Introductory text 618a includes information that device 600 detected the start and ongoing performance of the physical activity of handwashing for a predetermined period of time (e.g., 20 seconds) and an indication that tracked user handwashing data is available in a companion application (e.g., an application of a device that is in communication with device 600, such as a phone).

As shown in the as-worn view 602b of FIG. 6C, the user performs a gesture on device 600. Turning back to the enlarged view 602a, while displaying setup user interface 618, device 600 alternatively receives (e.g., detects) input 620a (e.g., a tap) corresponding to selection of feature enabling affordance 618b, input 620b corresponding to selection of dismiss affordance 618d, or input 620c corresponding to selection of learning affordance 618c. Device responds to these alternative inputs, as described below.

In response to receiving input 620a, device 600 enables (e.g., turns on) the handwashing detection and tracking feature. In some implementations, enabling handwashing also enables automatic handwashing reminders or suggestions that are displayed to a user at various times, e.g., based on a user's location, a time of day, or detected user activity. Operation of this handwashing feature is discussed in more detail with reference to FIGS. 6E-6W, below. In response to receiving input 620b, device 600 dismisses (e.g., ceases displaying) setup user interface 618 without enabling the handwashing detection and tracking feature. In some embodiments, in response to receiving input 620b, device 600 suppresses further prompts for enabling the handwashing detection, reminders, and tracking feature. In some embodiments, in response to receiving input 620b, device 600 ceases displaying prompts for enabling the handwashing detection and tracking feature for a period of time (e.g., 1 day, 1 week, 1 month). In response to receiving input 620c, device 600 displays informational user interface 622, as shown in FIG. 6D.

Figure 6D:
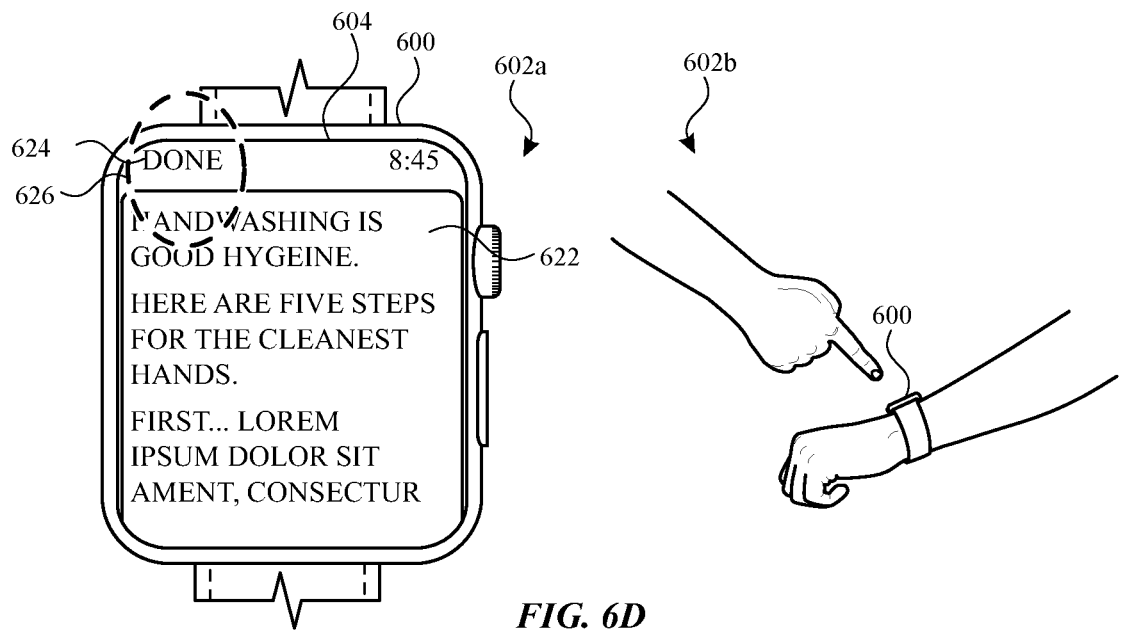

At FIG. 6D in enlarged view 602a, device 600 displays informational user interface 622 containing additional information about handwashing. In some embodiments, informational user interface 622 further contains information about the handwashing detection, reminders, and tracking feature. Device 600 receives input 626 at done affordance 624, which corresponds to the user performing a gesture on device 600 in as-worn view 602b. In response to receiving input 626, device 600 displays (e.g., returns to) setup user interface 618 of FIG. 6C.

Figure 6E:
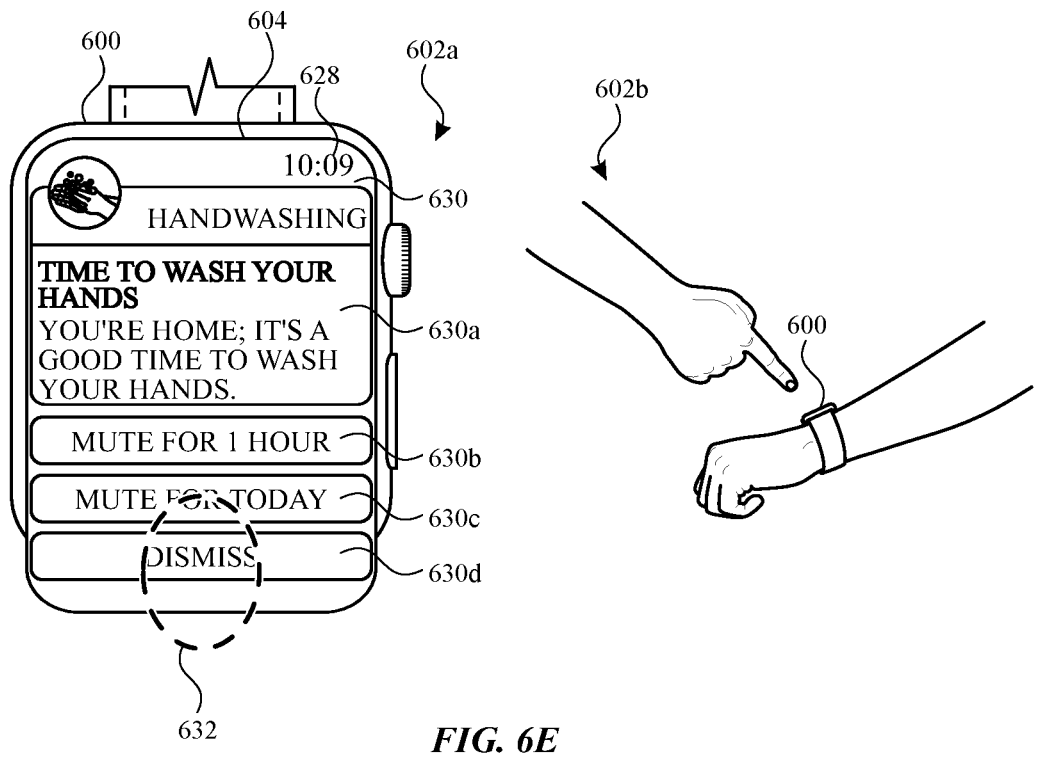

At FIG. 6E, device 600 displays handwashing reminder notification 630 at a time shown by time indication 628 (showing current time 10:09 (e.g., AM)) on touchscreen display 604, after device 600 received input 620a for enabling the handwashing detection and tracking feature, as shown in FIG. 6C. Handwashing reminder notification 630 is an automatic notification that is a function of the enabled handwashing detection and tracking feature and that optionally is generated based on the user's location (e.g., the user arrived at home), as shown by text 630a.

In some embodiments, various criteria prompt the display of handwashing reminder notifications. In some embodiments, device 600 displays a handwashing reminder notification based on the user's location (e.g., the user arrives at a particular destination (e.g., home, workplace, airport, or restaurant)). In some embodiments, device 600 displays a handwashing reminder notification based on the time of day. In some embodiments, device 600 displays a handwashing reminder notification based on the duration of time since the previous handwashing event (e.g., 2 hours since the last time the user washed their hands). In some embodiments, device 600 displays a handwashing reminder notification based on other detected user activity, e.g., that a user has just finished a workout. In some embodiments, device 600 does not display a handwashing reminder notification if a handwashing event is detected within a predetermined amount of time from the detection of a prompting criteria.

As shown in the enlarged view 602a of FIG. 6E, handwashing reminder notification 630 also includes mute affordances 630b and 630c, which, when selected, suppress handwashing reminder notifications for an hour or for the current day, respectively. Handwashing reminder notification 630 further includes dismiss affordance 630d, which, when selected, dismisses current handwashing reminder notification 630. Device 600 receives input 632 corresponding to the selection of dismiss affordance 630d. In response to receiving input 632, device 600 ceases displaying handwashing reminder notification 630 and displays watch face user interface 634 in FIG. 6F.

Figure 6F:
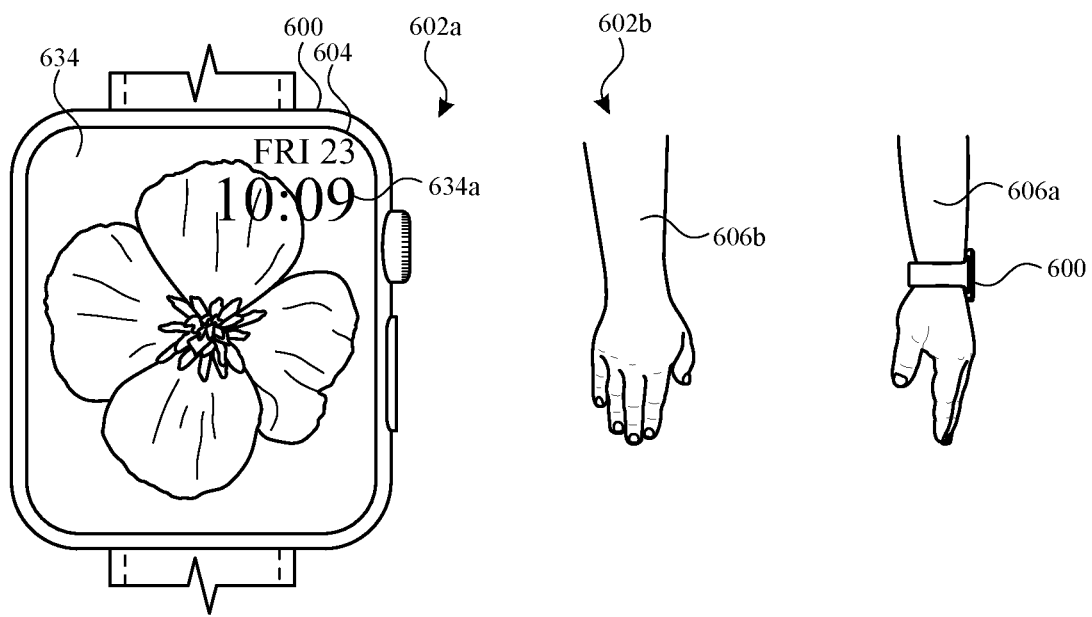

At FIG. 6F, in enlarged view 602a, device 600 displays watch face user interface 634 having time indication 634a (showing current time 10:09 (e.g., AM)) on touchscreen display 604. In as-worn view 602b, the user is in a neutral position, as illustrated by user's arms 606a and 606b.

Figure 6G:
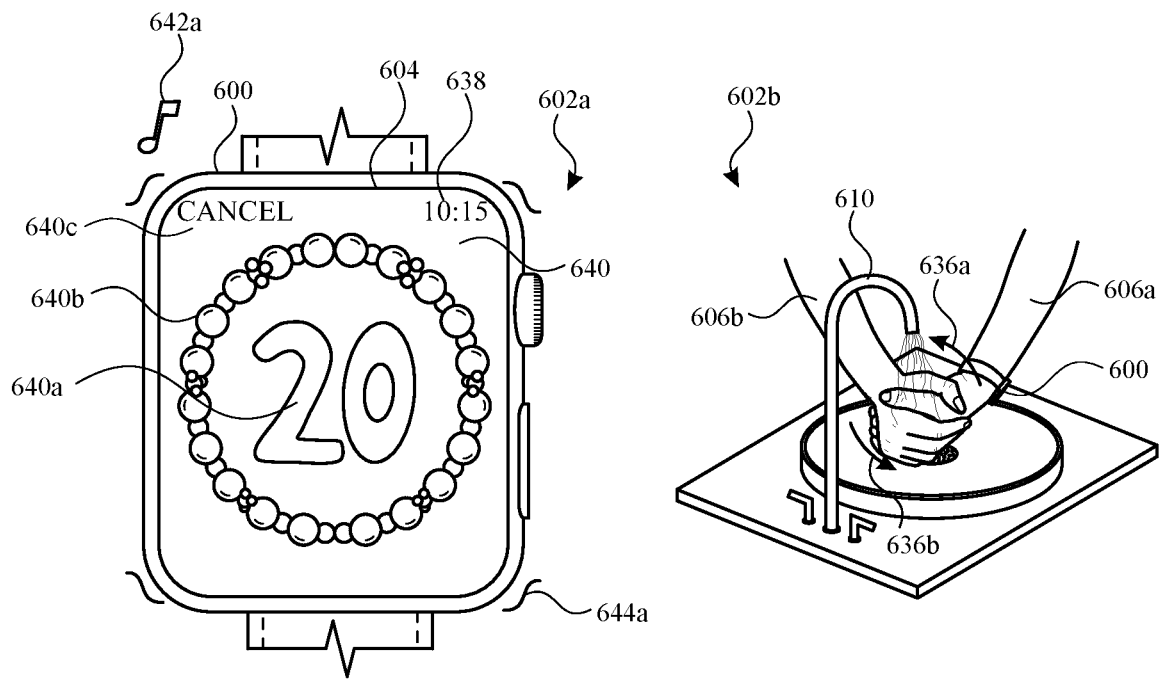

Turning now to FIG. 6G, device 600 detects sensor data (e.g., via microphone 113 and accelerometers 168) that device 600 identifies as corresponding to the start of a handwashing event. As shown in as-worn view 602b, the user is starting the physical activity of washing their hands at sink 610, as illustrated by movement arrows 636a and 636b. In some embodiments, the sensor data is audio data (e.g., water running in sink 610). In some embodiments, sensor data includes hand movement, or hand movement and audio data. Upon detection of the sensor data (e.g., in response to detection of the sensor data), device 600 automatically (e.g., without requiring an express user request input) displays handwashing user interface 640 on touchscreen display 604 and outputs audio feedback 642a (e.g., the sound of multiple, small bubbles bursting) and tactile feedback 644a (e.g., a light haptic vibration). In some embodiments, device 600 does not output audio feedback 642a (e.g., device is on silent mode). In some embodiments, device 600 does not output tactile feedback 644a. In some embodiments, device 600 continuously monitors for the sensor data corresponding to a handwashing event without having to receive a user input requesting activation of monitoring and displays user interface 640 after detecting the sensor data while displaying watch face user interface 634 of FIG. 6F or while the touchscreen display 604 is not displaying content, such as in FIG. 6A.

As shown in enlarged view 602a of FIG. 6G, handwashing user interface 640 includes time indication 638, which now reads 10:15 (e.g., AM), 6 minutes after dismissing handwashing reminder notification 630 from FIG. 6E. Further, handwashing user interface 640 includes countdown timer 640a starting at a number, (e.g., "20" representing 20 seconds) and progress indicator 640b (e.g., full circle of bubbles). In some embodiments, countdown timer 640a counts for a predetermined duration (e.g., 10 seconds, 20 seconds, 30 seconds). In some embodiments, the predetermined duration of the countdown timer 640a is selected by the user. In some embodiments, countdown timer 640a counts up (e.g., starting at 0 or 1). In some embodiments, progress indicator 640b creates (e.g., draws in) a circle as the handwashing event progresses. Handwashing user interface 640 also includes cancel affordance 640c. In some embodiments, selection of the cancel affordance 640c dismisses user interface 640 and redisplays watch face user interface 634 as illustrated in FIG. 6F, while also ending tracking of this particular handwashing event. In some embodiments, selection of the cancel affordance or detection of a cover gesture over device 600 dismisses the handwashing user interface 640 (e.g., and redisplays watch face user interface 634 of FIG. 6F).

Figure 6H:
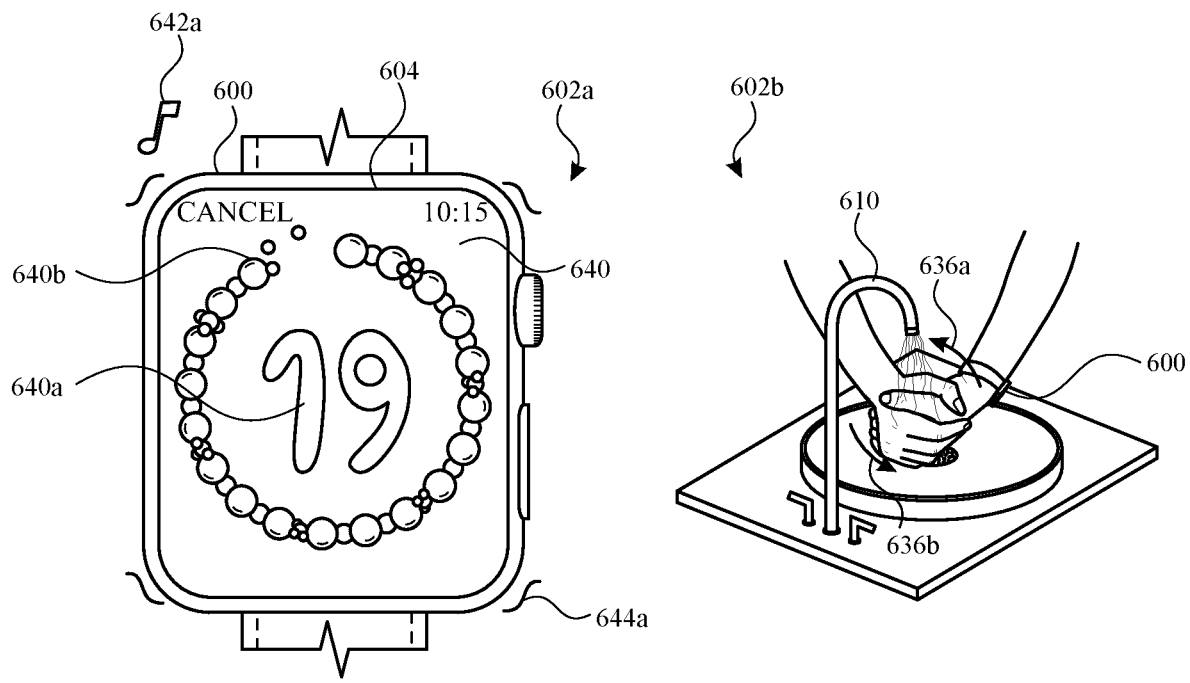

At FIG. 6H, as shown in the as-worn view 602b, the user continues the physical activity of washing their hands (e.g., the physical activity (e.g. handwashing) is ongoing) at sink 610, as illustrated by movement arrows 636a and 636b. As shown in the enlarged view 602a, the countdown timer 640a of handwashing user interface 640 has changed from "20" in FIG. 6G to "19" in FIG. 6H to indicate that 1 second of detecting sensor data has passed (e.g., the handwashing event has been ongoing for 1 second). From FIG. 6G to FIG. 6H, progress indicator 640b animates a portion (e.g., 1/20) of the bubbles shown in the circle popping in the counterclockwise direction. Various other ways of displaying handwashing progress are contemplated including bubbles shown in the circle popping in a clockwise direction or different counting animations. Device 600 continues outputting audio feedback 642a and tactile feedback 644a. In some embodiments, device 600 outputs audio feedback at 1 second intervals (e.g., one bubble bursting at each second). In some embodiments, device 600 outputs different audio feedback at each 1 second interval (e.g., different bubble popping tones). In some embodiments, device 600 outputs uninterrupted audio feedback. In some embodiments, device 600 outputs tactile feedback at 1 second intervals. In some embodiments, device 600 outputs uninterrupted tactile feedback. As the user continues the physical activity of washing their hands (e.g., the handwashing event continues (e.g., progresses)), the countdown timer 640a of handwashing user interface 640 continues counting down the seconds of detecting sensor data. Progress indicator 640b continues animating bubbles popping.

Figure 6I:
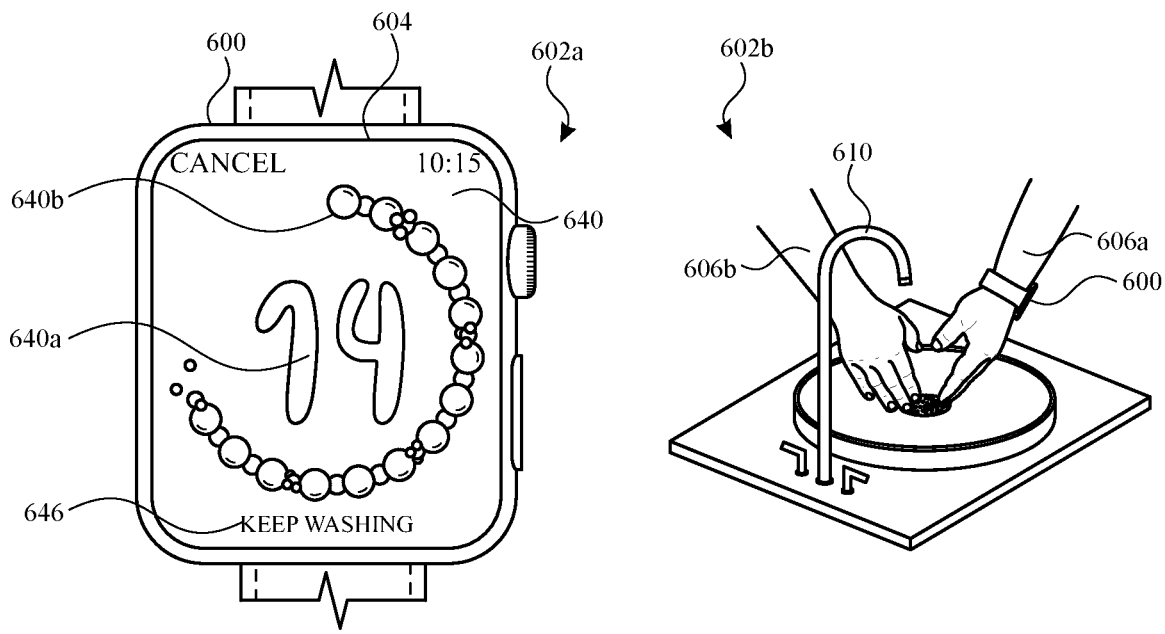

At FIG. 6I, the as-worn view 602b illustrates that the user has paused (e.g., stopped) the physical activity of washing their hands at sink 610, as shown by the position of the user's arms 606a and 606b, and sink 610 is off. As shown in the enlarged view, upon detecting sensor data that device 600 identifies as corresponding to a pause in the physical activity of handwashing (e.g., device 600 detects a cessation of sensor data that indicates handwashing after detecting such data for a period of time), device 600 pauses the current handwashing event by displaying handwashing user interface 640 with countdown timer 640a stopped at "14," indicating that device 600 detected sensor data corresponding to the current handwashing event for 6 seconds (e.g., the handwashing event was ongoing for 6 seconds). In some embodiments, device 600 pauses the current handwashing event based on sensor data corresponding to the user not washing their hands. In some embodiments, device 600 pauses the current handwashing event based on sensor data corresponding to a change in audio data (e.g. water is no longer running in sink 610).

At FIG. 6I, device 600 ceases animating progress indicator 640b and outputting audio feedback and tactile feedback. In some embodiments, device 600 outputs different audio feedback and/or tactile feedback. After a predetermined amount of time (e.g., 2 seconds) of detecting sensor data corresponding to a pause in the handwashing event, device 600 displays prompt 646 ("KEEP WASHING") to continue the physical activity of handwashing on handwashing user interface 640. In some embodiments, device 600 outputs audio feedback and/or tactile feedback with display of the prompt.

Figure 6J:
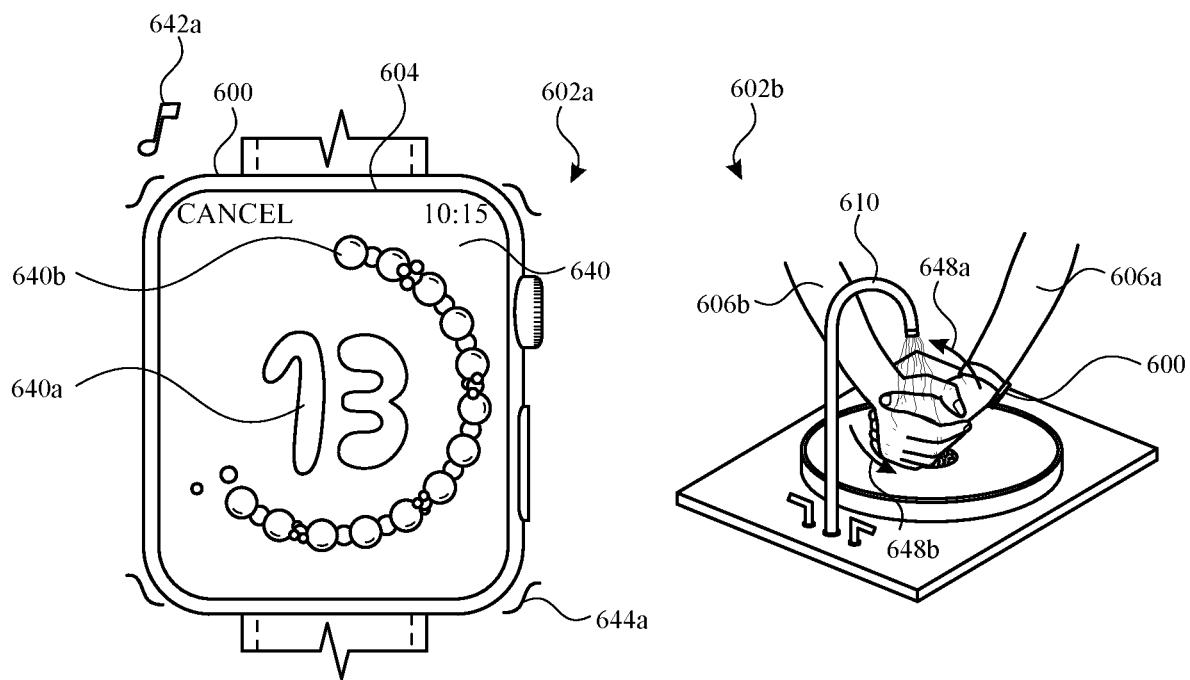

After device 600 displays prompt 646, if device 600 detects sensor data that device 600 identifies as corresponding to restarting (e.g. continues, resumes) the physical activity of handwashing (e.g., the handwashing event) within a predetermined amount of time (e.g., 5 seconds, 8 seconds, 10 seconds), device 600 resumes the countdown timer 640a and animation of progress indicator 640b, as shown in FIG. 6J. In some embodiments, if device 600 does not detect sensor data corresponding to restarting the handwashing event (e.g., within a predetermined time after pausing), device 600 ceases displaying handwashing user interface 640 and displays attempted completion user interface 652 as shown in FIG. 6M, which is discussed in more detail below.

At FIG. 6J, as shown in as-worn view 602b, the user resumes the physical activity of washing their hands at sink 610, as illustrated by arms 606a and 606b and movement arrows 648a and 648b. Device 600 detects sensor data that device 600 identifies as corresponding to restarting (e.g., resuming) the physical activity of handwashing. As shown in enlarged view 602a, in response to detecting the sensor data, device 600 resumes countdown timer 640a by displaying "13" on handwashing user interface 640. Device 600 also resumes animating progress indicator 640b and outputting audio feedback 642a and tactile feedback 644a. Thus, the timer is a timer of the duration of the physical activity, as detected by device 600, and not just a timer of the passage of time. For example, a user may stop and pause repeatedly without advancing the timer. As device 600 continues detecting sensor data corresponding to the current handwashing event, device 600 maintains display of handwashing user interface 640 while countdown timer 640a and progress indicator 640b progress to "1," as shown in FIG. 6K.

Figure 6K:
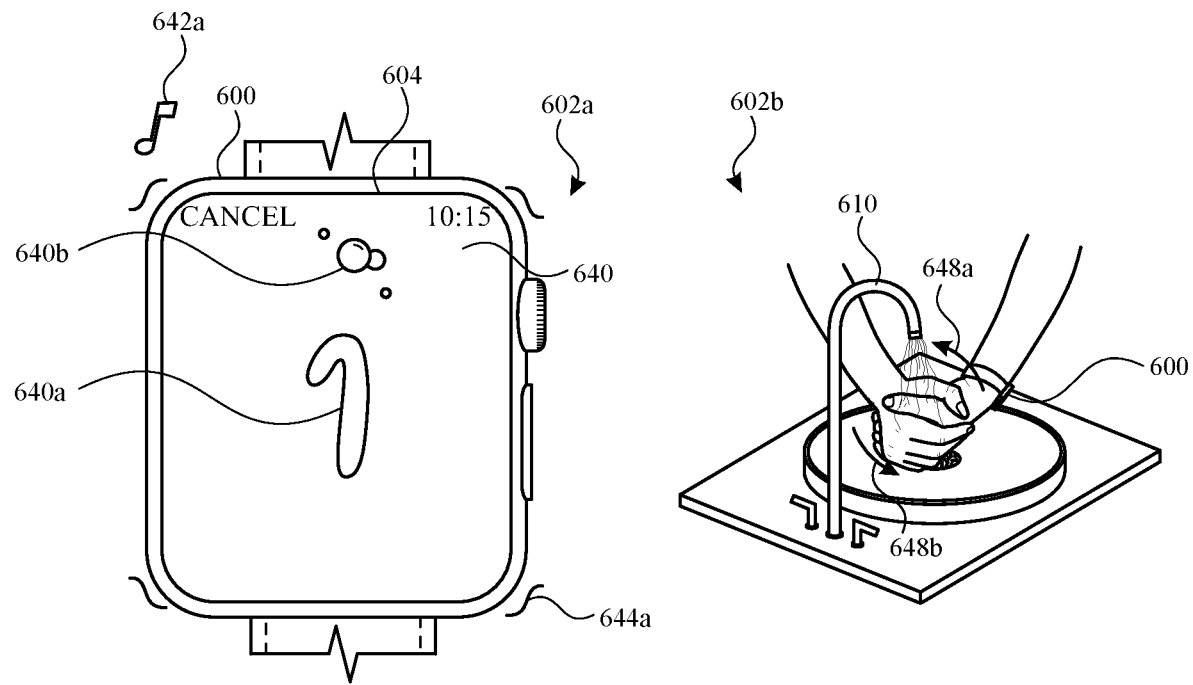

At FIG. 6K in enlarged view 602a, device 600 displays handwashing user interface 640 with countdown timer 640a at "1" and progress indicator 640b nearly at completion (e.g., 19/20 of the circle of bubbles popped), which indicate that device 600 detected sensor data for a total of 19 seconds. Device 600 also outputs audio feedback 642a and tactile feedback 644a, as previously described with respect to FIG. 6H. At as-worn view 602b, the user continues the physical activity of washing their hands, as illustrated by movement arrows 648a and 648b, at sink 610 until FIG. 6L.

Figure 6L:
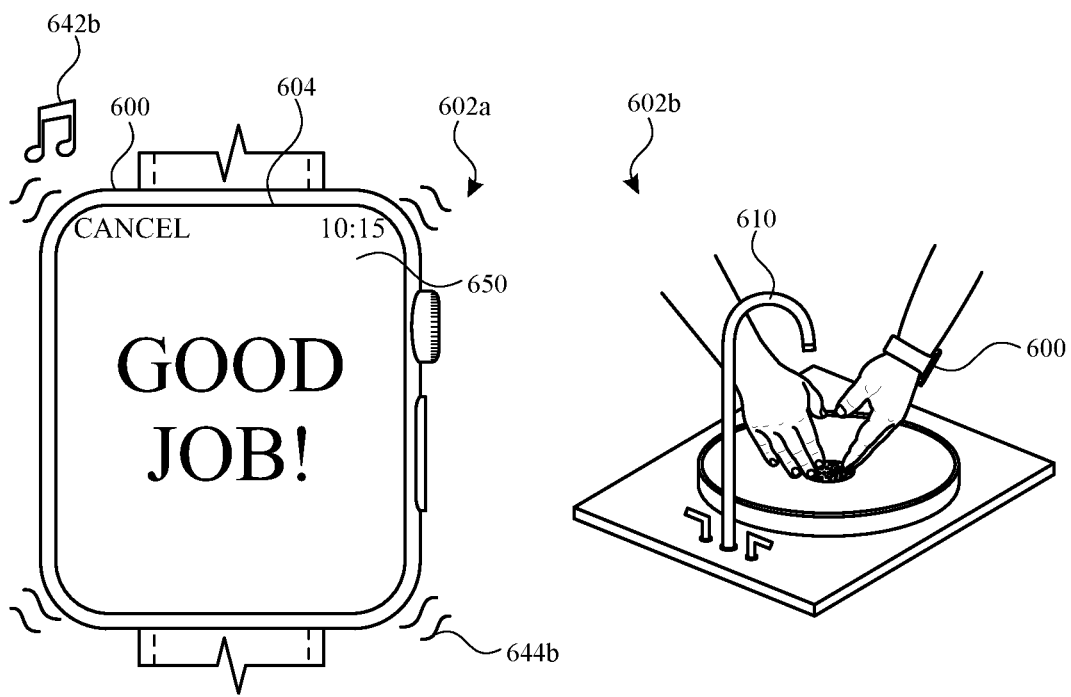
Figure 6M:
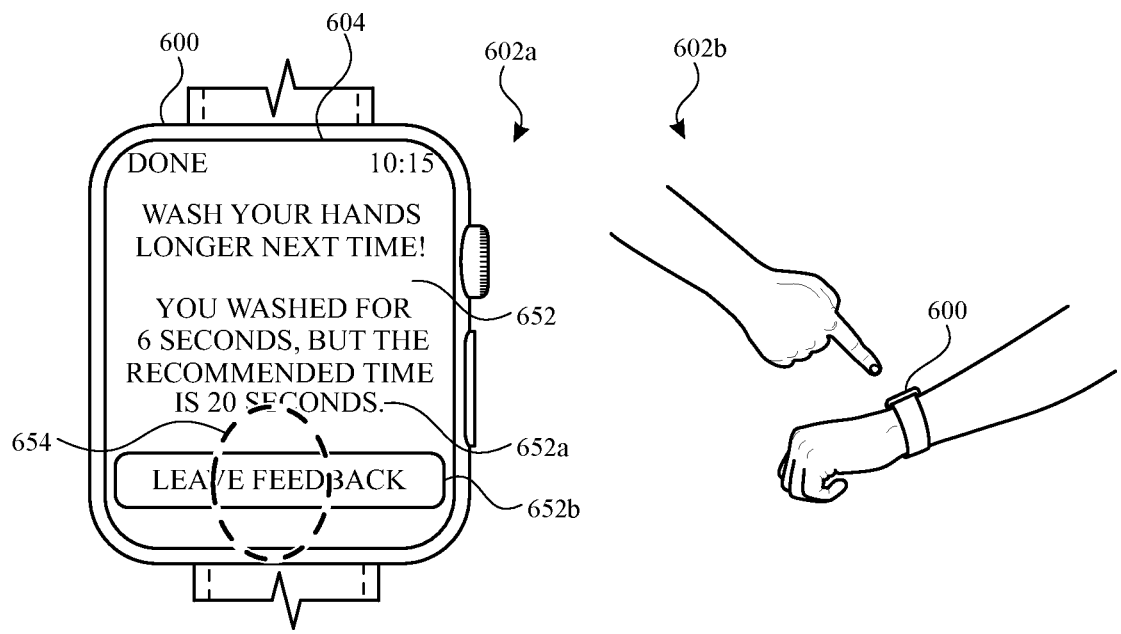

At FIG. 6L in enlarged view 602a, upon detection of sensor data for a total of 20 seconds, device 600 displays successful completion user interface 650 ("GOOD JOB!") on touchscreen display 604. Device 600 concurrently outputs completion audio feedback 642b (e.g., a larger bubble bursting sound, a louder bubble bursting sound) and completion tactile feedback 644b (e.g., a strong haptic vibration). In some embodiments, completion audio feedback 642b is the same as audio feedback 642a. In some embodiments, completion tactile feedback 644b is the same as tactile feedback 644a. Audio feedback 642b and tactile feedback 644b indicate to the user that device 600 detected sensor data corresponding to the current handwashing event for at least the threshold amount of time required for a successfully completed handwashing event. As shown in as-worn view 602b, the user ceases the physical activity of handwashing and sink 610 is off (e.g., water is not running). In some embodiments, successful completion user interface 650 is displayed even if the user continues with the handwashing activity, as successful completion user interface 650 is displayed when the user hand washes for at least the threshold amount of time (e.g., 20 seconds). In some embodiments, successful completion user interface 650 is not displayed until device 600 detects that the user has completed handwashing, to improve the probability that the user will notice the interface.

Handwashing events are tracked (e.g., logged) in a corresponding application on a separate electronic device (e.g., a paired phone), for which operation of this tracking feature is discussed in more detail with reference to FIGS. 6V-6W, below. Handwashing events tracked in the corresponding application are separated into successfully completed handwashing events and attempted handwashing events. As described with respect to FIG. 6L, a successfully completed handwashing event is a handwashing event occurring for at least a threshold amount of time (e.g., 20 seconds). In some embodiments, attempted handwashing events are handwashing events occurring for longer than a predetermined amount of time (e.g., 3 seconds), but less than the threshold amount of time (e.g., 20 seconds). In some embodiments, handwashing events occurring for less than 3 seconds are not tracked in the corresponding application.

Turning back to FIG. 6I, if device 600 does not detect sensor data corresponding to restarting (e.g., resuming) the handwashing event within a predetermined period of time (e.g., 5 seconds, 8, seconds, 10 seconds), device 600 ceases displaying handwashing user interface 640 and displays attempted completion user interface 652, as shown in enlarged view 602a of FIG. 6M. Attempted completion user interface 652 includes instructional text 652a, detailing how long device 600 detected sensor data for the current handwashing event (e.g., 6 seconds) and the threshold (e.g., recommended or user-selected threshold) duration of detecting sensor data for a handwashing event to be considered a successfully completed handwashing event (e.g., 20 seconds). In some embodiments, instructional text 652a includes how much longer detection of sensor data would have needed to occur for the current handwashing event to be considered a successfully completed handwashing event (e.g., 14 more seconds). In some embodiments, instructional text 652a includes comparisons to historic handwashing event durations (e.g., the user washed their hands longer than last handwashing event, "You washed 5 seconds longer than last time").

In enlarged view 602a of FIG. 6M, attempted completion user interface 652 further includes feedback affordance 652b ("LEAVE FEEDBACK") and done affordance 652c. In response to detecting (e.g., receiving) an input (e.g. a tap) corresponding to selection of done affordance 652c, device 600 ceases displaying attempted completion user interface 652 and displays watch face user interface 634, as described with respect to FIG. 6F. As shown in FIG. 6M, device 600 detects (e.g. receives) an input 654 (e.g., a tap) at feedback affordance 652b. In response to detecting input 654, device 600 displays feedback user interface 656, as shown in FIG. 6N.

Figure 6N:
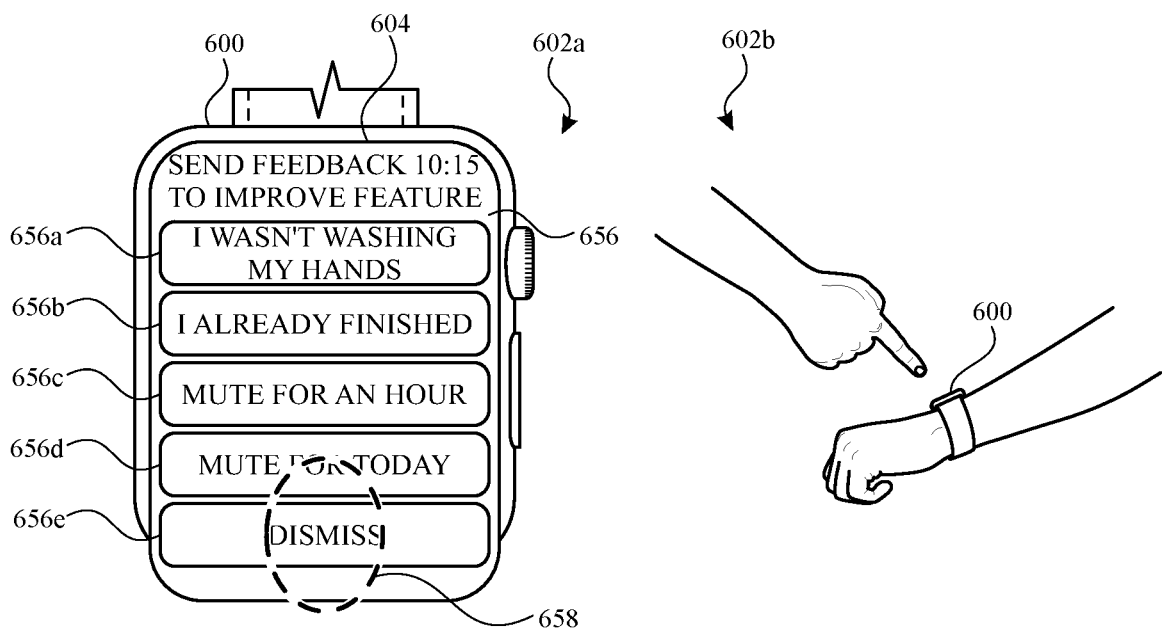

At FIG. 6N, device 600 displays feedback user interface 656 on touchscreen display 604. Feedback user interface 656 includes affordances 656a-656e. As shown in the as-worn view 602b of FIG. 6N, the user performs a gesture on device 600. Turning back to the enlarged view 602a, while displaying feedback user interface 656, device 600 receives (e.g., detects) input 658 (e.g., a tap) corresponding to selection of dismiss affordance 656e. In response to detecting input 658, device 600 ceases displaying feedback user interface 656 and displays watch face user interface 634 as described with respect to FIG. 6F.

In some embodiments, device 600 receives inputs corresponding to selection of affordances 656a-656d. Device responds to these alternative inputs, as follows. In response to receiving an input on affordance 656a ("I WASN'T WASHING MY HANDS"), device 600 receives confirmation that the user was not engaged in the physical activity of washing their hands. In some embodiments, events that are marked as such are excluded from the logging (e.g., tracking) discussed with reference to FIG. 6W, below. In response to receiving an input on affordance 656b ("I ALREADY FINISHED"), device 600 receives confirmation that the user completed the physical activity of washing their hands. In some embodiments, events that are marked as such are tracked as a completed handwashing event for the logging discussed with reference to FIG. 6W, below. In response to receiving an input on affordance 656c ("MUTE FOR AN HOUR"), device 600 suppresses the handwashing detection and tracking feature for 1 hour. In response to receiving an input on affordance 656d ("MUTE FOR TODAY"), device 600 suppresses the handwashing detection and tracking feature for the remainder of the current day. In some embodiments, suppressing the handwashing detection and tracking feature disables the display of handwashing user interface 640, as described with respect to FIG. 6G, while maintaining the tracking of handwashing events in the background. In some embodiments, suppressing the handwashing detection and tracking feature disables the display of handwashing user interface 640 and the tracking of handwashing events in the background.

Figure 6O:
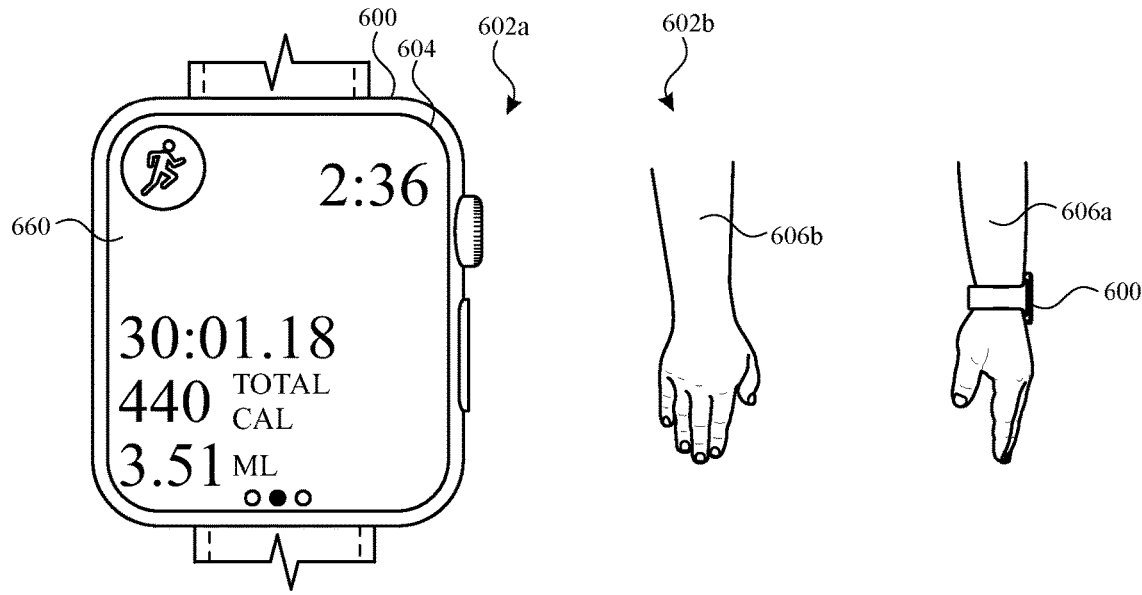

Turning now to FIG. 6O, in enlarged view 602a, device 600 is currently running the workout application, as shown by displaying workout user interface 660 on touchscreen display 604. In some embodiments, device 600 is running one of a variety of watch applications (e.g., workout, music, phone call, or voice recording). In as-worn view 602b, the user's arms 606a and 606b are in a non-handwashing position (e.g., a natural position for a workout). While displaying workout user interface 660, device 600 detects sensor data (e.g., via microphone 113 and accelerometers 168) that device 600 identifies as corresponding to the start of a handwashing event, as shown in FIG. 6P.

Figure 6P:
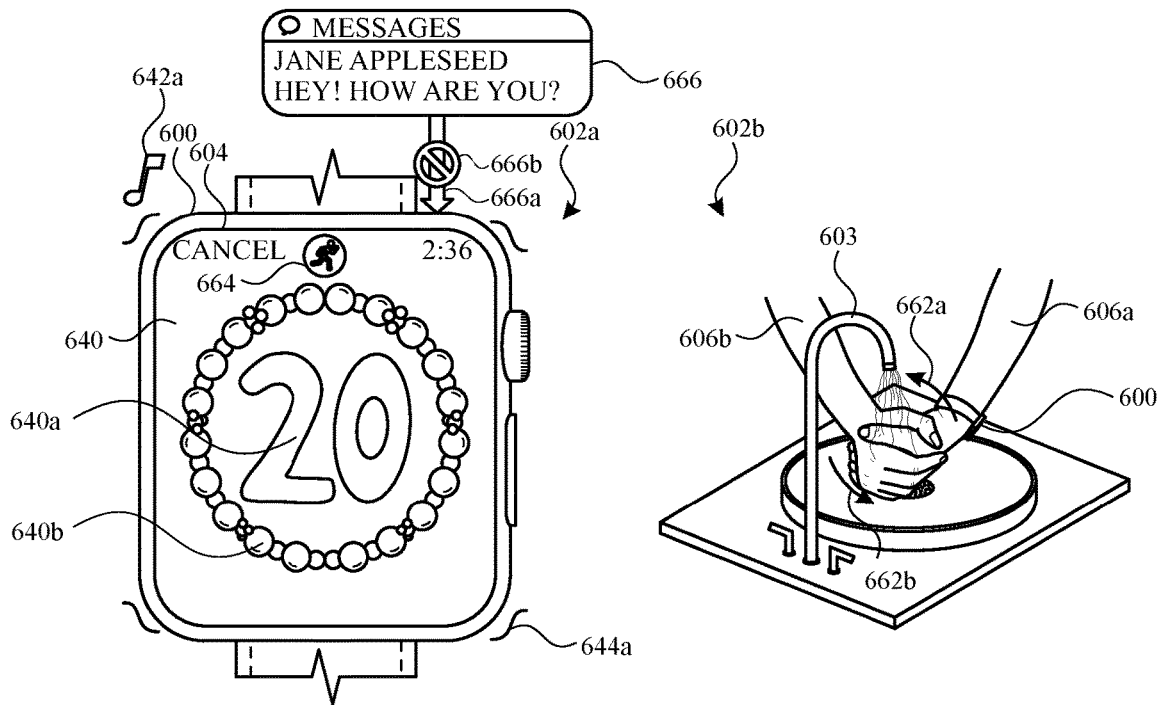

At FIG. 6P, as-worn view 602b shows the user is starting the physical activity of washing their hands at sink 610, as illustrated by movement arrows 662a and 662b. As shown in enlarged view 602a, similar to FIG. 6G, upon detection of the sensor data (e.g., in response to detection of the sensor data), device 600 displays handwashing user interface 640 and outputs audio feedback 642a (e.g., the sound of multiple, small bubbles bursting) and tactile feedback 644a (e.g., a light haptic vibration). Additionally, device 600 displays workout indicator 664 above progress indicator 640b. Workout indicator 664 indicates the workout application is running on device 600 concurrently with displayed handwashing user interface 640. In some embodiments, device 600 displays indicators specific to the one application running out of a variety of watch applications (e.g., workout, music, phone call, or voice recording) at the position of workout indicator 664.

At FIG. 6P in enlarged view 602a, device 600 receives data corresponding to text message 666 from Jane Appleseed. While displaying handwashing user interface 640, device 600 activates a temporary do-not-disturb state by suppressing (e.g., not displaying) the notification corresponding to text message 666, as indicated by block symbol 666b over delivery arrow 666a. In some embodiments, text message 666 is delivered silently (e.g., without displaying a notification). In some embodiments, text message 666 is queued for delivery after completion of the current handwashing event. In some embodiments, critical notifications (e.g., emergency alerts, phone calls, correspondence from prioritized contacts) override the temporary do-not-disturb state and device 600 displays the corresponding notification. In some embodiments, device 600 displays critical notification and maintains the tracking of sensor data corresponding to the handwashing event in the background. In some embodiments, device 600 displays a critical notification and ceases tracking of sensor data corresponding to the handwashing event.

Figure 6Q:
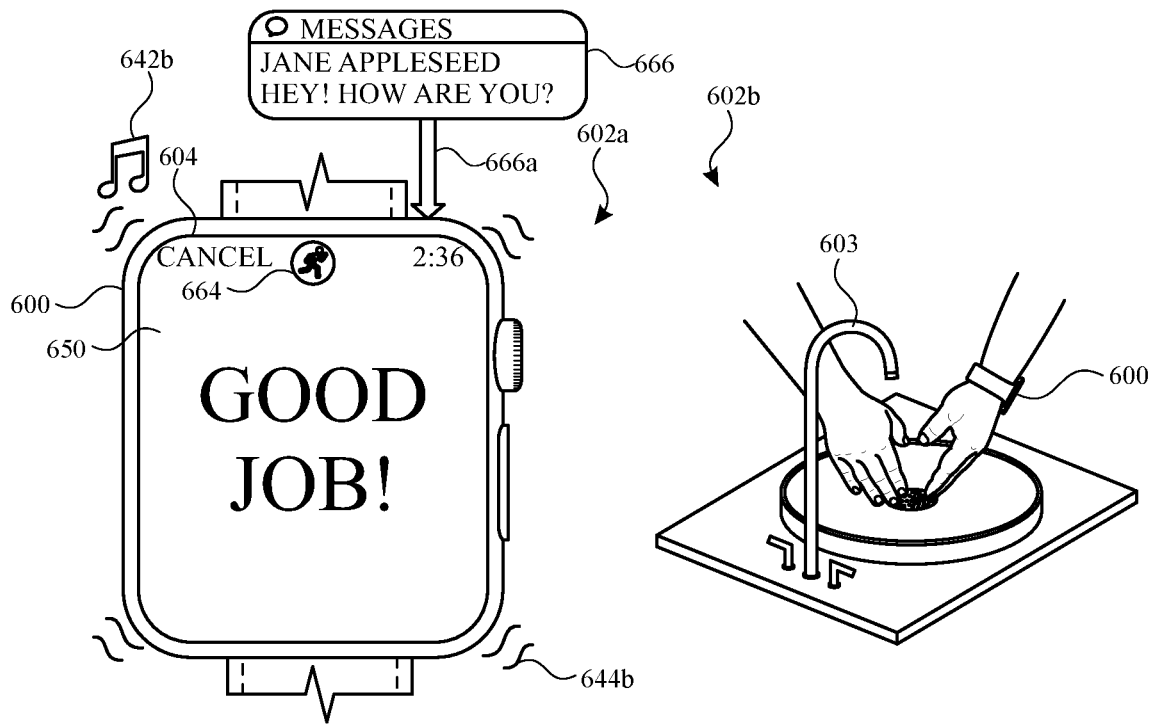
Figure 6R:
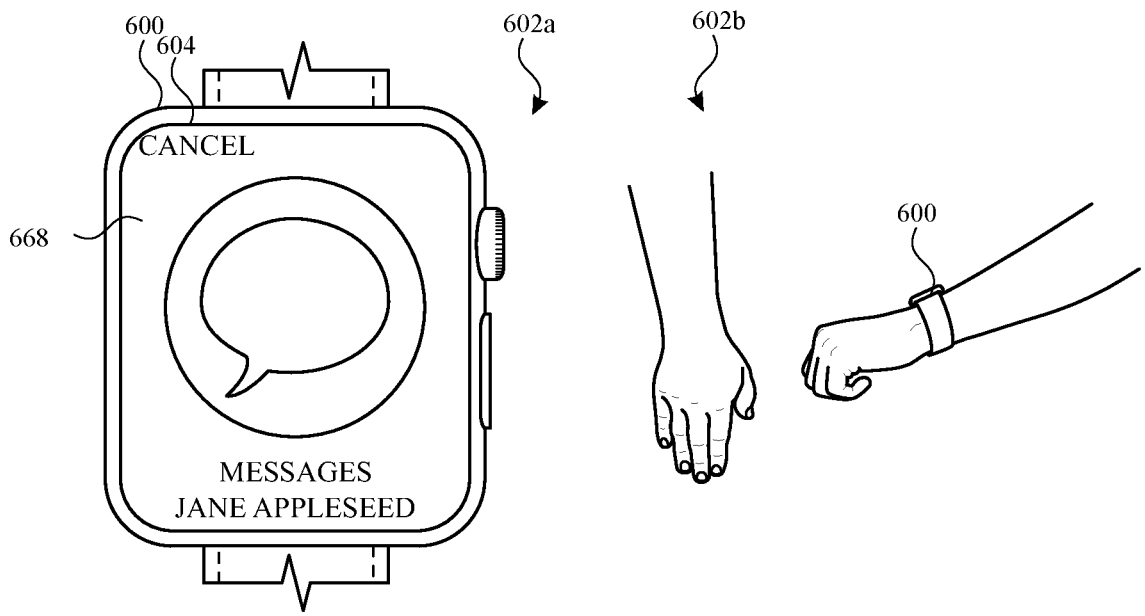

As shown in FIG. 6Q in enlarged view 602a, upon detection of sensor data corresponding to the current handwashing event for a total of 20 seconds, device 600 displays successful completion user interface 650 ("GOOD JOB!") on touchscreen display 604. Device 600 concurrently outputs completion audio feedback 642b (e.g., a larger bubble bursting sound, a louder bubble bursting sound) and completion tactile feedback 644b (e.g., a strong haptic vibration). Device 600 continues displaying workout indicator 664 with successful completion user interface 650. Device 600 delivers the notification corresponding text message 666 by displaying text message notification user interface 668 in FIG. 6R. In some embodiments, text message 666 is delivered silently (e.g., is reviewable via a messaging application) and device 600 does not display text message notification user interface 668 upon completion of the handwashing event.

Figure 6S:
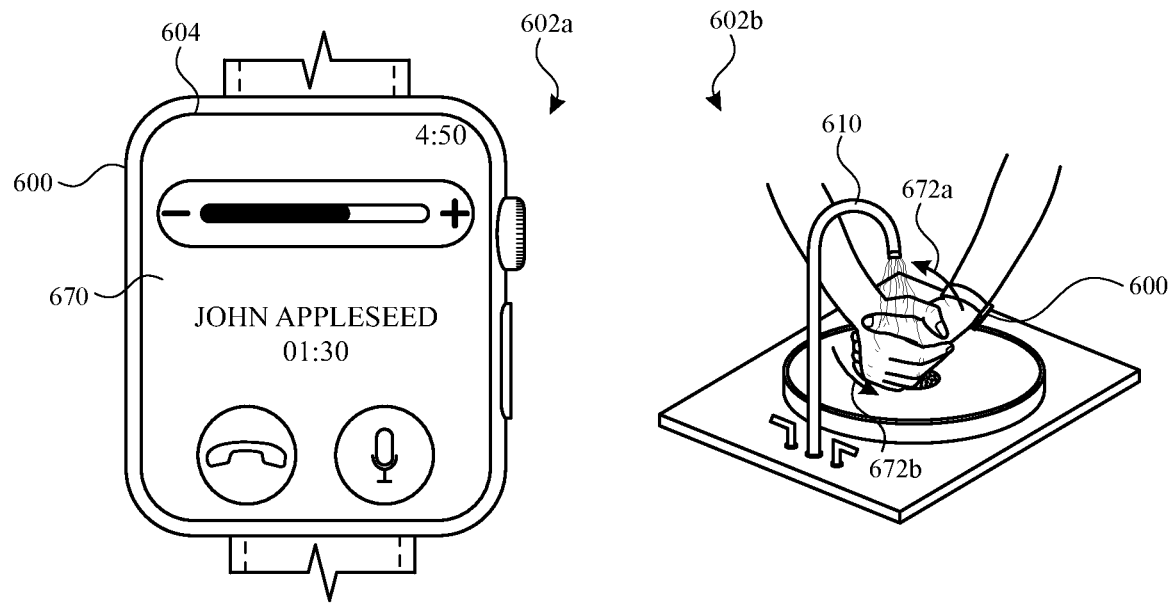

Turning now to FIG. 6S, in enlarged view 602a, device 600 is currently running the phone application corresponding to a phone call, as shown by displaying phone user interface 670 on touchscreen display 604. As-worn view 602b shows the user is starting the physical activity of washing their hands at sink 610, as illustrated by movement arrows 672a and 672b. While running the phone application and upon detection of the sensor data (e.g., in response to detection of the sensor data), device 600 maintains display of phone user interface 670. In some embodiments, device 600 maintains running the phone call application and concurrently initiates the tracking of sensor data corresponding to the handwashing event in the background. In some embodiments, device 600 forgoes tracking the sensor data corresponding to the handwashing event while running the phone application. Upon detection that the phone call has ended, device 600 displays watch face user interface 634, as shown in FIG. 6T.

Figure 6T:
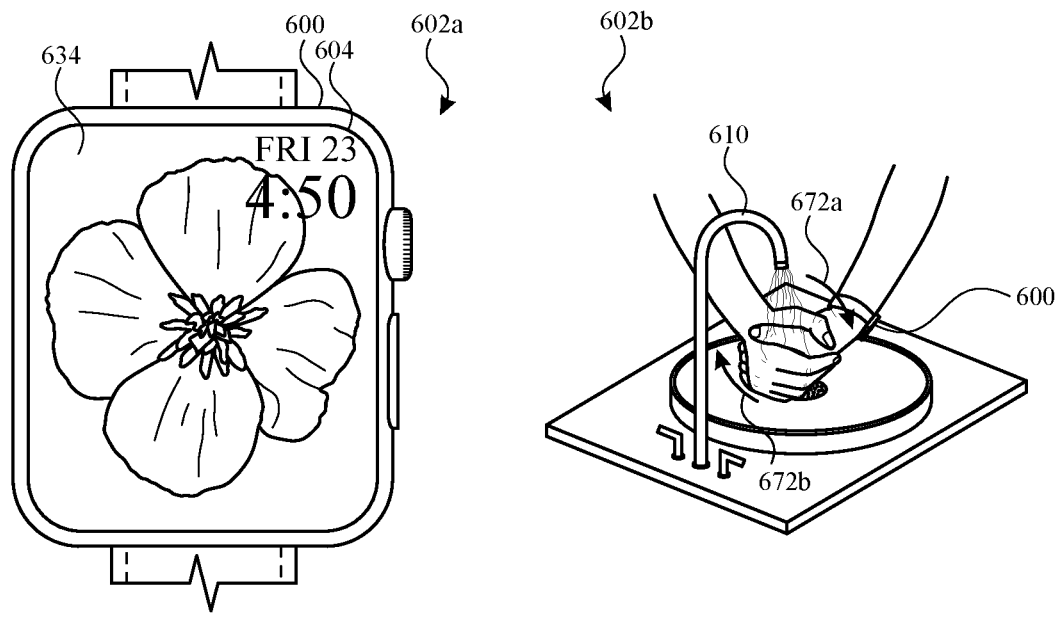

At FIG. 6T, device 600 is displaying watch face user interface 634 in enlarged view 602a, after the phone call has ended. As shown in as-worn view 602b, the user continues (e.g., maintains) the physical activity of washing their hands at sink 610, as illustrated by movement arrows 672a and 672b. In some embodiments, device 600 maintains display of watch face user interface 634 while maintaining the tracking of sensor data corresponding to the handwashing event in the background. In some embodiments, device 600 displays handwashing user interface 640 as illustrated in FIG. 6G, including countdown timer 640a displaying the duration of time remaining for detection of sensor data corresponding to the current handwashing event to meet the minimum threshold duration for the handwashing event to be considered successfully completed. In such embodiments, device 600 also displays handwashing user interface 640 with progress indicator 640b displaying the corresponding partial bubble circle, and outputs audio and tactile feedback. In some embodiments, device 600 maintains display of watch face user interface 634 without tracking the sensor data corresponding to the handwashing event.

Figure 6U:
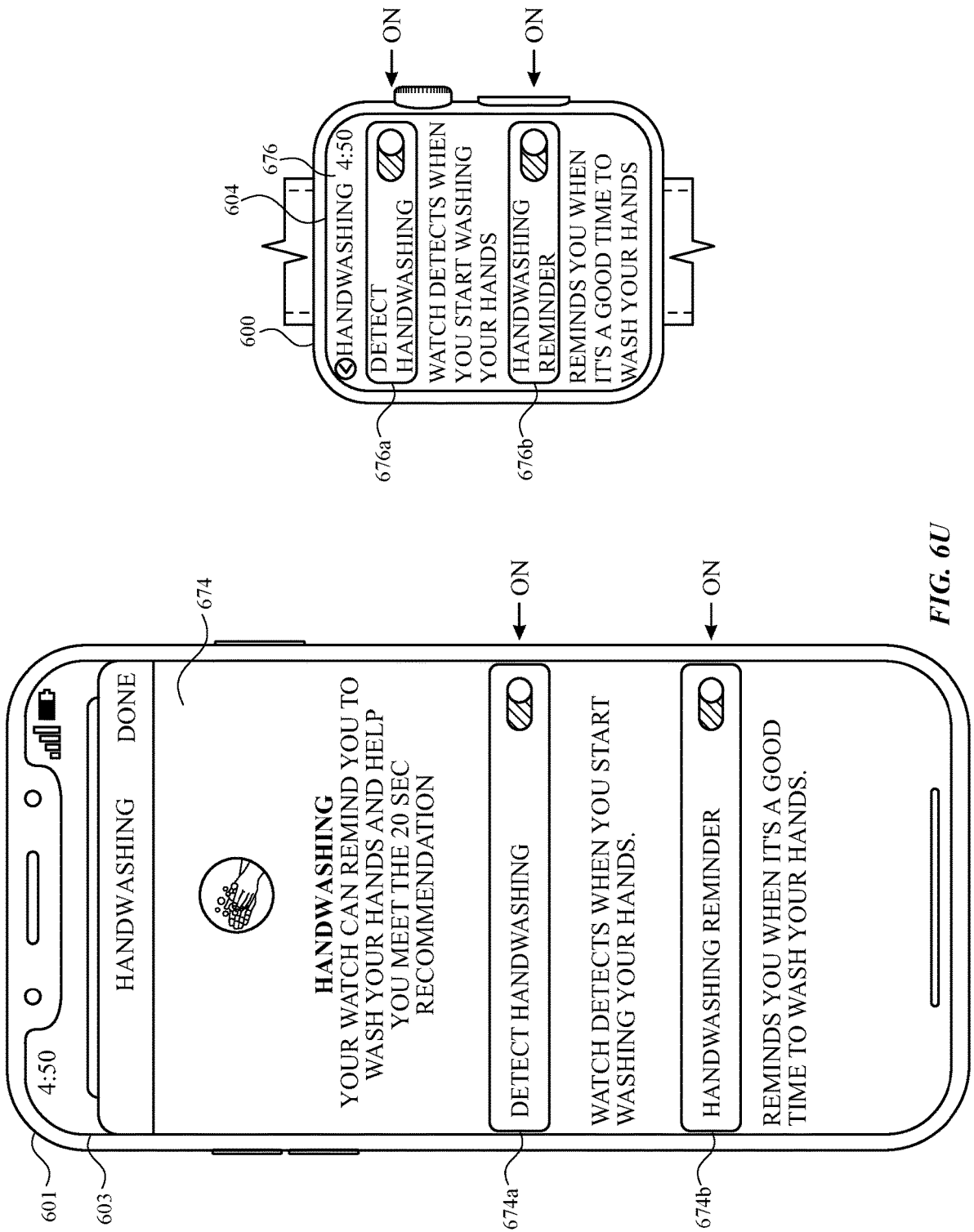

FIG. 6U illustrates device 601 on the left side and device 600 on the right side. Device 601 is a smartphone paired (e.g., in communication) with device 600, which is a smart watch. In some embodiments, device 601 includes one or more features or elements of device 100, 300, and 500. Device 601 displays, on touchscreen display 603, handwashing settings user interface 674. Handwashing settings user interface 674 includes descriptive text about the handwashing detection and tracking feature, detect handwashing affordance 674a, and handwashing reminder affordance 674b. Detect handwashing affordance 674a includes a toggle set to the ON position, which enables device 600 to detect sensor data that device 600 identifies as corresponding to the start of a handwashing event, as described with respect to FIGS. 6F-6L. Selection of the toggle in detect handwashing affordance 674a would update the toggle to the OFF position and disable device 600 from detecting sensor data corresponding a handwashing event. Handwashing reminder affordance 674b includes a toggle set to the ON position, which enables device 600 to display handwashing reminder notifications similar to those described with respect to FIG. 6E. Selection of the toggle in handwashing reminder affordance 674b would update the toggle to the OFF position and disable device 600 from displaying handwashing reminder notifications. In some embodiments, detect handwashing affordance 674a and handwashing reminder affordance 674b operate independently. In some embodiments, the toggle OFF position of detect handwashing affordance 674a also disables handwashing reminder affordance 674b and handwashing reminder notifications.

Further, FIG. 6U illustrates device 600 displaying, on touchscreen display 604, handwashing settings user interface 676. Handwashing settings user interface 676 includes descriptive text about handwashing the handwashing detection and tracking feature, detect handwashing affordance 676a, and handwashing reminder affordance 676b. Detect handwashing affordance 676a includes a toggle set to the ON position, which enables device 600 to detect sensor data that device 600 identifies as corresponding to the start of a handwashing event, as described with respect to FIGS. 6F-6L. Selection of the toggle in detect handwashing affordance 676a would update the toggle to the OFF position and disable device 600 from detecting sensor data corresponding a handwashing event. Handwashing reminder affordance 676b includes a toggle set to the ON position, which enables device 600 to display handwashing reminder notifications similar to those described with respect to FIG. 6E. Selection of the toggle in handwashing reminder affordance 676b would update the toggle to the OFF position and disable device 600 from displaying handwashing reminder notifications. Since device 601 and device 600 are paired, handwashing settings user interface 674 of device 601 and handwashing settings user interface 676 of device 600 are synced and the settings can be updated from either device.

Figure 6V:
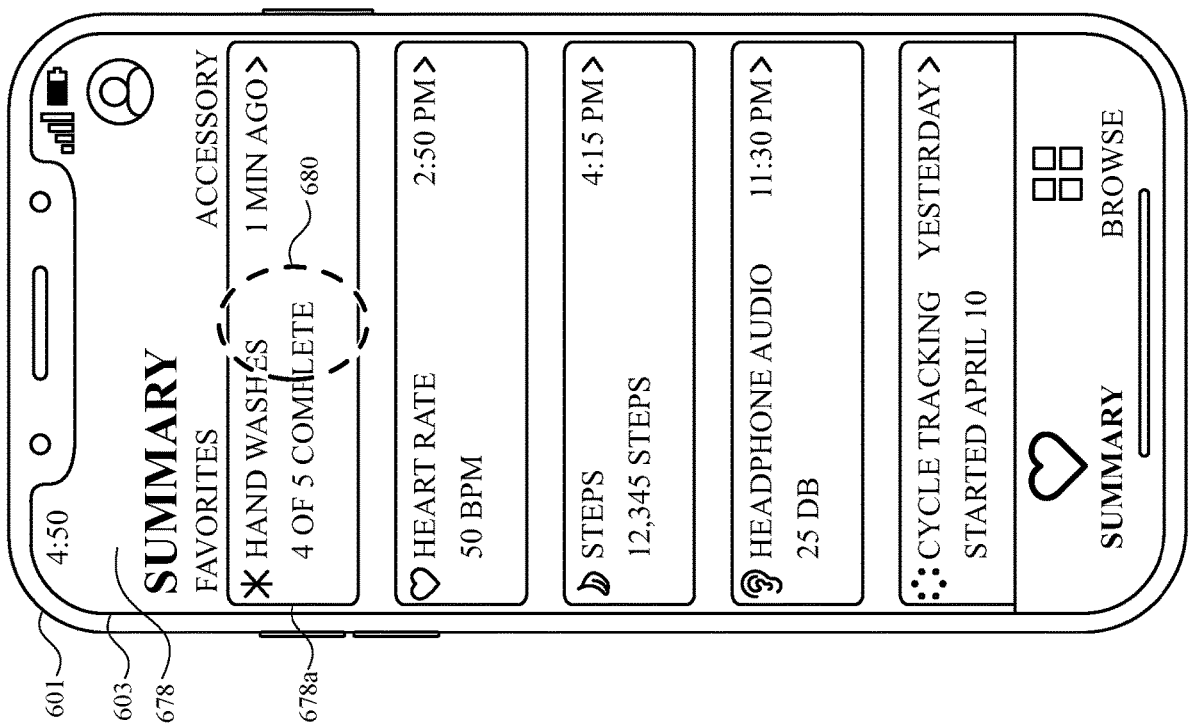

Turning now to FIG. 6V, device 601 displays, on touchscreen display 603, health user interface 678. Health user interface 678 is part of a companion application (e.g., an application (e.g., health app) of a device that is in communication with device 600) that includes tracked user handwashing data. Health user interface 678 includes a plurality of health-related affordances corresponding to various tracked user data. Specifically, hand washes affordance 678a corresponds to the handwashing detection and tracking feature discussed in FIGS. 6A-6T. Hand washes affordance 678a includes metrics of the number of completed and attempted (e.g., started, but not completed) handwashing events (e.g., "4 OF 5 COMPLETE"). In some embodiments, device 600 tracks handwashing events in the background (e.g., does not display handwashing user interface 640) and logs (e.g. tracks) the handwashing event in the companion application. Device 601 detects (e.g., receives) input 680 (e.g., a tap) corresponding to the selection of hand washes affordance 678a. In response to detecting input 680, device 601 displays, on touchscreen display 603, hand washes data user interface 682, as shown in FIG. 6W.

At FIG. 6W, device 600 displays, on touchscreen display 603, hand washes data user interface 682, which includes graph region 682a and time period selection affordance 682b (e.g., day, week, month, year). Time period selection affordance 682b currently shows "D" selected, for displaying graph region 682a in a day-long period along the x-axis. The y-axis of graph region 682a indicates the number of handwashing events. Graph region 682a illustrates 2 completed handwashing events after 6 AM and before 12 PM, as indicated by the black bar at 6 AM along the x-axis. Further, graph region 682a illustrates 2 completed handwashing events, as indicated by the black portion of the bar at 12 PM along the x-axis, and 1 attempted handwashing event, as indicated by the white portion of the bar, after 12 PM and before 6 PM.

FIGS. 7A-7C is a flow diagram illustrating a method for tracking the performance of a physical activity event using an electronic device in accordance with some embodiments. Method 700 is performed at computer system (e.g., 600, 601) (e.g., a smart watch, a smart phone) that is in communication with one or more perceptual output generation components (e.g., 604; 110; 161) (e.g., a display (e.g., a touchscreen display); a speaker; a tactile output generator) and one or more sensors (e.g., 113; 168) (e.g. gyroscope, accelerometer, microphone, a touch-sensitive surface). Some operations in method 700 are, optionally, combined, the orders of some operations are, optionally, changed, and some operations are, optionally, omitted.

In some embodiments, the electronic device (e.g., 600, 601) is a computer system. The computer system is optionally in communication (e.g., wired communication, wireless communication) with one or more perceptual output generation components and with one or more sensors. The perceptual output generation components are configured to provide one or more of audio output, haptic output, or visual output, such as display via a CRT display, display via an LED display, or display via image projection. In some embodiments, the perceptual output generation components are integrated with the computer system. In some embodiments, the perceptual output generation components are separate from the computer system. Thus, the computer system can transmit, via a wired or wireless connection, data (e.g., audio data, haptic data, image data or video data) to an integrated or external perceptual output generation component to perceptually produce the content (e.g., using a display device).

As described below, method 700 provides an intuitive way for tracking the performance of a physical activity event. The method reduces the cognitive burden on a user for tracking the performance of a physical activity event, thereby creating a more efficient human-machine interface. For battery-operated computing devices, enabling a user to tracking the performance of a physical activity event faster and more efficiently conserves power and increases the time between battery charges.

In method 700, the computer system detects (702), via the one or more sensors, a first set of sensor data (e.g., the data detected by device 600 in FIG. 6G (e.g., from 113 and/or 168)) (e.g., accelerometer and/or gyroscope data that is indicative of the user's hand moving in a pattern; audio data that indicates certain ambient sounds (e.g., running water)) that corresponds to a user of the computer system starting a physical activity of a first type (e.g., the handwashing of FIG. 6G). In some embodiments, the first set of sensor data satisfies a first set of activity criteria (e.g., a set of criteria that, when satisfied, indicates that the user activity (e.g., movement) qualifies as an activity event that matches predefined parameters (e.g., a handwashing event)). In some embodiments, the first set of activity criteria is a set of handwashing event criteria (e.g., based on one or more of the techniques disclosed in Appendix A).

In response (704) to detecting the first set of sensor data that corresponds to the user of the computer system (e.g., the user whose arms are depicted as 606a and 606b) starting the physical activity of the first type, the computer system starts (706) (e.g., automatically initiating) a timer of a respective (e.g., predetermined) duration (e.g., a timer corresponding to countdown timer 640a (e.g., 20 seconds)).

In response (704) to detecting the first set of sensor data that corresponds to the user of the computer system (e.g., the user whose arms are depicted as 606a and 606b) starting the physical activity of the first type, the computer system outputs (708), via the one or more perceptual output generation components, a first perceptual feedback (e.g., 640; 642a; 644a) indicating that the timer of the respective duration is operating (e.g., actively timing, not paused, running). In some embodiments, the perceptual indication is a visual or audio count (a count up or a countdown) that continues while the physical activity of the first type continues to be detected.

After (710) starting the first timer and in accordance with a determination that the physical activity of the first type is ongoing (e.g., in accordance with continuing to detect sensor data that corresponds physical activity of the first type), the computer system continues (712) to output the first perceptual feedback indicating that the timer of the respective duration is operating.

After (710) starting the first timer, the computer system detects (714) that a set of one or more termination criteria (e.g., criteria discussed at FIG. 6I corresponding to cessation of handwashing; criteria discussed at FIG. 6L corresponding to completion of handwashing). In some embodiments, the set of one or more termination criteria is a plurality of criteria, each of which, when met, results in termination of the timer) has been met (e.g., termination criteria for the timer).

After (710) starting the first timer and in response (716) to detecting that the set of one or more termination criteria has been met and in accordance with a determination that the set of one or more termination criteria was met based on the physical activity of the first type having continued for at least the respective duration (e.g., 20 seconds as discussed with respect to FIG. 6G)), the computer system outputs (718), via the one or more perceptual output generation components, a second perceptual feedback (628; 624B; 626B) (e.g., audio feedback, visual feedback, haptic feedback) indicating that the physical activity of the first type was detected for the respective duration. In some embodiments, in response to detecting that the set of one or more termination criteria met, ceasing operation of the timer (e.g., pausing the timer, ending the timer). Providing perceptual feedback indicating that the physical activity of the first type was detected for the respective duration provides the user with feedback as to the sensor data being detected by the system. Providing improved feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently. Providing first perceptual feedback indicating that the timer of the respective duration is operating enables a user to properly operate the computer system (e.g., properly continue to perform the physical activity in a manner that is detectable by the system). For example, the internal state prevailing in the computer system dynamically changes and different perceptual feedback is outputted as a result. Such presentation of dynamic perceptual feedback prompts the user to interact with the computer system, enhancing the operability of the computer system.

In some embodiments, in response to detecting that the set of one or more termination criteria (e.g., criteria discussed at FIG. 6I corresponding to cessation of handwashing; criteria discussed at FIG. 6L corresponding to completion of handwashing) has been met and in accordance with a determination that the termination criteria has been met because the physical activity of the first type (e.g., the handwashing of FIG. 6G) stopped before the timer reached the respective duration (e.g., 20 seconds as discussed with respect to FIG. 6G), the computer system provides (720) a third perceptual feedback (e.g., 646) (e.g., audio feedback, visual feedback, haptic feedback) indicating that the physical activity of the first type is no longer being detected (e.g., no longer being detected by the one or more sensors; that the activity was not detected for at least a predetermined length of time (e.g., 0.5 seconds, 1 seconds, 8 seconds) while the timer is running). In some embodiments, the timer is paused (but not immediately canceled) in response to detecting that the set of one or more termination criteria has been met and in accordance with a determination that the termination criteria has been met because the physical activity stopped before the timer reached the respective duration. Providing perceptual feedback indicating that the physical activity of the first type is no longer being detected provides the user with feedback as to the sensor data being detected by the system. Providing improved feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, after providing the third perceptual feedback (e.g., 646) and in accordance with a determination that the physical activity of the first type (e.g., the handwashing of FIG. 6G) is not detected (e.g., is not once again detected; is not resumed) via the one or more sensors within a second respective duration (e.g., duration discussed at FIG. 6I corresponding to cessation of handwashing; duration discussed at FIG. 6J corresponding to resumption of handwashing) (e.g., a predetermined period of time; 5 seconds, 8 seconds, 10 seconds)) after providing the third perceptual feedback, the computer system provides a fourth perceptual feedback (e.g., 652) indicating that the physical of the first type was not performed for the respective duration of the timer (e.g., "you performed the activity for 5 seconds, but the recommended time is 20 seconds"). Providing perceptual feedback indicating that the physical of the first type was not performed for the respective duration of the timer provides the user with feedback as to the sensor data being detected by the system. Providing improved feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, after providing the fourth perceptual feedback (e.g., 652) indicating that the physical activity of the first type (e.g., the handwashing of FIG. 6G) was not performed for the respective duration of the timer, the computer system displays a first selectable user interface object (e.g., 656*a*) that, when selected, logs (e.g. records; stores information indicating) that the physical activity of the first type was not being performed by the user of the computer system (e.g., logs that the first set of sensor data did not correspond to actual performance of the physical activity of the first type by the user of the computer system). In some embodiments, the user is presented with an affordance for reporting that the user was not performing the physical activity of the first type. Displaying a first selectable user interface object that, when selected, logs that the physical activity of the first type was not being performed by the user of the computer system provides the user with the ability to provide additional information relevant to the sensor data collected by the system and improves the machine-human interaction. Providing additional functionality and improving the machine-human interaction enhances the operability of the computer system and makes the machine-user interface more efficient and effective (e.g., effective at providing computer operations and functions to the user).

In some embodiments, after outputting the fourth perceptual feedback (e.g., 652) indicating that the physical activity of the first type (e.g., the handwashing of FIG. 6G) was not performed for the respective duration of the timer and in accordance with a determination that a set of logging criteria has been met, the computer system logs (e.g., recording), in a first application (e.g., 678) (e.g., a health-data aggregation application) that collects and presents data for a plurality of health-related functions (e.g., 678a; the affordances of 678 in FIG. 6V), that an occurrence (e.g., the text "4 OF 5 COMPLETE" in 678a; the white portion of the bar in 682a) of the physical activity of the first type was detected but was not performed (e.g., not detected) for the respective duration of the timer (e.g., logging an incomplete occurrence of the physical activity of the first type). Logging that an occurrence of the physical activity of the first type was detected but was not performed for the respective duration of the timer generates a record in the first application that the user can access to gain feedback on the sensor data gathered by the computer system. Providing the option to access sensor data logs enhances the operability of the computer system and makes the user-device interface more efficient (e.g., by helping the user access to data) and enabling the user to use the computer system more quickly and efficiently.

In some embodiments, the set of logging criteria includes a criterion that is met when the first occurrence of the physical activity of the first type was detected for at least a third respective duration of time (e.g., duration discussed at FIG. 6L corresponding to attempted handwashing events) (e.g., a duration of time that is less than the first respective duration of time; 3 seconds, 5 seconds, 10 seconds). In some embodiments, activity occurrences that are detected for less than a threshold amount of time are not logged.

In some embodiments, the third perceptual feedback (724) is a prompt (e.g., 646) (e.g., an audio prompt, a visual prompt) to continue (e.g., to resume) the physical activity of the first type (e.g., the handwashing of FIG. 6G). Providing a prompt to continue the physical activity enables a user to properly operate the computer system (e.g., properly continue to perform the physical activity in a manner that is detectable by the system) and provides feedback to the user that the system is no longer detecting the physical activity. For example, the internal state prevailing in the computer system dynamically changes and different perceptual feedback is outputted as a result. Such presentation of dynamic perceptual feedback prompts the user to further interact with the computer system, enhancing the operability of the computer system.

In some embodiments, in response to detecting that the set of one or more termination criteria (e.g., criteria discussed at FIG. 6I corresponding to cessation of handwashing; criteria discussed at FIG. 6L corresponding to completion of handwashing) has been met and in accordance with a determination that the termination criteria has been met because the physical activity of the first type stopped before the timer reached the respective duration (e.g., 20 seconds as discussed with respect to FIG. 6G), the computer system pausing operation of the timer (e.g., a timer corresponding to countdown timer 640a (e.g., 14 seconds)) (e.g., stopping progression of the timer).

In some embodiments, after providing the third perceptual feedback (e.g., 646) and after pausing operation of the timer and in accordance with a determination that the physical activity of the first type (e.g., the handwashing of FIG. 6G) is detected via the one or more sensors (e.g., is once again detected), the computer system resumes operation of the timer (e.g., resuming at the same point at which the timer was paused). Resuming the timer based on detecting the physical activity again ensures that the timer is synchronized with detected sensor data, improving the timer's accuracy. Improving the accuracy of the timer with respect to detected sensor data enhances the operation of the computer system.

In some embodiments, the respective duration is a predetermined duration (e.g., 20 seconds as discussed with respect to FIG. 6G) (e.g., 10 sec., 20 sec., 30 sec.).

In some embodiments, after outputting the second perceptual feedback (e.g. 640, 642a, 642b, 644a, 644b, 650) indicating that the physical activity of the first type was detected for the respective duration (e.g., 20 seconds as discussed with respect to FIG. 6G), the computer system logs (e.g., recording), in a second application (e.g., 678) (e.g., a health-data aggregation application; the same application as the first application) that collects and presents data for a plurality of health-related functions, that an occurrence (e.g., the text "4 OF 5 COMPLETE" in 678a; the black portion of the bars in 682a) of the physical activity of the first type was detected for the respective duration (e.g., recording that one instance of the completed physical activity was detected). Logging that an occurrence of the physical activity of the first type was detected for the respective duration generates a record in the first application that the user can access to gain feedback on the sensor data gathered by the computer system. Providing the option to access sensor data logs enhances the operability of the computer system and makes the user-device interface more efficient (e.g., by helping the user access to data) and enabling the user to use the computer system more quickly and efficiently.

In some embodiments, prior to detecting the first set of sensor data, the computer system initiates performance of a first operation of a first type (e.g., 660, 670) (e.g., a phone call, media playback, exercise activity tracking, voice recording)

In some embodiments, the computer system continues to perform the first operation of the first type after starting the timer of the respective duration (e.g., 20 seconds as discussed with respect to FIG. 6G) (e.g., performance of the first operation of the first type is not affected by detecting the first set of sensor data or starting the timer). In some embodiments, an operation of second type, different from the first type, that is being performed is terminated/stopped in response to detecting the first set of sensor data.

In some embodiments, while the timer of the respective duration is timing (e.g., actively timing; not paused), the computer system displays an indication (e.g., 664) (e.g., a graphical indication, a textual indication) that corresponds to the first operation of the first type (e.g., 660). In some embodiments, an icon is displayed indicating that active session of an application is running in the background. Displaying an indication that corresponds to the first operation of the first type while the timer is timing provides the user with feedback as to the state of the first operation. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the physical activity of the first type (e.g., the handwashing of FIG. 6G) is handwashing (e.g., cleaning of one or more hands using water (e.g., running water)) by the user of the computer system (e.g., 602b). In some embodiments, the handwashing is detected based on one or more of the techniques disclosed in Appendix A.

In some embodiments, the computer system detects (726) that a set of prompting criteria (e.g., criteria as discussed with respect to FIG. 6E) has been met, wherein the set of prompting criteria includes a criterion that is met when the location of the computer system corresponds to a predefined location (e.g., as shown by text in 630*a*) (e.g., the user's home, the user's workplace).

In some embodiments, in response to detecting that the set of prompting criteria has been met, the computer system outputs (728) a first prompt (e.g., 630) (e.g., an audio prompt; a visual prompt) for the user of the computer system to perform the physical activity of the first type (e.g., the handwashing of FIG. 6G) (e.g., a reminder to wash the user's hands).

In some embodiments, the prompting criteria do not include a criterion that is met when the location of the computer system corresponds to a predefined location. In such embodiments, the prompting criteria include one or more criteria selected from the group consisting of the current time matching a predetermined time of day, detecting physical activity of a first type (e.g., eating, exercising), occurrence of a predetermined event (e.g., a calendar entry), and a user-set reminder (e.g., a reminder that occurs a predetermined amount of time after the reminder is activated (e.g., a 2-hour reminder); a reminder that occurs at a reoccurring time of day (e.g., 5 PM each day). Providing a prompt for the user of the computer system to perform the physical activity of the first type provides the user with feedback as to conditions detected by the system and promotes further system-user interactions. Providing improved visual feedback to the user and promoting system-user interaction enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the set of prompting criteria includes a criterion that is satisfied when the user has remained at the location for a predetermined time after arriving at the location. In some embodiments, the set of prompting criteria includes a criterion that is satisfied when the physical activity of the first type has not been detected during the predetermined time (e.g., 5 minutes, 10 minutes) after arriving at the location. In some embodiments, the set of prompting criteria are not satisfied if the computer system has detected the physical activity of the first type within the predetermined time (e.g., 5 minutes, 10 minutes) after arriving at the location.)

In some embodiments, the computer system detects that recorded data corresponding to performance of the physical activity of the first type (e.g., the handwashing of FIG. 6G) satisfies a set of notification criteria (e.g., criteria discussed at FIG. 6L corresponding to a threshold amount of time). In some embodiments, the set of notification criteria are met when the number of occurrences of the physical activity exceed a target number or when the duration of the latest occurrence of the physical activity exceeds a predetermined number (e.g., the duration of the previous occurrence of the physical activity).

In some embodiments, in response to detecting that the recorded data corresponding to performance of the physical activity of the first type satisfied the set of notification criteria, the computer system outputs a first notification (e.g., 642*b*, 644*b*, 650) (e.g., an audio notification; a visual notification) that includes information (e.g., a count of occurrences of the physical activity); an indication that the length of during which the physical activity has been detected; a length of time one or more occurrences of the physical activity has been detected; a comparison of lengths of time for different occurrences of the physical activity (e.g., an indication that the duration has increased since the last occurrence) based on (e.g., derived from; excerpted from; that is a subset of) the recorded data. Providing a notification that includes information based on the recorded data corresponding to performance of the physical activity of the first type provides the user with feedback as to conditions detected by the system and promotes further system-user interactions. Providing improved visual feedback to the user and promoting system-user interaction enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to detect and track the performance of a physical activity event. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver targeted reminders to the user. Accordingly, use of such personal information data enables users to monitor the frequency and duration of physical activity events. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of tracking the performance of a physical activity event, the present technology can be configured to allow users to select to "opt in" or "opt out" of participation in the collection of personal information data during registration for services or anytime thereafter. In another example, users can select not to provide sensor and location data for tracking the performance of a physical activity event. In yet another example, users can select to limit the sensor data used for tracking the performance of a physical activity event or entirely prohibit tracking the performance of a physical activity event. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, tracking the performance of a physical activity event based on non-personal information data or a bare minimum amount of personal information, such as the content being requested by the device associated with a user, other non-personal information available to the device associated with a user, or publicly available information.

What is claimed is:

1. An electronic device, comprising:
one or more perceptual output generation components;
a plurality of sensors for detecting a physical activity of a first type, including a first sensor for detecting movement corresponding to the physical activity of the first type and a second sensor for detecting sound corresponding to the physical activity of the first type;
one or more processors; and
memory storing one or more programs configured to be executed by the one or more processors, the one or more programs including instructions for:
while the electronic device is being worn by a user of the electronic device, via one or more attachment mechanisms, detecting, via the first sensor and/or the second sensor, a first set of sensor data that corresponds to the user of the electronic device starting a physical activity of a first type;
in response to detecting the first set of sensor data that corresponds to the user of the electronic device, starting the physical activity of the first type:
starting a timer of a respective duration; and
outputting, via the one or more perceptual output generation components, a first perceptual feedback indicating that the timer of the respective duration is operating; and
after starting the timer:
in accordance with a determination that the physical activity of the first type is ongoing, continuing to output the first perceptual feedback indicating that the timer of the respective duration is operating;
detecting that a set of one or more termination criteria has been met;
in response to detecting that the set of one or more termination criteria has been met:
in accordance with a determination that the set of one or more termination criteria was met based on the physical activity of the first type having continued for at least the respective duration, outputting, via the one or more perceptual output generation components, a second perceptual feedback indicating that the physical activity of the first type was detected for the respective duration;
in accordance with a determination that the termination criteria has been met because the physical activity of the first type stopped before the timer reached the respective duration:
providing a third perceptual feedback indicating that the physical activity of the first type is no longer being detected; and
pausing operation of the timer; and
after providing the third perceptual feedback and after pausing operation of the timer:
in accordance with a determination that the physical activity of the first type is detected via the first sensor and/or the second sensor within a second respective duration after providing the third perceptual feedback, resuming operation of the timer;

in accordance with a determination that the physical activity of the first type is not detected via the first sensor and/or the second sensor within a third respective duration after providing the third perceptual feedback, providing a fourth perceptual feedback that is different from the third perceptual feedback, wherein the third respective duration is shorter than the second respective duration; and in accordance with a determination that the physical activity of the first type is not detected via the first sensor and/or the second sensor within the second respective duration after providing the third perceptual feedback, ceasing operation of the timer.

2. The electronic device of claim 1, the one or more programs further including instructions for:

after providing the third perceptual feedback:

in accordance with a determination that the physical activity of the first type is not detected via the first sensor or second sensor within a second respective duration after providing the third perceptual feedback, providing a fifth perceptual feedback indicating that the physical of the first type was not performed for the respective duration of the timer.

3. The electronic device of claim 2, the one or more programs further including instructions for:

after providing the fifth perceptual feedback indicating that the physical activity of the first type was not performed for the respective duration of the timer, displaying a first selectable user interface object that, when selected, logs that the physical activity of the first type was not being performed by the user of the electronic device.

4. The electronic device of claim 2, the one or more programs further including instructions for:

after outputting the fifth perceptual feedback indicating that the physical activity of the first type was not performed for the respective duration of the timer:

in accordance with a determination that a set of logging criteria has been met, logging, in a first application that collects and presents data for a plurality of health-related functions, that an occurrence of the physical activity of the first type was detected but was not performed for the respective duration of the timer.

5. The electronic device of claim 4, wherein the set of logging criteria includes a criterion that is met when the occurrence of the physical activity of the first type was detected for at least a fourth respective duration of time.

6. The electronic device of claim 1, wherein the third perceptual feedback is a prompt to continue the physical activity of the first type.

7. The electronic device of claim 1, wherein the respective duration is a predetermined duration.

8. The electronic device of claim 1, the one or more programs further including instructions for:

after outputting the second perceptual feedback indicating that the physical activity of the first type was detected for the respective duration, logging, in a second application that collects and presents data for a plurality of health-related functions, that an occurrence of the physical activity of the first type was detected for the respective duration.

9. The electronic device of claim 1, the one or more programs further including instructions for:

prior to detecting the first set of sensor data, initiating performance of a first operation of a first type; and continuing to perform the first operation of the first type after starting the timer of the respective duration.

10. The electronic device of claim 9, the one or more programs further including instructions for:

while the timer of the respective duration is timing, displaying an indication that corresponds to the first operation of the first type.

11. The electronic device of claim 1, wherein the physical activity of the first type is handwashing by the user of the electronic device.

12. The electronic device of claim 1, the one or more programs further including instructions for:

detecting that a set of prompting criteria has been met, wherein the set of prompting criteria includes a criterion that is met when a location of the electronic device corresponds to a predefined location; and in response to detecting that the set of prompting criteria has been met, outputting a first prompt for the user of the electronic device to perform the physical activity of the first type.

13. The electronic device of claim 1, the one or more programs further including instructions for:

detecting that recorded data corresponding to performance of the physical activity of the first type satisfies a set of notification criteria; and in response to detecting that the recorded data corresponding to performance of the physical activity of the first type satisfied the set of notification criteria, outputting a first notification that includes information based on the recorded data.

14. A non-transitory computer-readable storage medium storing one or more programs configured to be executed by one or more processors of an electronic device that is in communication with one or more perceptual output generation components and a plurality of sensors for detecting a physical activity of a first type, including a first sensor for detecting movement corresponding to the physical activity of the first type and a second sensor for detecting sound corresponding to the physical activity of the first type:

while the electronic device is being worn by a user of the electronic device, via one or more attachment mechanisms, detecting, via the first sensor and/or the second sensor, a first set of sensor data that corresponds to the user of the electronic device starting a physical activity of a first type;

in response to detecting the first set of sensor data that corresponds to the user of the electronic device, starting the physical activity of the first type:

starting a timer of a respective duration; and outputting, via the one or more perceptual output generation components, a first perceptual feedback indicating that the timer of the respective duration is operating; and after starting the timer:

in accordance with a determination that the physical activity of the first type is ongoing, continuing to output the first perceptual feedback indicating that the timer of the respective duration is operating;

detecting that a set of one or more termination criteria has been met;

in response to detecting that the set of one or more termination criteria has been met:
  in accordance with a determination that the set of one or more termination criteria was met based on the physical activity of the first type having continued for at least the respective duration, outputting, via the one or more perceptual output generation components, a second perceptual feedback indicating that the physical activity of the first type was detected for the respective duration;
  in accordance with a determination that the termination criteria has been met because the physical activity of the first type stopped before the timer reached the respective duration:
    providing a third perceptual feedback indicating that the physical activity of the first type is no longer being detected; and
    pausing operation of the timer; and
  after providing the third perceptual feedback and after pausing operation of the timer:
    in accordance with a determination that the physical activity of the first type is detected via the first sensor and/or the second sensor within a second respective duration after providing the third perceptual feedback, resuming operation of the timer;
    in accordance with a determination that the physical activity of the first type is not detected via the first sensor and/or the second sensor within a third respective duration after providing the third perceptual feedback, providing a fourth perceptual feedback that is different from the third perceptual feedback, wherein the third respective duration is shorter than the second respective duration; and
    in accordance with a determination that the physical activity of the first type is not detected via the first sensor and/or the second sensor within the second respective duration after providing the third perceptual feedback, ceasing operation of the timer.

15. The non-transitory computer-readable storage medium of claim 14, the one or more programs further including instructions for:
  after providing the third perceptual feedback:
    in accordance with a determination that the physical activity of the first type is not detected via the first sensor or the second sensor within a second respective duration after providing the third perceptual feedback, providing a fifth perceptual feedback indicating that the physical of the first type was not performed for the respective duration of the timer.

16. The non-transitory computer-readable storage medium of claim 15, the one or more programs further including instructions for:
  after providing the fifth perceptual feedback indicating that the physical activity of the first type was not performed for the respective duration of the timer, displaying a first selectable user interface object that, when selected, logs that the physical activity of the first type was not being performed by the user of the electronic device.

17. The non-transitory computer-readable storage medium of claim 15, the one or more programs further including instructions for:
  after outputting the fifth perceptual feedback indicating that the physical activity of the first type was not performed for the respective duration of the timer:
    in accordance with a determination that a set of logging criteria has been met, logging, in a first application that collects and presents data for a plurality of health-related functions, that an occurrence of the physical activity of the first type was detected but was not performed for the respective duration of the timer.

18. The non-transitory computer-readable storage medium of claim 17, wherein the set of logging criteria includes a criterion that is met when the occurrence of the physical activity of the first type was detected for at least a fourth respective duration of time.

19. The non-transitory computer-readable storage medium of claim 14, wherein the third perceptual feedback is a prompt to continue the physical activity of the first type.

20. The non-transitory computer-readable storage medium of claim 14, wherein the respective duration is a predetermined duration.

21. The non-transitory computer-readable storage medium of claim 14, the one or more programs further including instructions for:
  after outputting the second perceptual feedback indicating that the physical activity of the first type was detected for the respective duration, logging, in a second application that collects and presents data for a plurality of health-related functions, that an occurrence of the physical activity of the first type was detected for the respective duration.

22. The non-transitory computer-readable storage medium of claim 14, the one or more programs further including instructions for:
  prior to detecting the first set of sensor data, initiating performance of a first operation of a first type; and
  continuing to perform the first operation of the first type after starting the timer of the respective duration.

23. The non-transitory computer-readable storage medium of claim 22, the one or more programs further including instructions for:
  while the timer of the respective duration is timing, displaying an indication that corresponds to the first operation of the first type.

24. The non-transitory computer-readable storage medium of claim 14, wherein the physical activity of the first type is handwashing by the user of the electronic device.

25. The non-transitory computer-readable storage medium of claim 14, the one or more programs further including instructions for:
  detecting that a set of prompting criteria has been met, wherein the set of prompting criteria includes a criterion that is met when a location of the electronic device corresponds to a predefined location; and
  in response to detecting that the set of prompting criteria has been met, outputting a first prompt for the user of the electronic device to perform the physical activity of the first type.

26. The non-transitory computer-readable storage medium of claim 14, the one or more programs further including instructions for:
  detecting that recorded data corresponding to performance of the physical activity of the first type satisfies a set of notification criteria; and
  in response to detecting that the recorded data corresponding to performance of the physical activity of the first type satisfied the set of notification criteria, outputting a first notification that includes information based on the recorded data.

27. A method, comprising:
at an electronic device that is in communication with one or more perceptual output generation components and a plurality of sensors for detecting a physical activity of a first type, including a first sensor for detecting movement corresponding to the physical activity of the first type and a second sensor for detecting sound corresponding to the physical activity of the first type:
while the electronic device is being worn by a user of the electronic device, via one or more attachment mechanisms, detecting, via the first sensor and/or the second sensor, a first set of sensor data that corresponds to the user of the electronic device starting a physical activity of a first type;
in response to detecting the first set of sensor data that corresponds to the user of the electronic device, starting the physical activity of the first type:
starting a timer of a respective duration; and
outputting, via the one or more perceptual output generation components, a first perceptual feedback indicating that the timer of the respective duration is operating; and
after starting the timer:
in accordance with a determination that the physical activity of the first type is ongoing, continuing to output the first perceptual feedback indicating that the timer of the respective duration is operating; and
detecting that a set of one or more termination criteria has been met;
in response to detecting that the set of one or more termination criteria has been met:
in accordance with a determination that the set of one or more termination criteria was met based on the physical activity of the first type having continued for at least the respective duration, outputting, via the one or more perceptual output generation components, a second perceptual feedback indicating that the physical activity of the first type was detected for the respective duration;
in accordance with a determination that the termination criteria has been met because the physical activity of the first type stopped before the timer reached the respective duration:
providing a third perceptual feedback indicating that the physical activity of the first type is no longer being detected; and
pausing operation of the timer; and
after providing the third perceptual feedback and after pausing operation of the timer:
in accordance with a determination that the physical activity of the first type is detected via the first sensor and/or the second sensor within a second respective duration after providing the third perceptual feedback, resuming operation of the timer;
in accordance with a determination that the physical activity of the first type is not detected via the first sensor and/or the second sensor within a third respective duration after providing the third perceptual feedback, providing a fourth perceptual feedback that is different from the third perceptual feedback, wherein the third respective duration is shorter than the second respective duration; and
in accordance with a determination that the physical activity of the first type is not detected via the first sensor and/or the second sensor within the second respective duration after providing the third perceptual feedback, ceasing operation of the timer.

28. The method of claim 27, further comprising:
after providing the third perceptual feedback:
in accordance with a determination that the physical activity of the first type is not detected via the first sensor or the second sensor within a second respective duration after providing the third perceptual feedback, providing a fifth perceptual feedback indicating that the physical of the first type was not performed for the respective duration of the timer.

29. The method of claim 28, further comprising:
after providing the fifth perceptual feedback indicating that the physical activity of the first type was not performed for the respective duration of the timer, displaying a first selectable user interface object that, when selected, logs that the physical activity of the first type was not being performed by the user of the electronic device.

30. The method of claim 28, further comprising:
after outputting the fifth perceptual feedback indicating that the physical activity of the first type was not performed for the respective duration of the timer:
in accordance with a determination that a set of logging criteria has been met, logging, in a first application that collects and presents data for a plurality of health-related functions, that an occurrence of the physical activity of the first type was detected but was not performed for the respective duration of the timer.

31. The method of claim 30, wherein the set of logging criteria includes a criterion that is met when the occurrence of the physical activity of the first type was detected for at least a fourth respective duration of time.

32. The method of claim 27, wherein the third perceptual feedback is a prompt to continue the physical activity of the first type.

33. The method of claim 27, wherein the respective duration is a predetermined duration.

34. The method of claim 27, further comprising:
after outputting the second perceptual feedback indicating that the physical activity of the first type was detected for the respective duration, logging, in a second application that collects and presents data for a plurality of health-related functions, that an occurrence of the physical activity of the first type was detected for the respective duration.

35. The method of claim 27, further comprising:
prior to detecting the first set of sensor data, initiating performance of a first operation of a first type; and
continuing to perform the first operation of the first type after starting the timer of the respective duration.

36. The method of claim 35, further comprising:
while the timer of the respective duration is timing, displaying an indication that corresponds to the first operation of the first type.

37. The method of claim 27, wherein the physical activity of the first type is handwashing by the user of the electronic device.

38. The method of claim 27, further comprising:
detecting that a set of prompting criteria has been met, wherein the set of prompting criteria includes a criterion that is met when a location of the electronic device corresponds to a predefined location; and in response to detecting that the set of prompting criteria has been met, outputting a first prompt for the user of the electronic device to perform the physical activity of the first type.

39. The method of claim 27, further comprising:

detecting that recorded data corresponding to performance of the physical activity of the first type satisfies a set of notification criteria; and in response to detecting that the recorded data corresponding to performance of the physical activity of the first type satisfied the set of notification criteria, outputting a first notification that includes information based on the recorded data.

* * * * *